(12) United States Patent
Hamrah et al.

(10) Patent No.: US 9,877,645 B2
(45) Date of Patent: *Jan. 30, 2018

(54) INFLAMMATORY EYE DISORDERS

(71) Applicant: Massachusetts Eye and Ear Infirmary, Boston, MA (US)

(72) Inventors: Pedram Hamrah, Wellesley, MA (US); Reza Dana, Newton, MA (US); Bernardo Cavalcanti, Recife (BR); Andrea Cruzat, Santiago (CL)

(73) Assignee: Massachusetts Eye and Ear Infirmary, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/411,803

(22) Filed: Jan. 20, 2017

(65) Prior Publication Data
US 2017/0188814 A1 Jul. 6, 2017

Related U.S. Application Data

(63) Continuation of application No. 14/379,380, filed as application No. PCT/US2013/027181 on Feb. 21, 2013, now Pat. No. 9,549,966.

(60) Provisional application No. 61/601,149, filed on Feb. 21, 2012.

(51) Int. Cl.
| | |
|---|---|
| A61K 38/00 | (2006.01) |
| A61B 3/10 | (2006.01) |
| A61K 9/00 | (2006.01) |
| A61K 9/08 | (2006.01) |
| A61K 31/569 | (2006.01) |
| A61K 38/13 | (2006.01) |
| A61K 45/06 | (2006.01) |
| A61B 3/14 | (2006.01) |

(52) U.S. Cl.
CPC ............ *A61B 3/101* (2013.01); *A61B 3/1025* (2013.01); *A61B 3/14* (2013.01); *A61K 9/0048* (2013.01); *A61K 9/0053* (2013.01); *A61K 9/08* (2013.01); *A61K 31/569* (2013.01); *A61K 38/13* (2013.01); *A61K 45/06* (2013.01)

(58) Field of Classification Search
None
See application file for complete search history.

(56) References Cited

U.S. PATENT DOCUMENTS

| 6,726,680 B1 | 4/2004 | Knopp et al. |
|---|---|---|
| 7,760,927 B2 | 7/2010 | Gholap et al. |
| 7,864,996 B2 | 1/2011 | Hemmer et al. |
| 2006/0188140 A1 | 8/2006 | Gholap et al. |
| 2007/0103693 A1 | 5/2007 | Everett et al. |
| 2007/0206275 A1 | 9/2007 | Hemmer et al. |
| 2010/0057059 A1 | 3/2010 | Makino |
| 2010/0183587 A1 | 7/2010 | Dana et al. |
| 2011/0200242 A1 | 8/2011 | Takama et al. |
| 2011/0274322 A1 | 11/2011 | Kern et al. |
| 2013/0226008 A1 | 8/2013 | Dana et al. |
| 2013/0336557 A1 | 12/2013 | Cruzat et al. |
| 2015/0038851 A1 | 2/2015 | Hamrah et al. |

FOREIGN PATENT DOCUMENTS

| RU | 2330668 | 8/2008 |
|---|---|---|
| WO | 2013/126599 | 8/2013 |
| WO | 2013/126602 | 8/2013 |

OTHER PUBLICATIONS

Al-Arfaj et al., "Significant Narrowing of Corneal Blood Vessel Diameter—A Prominent Neovascular Alteration in Response to Topical Bevacizumab Therapy," PowerPoint presentation at ARVO 2008 (Apr. 27 to May 1, 2008), 30 pages.
Alarfaj et al., "Significant Narrowing of Corneal Blood Vessel Diameter—A Prominent Neovascular Alteration in Response to Topical Bevacizumab Therapy," Oasis, The Online Abstract Submission and Invitation Systems$^{SM}$, Control/Tracking No. 08-A-1311-ARVO (Dec. 6, 2007), 2 pages.
Alhatem, "Peripheral Antigen Presenting Cells Are Differentially Distributed in Normal and Inflamed Murine Corneas," ARVO 2012 Abstract.
Baniasadi et al., "In Vivo Confocal Microscopy for Paecilomyces Lilacinus and Candida Parapsilosis Fungal Keratitis," ARVO 2011 Abstract.
Baniasadi et al., "In Vivo Confocal Microscopy for Paecilomyces Lilacinus and Candida Parapsilosis Fungal Keratitis," ARVO 2011 Poster.
Benitez Del Castillo et al., "An in vivo confocal masked study on corneal epithelium and subbasal nerves in patients with dry eye," Invest Ophthalmol Vis Sci., 45(9):3030-3035 (2004).
Cavalcanti et al., "Contact Lens/Contact Lens solution Combinations Determine the Inflammatory Changes on the Ocular Surface: A Laser in Vivo Confocal Microscopy Study," Abstract (2012).
Cruzat et al., "Diminishment in the Subbasal Corneal Nerve Plexus is Associated with Increased Density of Epithelial Dendritic Cells: An In Vivo Confocal Microscopy Study in Patients with Infectious Keratitis" 2010 ARVO Poster.
Cruzat et al., "Diminishment in the Subbasal Corneal Nerve Plexus is Associated with Increased Density of Epithelial Dendritic Cells: An In Vivo Confocal Microscopy Study in Patients with Infectious Keratitis" 2010 ARVO Abstract.
Cruzat, "In Vivo Confocal Microscopy (IVCM) in Dry Eye: Corneal Epithelial Cell and Nerve Alterations," 2010 AAO Abstract.
Cruzat, "In Vivo Confocal Microscopy in Dry Eye: Corneal Epithelial Cell and Nerve Alterations," AAO 2010 Poster.
Cruzat, "In Vivo Confocal Microscopy in Dry Eye: Corneal Epithelial Cell and Nerve Alterations," AAO, Chicago Presentation (Oct. 16-19, 2010), 10 pages.
Cruzat et al., "Contralateral Clinically Unaffected Eyes of Patients with Unilateral Infectious Keratitis Demonstrate Subclinical Diminishment of Corneal Nerves and Increase Dendritic Cell Density," ARVO 2011 Abstract.

(Continued)

*Primary Examiner* — Jeanette Lieb
(74) *Attorney, Agent, or Firm* — Fish & Richardson P.C.

(57) ABSTRACT

Provided herein are methods of evaluating efficacy of a treatment in a subject having eye inflammation (e.g., a subject having dry eye syndrome) and selecting a subject for participation in a clinical study. Also provided are methods of treating a subject having eye inflammation (e.g., a subject having dry eye syndrome).

18 Claims, 53 Drawing Sheets

(56) References Cited

OTHER PUBLICATIONS

Cruzat et al., "Contralateral Clinically Unaffected Eyes of Patients with Unilateral Infectious Keratitis Demonstrate Subclinical Diminishment of Corneal Nerves and Increase Dendritic Cell Density," ARVO 2011, 16 pages.
Cruzat et al., "Inflammation and the Nervous System: The Connection in the Cornea in Patients with Infectious Keratitis," Investigative Ophthalmology & Visual Science, 52(8):5136-5143 (2011).
Dastjerdi et al., "Corneal sensation and morphology of corneal nerves in herpes zoster ophthalmicus: an in vivo confocal microscopy study," 2007 Abstract, 1 page.
Dastjerdi et al., "Corneal Sensation and Morphology of Corneal Nerves in Herpes Zoster Ophthalmicus," PowerPoint presentation at ARVO 2007 (May 6-10, 2007), 22 pages.
Dastjerdi et al., "Disparate Corneal Nerve Alterations between the Two Eyes in Dry Eye Patients with Asymmetric Ocular Surface Manifestations: In Vivo Confocal Microscopy Study," Oasis, The Online Abstract Submission and Invitation Systems$^{SM}$, Control/Tracking No. 08-A-3724-ARVO (Dec. 6, 2007), 2 pages.
Dastjerdi et al., "Disparate Corneal Nerve Changes among Fellow Eyes of Patients with Asymmetric Dry Eye Disease: In Vivo Confocal Microscopy Study," Oasis, The Online Abstract Submission and Invitation Systems$^{SM}$, Control/Tracking No. 08-PP-30019585-AAO (Apr. 9, 2008), 2 pages.
Ghafournian et al., "In Vivo Confocal Microscopy Study of Epithelial Cell Changes and Nerve Alterations in Patients with Dry Eye Syndrome," Poster (2009).
Ghafournian et al., "In Vivo Confocal Microscopy Study of Epithelial Cell Changes and Nerve Alterations in Patients with Dry Eye Syndrome," Abstract (2009).
Hamrah et al., "Novel Characterization of MHC Class II—Negative Population of Resident Corneal Langerhans Cell-Type Dendritic Cells," Invest. Ophthalmol. Vis. Sci. 43:639-646 (2002).
Hamrah et al., "The Corneal Stroma is Endowed with a Significant Number of Resident Dendritic Cells," Invest. Ophthalmol. Vis. Sci., 44:581-589 (2003).
Hamrah et al., "Alterations in Corneal Stromal Dendritic Cell Phenotype and Distribution in Inflammation," Arch. Ophthalmol., 121:1132-1140 (2003).
Hamrah et al., "Comparison of Corneal Nerve Alterations and Corneal Sensitivity in Herpes Simplex Keratitis With In Vivo Confocal Microscopy," ARVO Abstract, Control #07-A-4430-ARVO (Dec. 20, 2006), 3 pages.
Hamrah et al., "#774 Comparison of Corneal Nerve Alterations and Corneal Sensitivity in Herpes Simplex Keratitis with In Vivo Confocal Microscopy," ARVO 2007 Poster.
Hamrah et al., "Deletion of Chemokine Receptor CCR1 Prolongs Corneal Survival," Invest. Ophthalmol. Vis. Sci., 48:1228-1236 (2007).
Hamrah et al., "Cellular Changes of the Cornea in Herpes Zoster Ophthalmicus: An In Vivo Confocal Microscopy Study," ARVO Abstract, Control/Tracking No. 08-A-2436-ARVO (2007), 2 pages.
Hamrah et al., "Cellular Changes of the Cornea in Herpes Zoster Ophthalmicus: An In Vivo Confocal Microscopy Study," ARVO 2008 Presentation (Apr. 27 to May 1, 2008), 24 pages.
Hamrah et al., "Cellular Changes of the Cornea in Herpes Zoster Ophthalmicus: An In Vivo Confocal Microscopy Study," ARVO 2008 Abstract.
Hamrah et al., "Corneal Epithelial and Stromal Changes in Patients with Herpes Simplex Keratitis: an In Vivo Confocal Microscopy Study," Abstract, Control/Tracking No. 09-A-977-ARVO (Nov. 27, 2008), 2 pages.
Hamrah et al., "Corneal Epithelial and Stromal Changes in Patients with Herpes Simplex Keratitis: an In Vivo Confocal Microscopy Study" ARVO 2009 Abstract.
Hamrah et al., "Corneal Epithelial and Stromal Changes in Patients with Herpes Simplex Keratitis: an In Vivo Confocal Microscopy Study #2389," ARVO 2009 Poster.
Hamrah, "In Vivo Confocal Microscopy of the Cornea in Health and Disease," Harvard Medical School Presentation 2009, 48 pages.
Hamrah, "In Vivo Imaging and Quantification of Corneal Inflammation," WOC 2010, Berlin, Germany, 5 pages.
Hamrah et al., Visualization of Corneal Antigen—Presenting Cell Migration by Multi-Photon Intravital Microscopy (2010), 32 pages.
Hamrah, "In Vivo Imaging of Corneal Nerves," New Frontiers in Corneal Research Presentation, May 2010, 89 pages.
Hamrah, "Corneal Imaging," University of Louisville Presentation, Sep. 17, 2010, 105 pages.
Hamrah, "Immunobiology of Corneal Graft Rejection," Emory Eye Center Presentation Dec. 17, 2010, 110 pages.
Hamrah et al. "Antigen-Presenting Cells in the Eye and Ocular Surface," In Encyclopedia of the Eye, Oxford: Academic Press, 1:120-127 (2010).
Hamrah et al., "Corneal Sensation and Subbasal Nerve Alterations in Patients with Herpes Simplex Keratitis," Ophthalmology, 117:1930-1936 (2010).
Hamrah et al., "Physiologic Homeostasis and Turnover of Corneal Bone Marrow-Derived Cells: Lessons from the Parabiosis Model," ARVO 2011 Poster.
Hamrah, "The Evolving Story of Corneal Antigen Presenting Cells: From Bench to Bedside," Duke Presentation Feb. 25, 2011, 121 pages.
Hamrah et al., "In vivo Imaging of Inflammatory Cell-Vessel Interactions at the Ocular Surface," ARVO 2011 Meeting (May 2011), 33 pages.
Hamrah, "Immuno-Imaging of the Ocular Surface: Studying Immune System Dynamics In Vivo," Duke Presentation May 18, 2011, 150 pages.
Hamrah, "An Explanation for Refractory Dry Eye Symptoms Despite Significant Improvement in Dry Eye Signs Post-Treatment for Meibomian Gland Dysfunction," AAOPT Abstract 2011.
Hamrah, "An Explanation for Refractory Dry Eye Symptoms Despite Significant Improvement in Dry Eye Signs Post-Treatment for Meibomian Gland Dysfunction," AAOPT Presentation, Oct. 2011, 38 pages.
Hamrah et al., "Cellular Changes of the Corneal Epithelium and Stroma in Herpes Simplex Keratitis: An In Vivo Confocal Microscopy Study," Ophthalmology, 119(9):1791-1797 (2012).
Hamrah et al., "Unilateral Herpes Zoster Ophthalmicus Results in Bilateral Corneal Nerve Alteration: An In Vivo Confocal Microscopy Study," Ophthalmology, 120(1):40-47 (2013).
Hoesl et al., "Cellular and Subbasal Nerve Alterations in Fuchs' Endothelial Dystrophy: An in vivo Confocal Microscopy Study," Abstract, ARVO (Nov. 28, 2008).
Hoesl et al., "Cellular and Subbasal Nerve Alterations in Fuchs' Endothelial Dystrophy: An in vivo Confocal Microscopy Study," ARVO 2009 Poster.
Hu et al., "Conjunctival in vivo confocal scanning laser microscopy in patients with atopic keratoconjunctivitis," Molecular Vision, 13:1379-89 (2007).
Hu et al., Infection of the Cornea with Herpes Simplex Virus-1 Results in Immediate Destruction of Subbasal Corneal Nerves and Increased Density and Maturation of Corneal Antigen-Presenting Cell, ARVO 2011 Abstract.
Hu et al., Infection of the Cornea with Herpes Simplex Virus-1 Results in Immediate Destruction of Subbasal Corneal Nerves and Increased Density and Maturation of Corneal Antigen-Presenting Cell, ARVO 2011 Poster.
International Search Report and Written Opinion for App. Ser. No. PCT/US2013/027181, dated Jun. 20, 2013, 8 pages.
Kurbanyan et al., "Corneal Nerve Alterations in Acute Acanthamoeba and Fungal Keratitis: An in vivo Confocal Microscopy Study," ARVO 2009 Abstract.
Kurbanyan et al., "#D709 Corneal Nerve Alterations in Acute Acanthamoeba and Fungal Keratitis: An in Vivo Confocal Microscopy Study," ARVO 2009 Poster.
Kurbanyan et al., "Corneal Nerve Alterations in Acute Acanthamoeba and Fungal Keratitis: An In Vivo Confocal Microscopy Study," Eye, 1-7 (2011).

(56) References Cited

OTHER PUBLICATIONS

Kurbanyan et al., "Corneal Nerve Alterations in Acute Acanthamoeba and Fungal Keratitis: An In Vivo Confocal Microscopy Study," Eye, 26:126-132 (2012).
Le et al., "In Vivo Confocal Microscopy of Long-standing Mixed-form Vernal Keratoconjunctivitis," Ocular Immunology & Inflammation, 18(5):349-351 (2010).
Le et al., "In vivo laser scanning confocal microscopy of vernal keratoconjunctivitis," Clinical and Experimental Ophthalmology, 39:53-60 (2011).
Lee et al., "In Vivo Confocal Microscopy in Diagnosis and Management of Acanthamoeba Keratitis Improves Patient Outcome," ARVO 2010 Abstract.
Lee et al., "In Vivo Confocal Microscopy in Diagnosis and Management of Acanthamoeba Keratitis Improves Patient Outcome," ARVO 2010 Poster.
Lee et al., "Diagnosis and Management of Acanthamoeba Keratitis by In Vivo Confocal Microscopy Improves Outcomes," ARVO 2010, 14 pages.
Lee et al., "Diagnosis and Management of Acanthamoeba Keratitis by In Vivo Confocal Microscopy Improves Outcomes," ARVO 2010 Abstract.
Mantopoulos et al., "P- and E-Selectins Mediate Dendritic Cell Homing to the Cornea," ARVO 2010 Abstract.
Mantopoulos et al., "P- and E-Selectins Mediate Dendritic Cell Homing to the Cornea," ARVO 2010 Poster.
Qazi et al., "Early Effects of Contact Lens Wear on Immune Cell Density of the Ocular Surface: Preliminary Results of a Laser In Vivo Confocal Microscopy Study," ARVO 2011 Abstract.
Qazi et al., "Early Effects of Contact Lens Wear on Immune Cell Density of the Ocular Surface: Preliminary Results of a Laser In Vivo Confocal Microscopy Study," ARVO 2011 Poster.
Schneider, "The Appearance of Hyper-Reflective Superficial Epithelial Cells Observed Using in vivo Confocal Microscopy," A thesis presented to the University of Waterloo. Waterloo, Ontario, Canada, 2010. Retrieved from the Internet: <URL: http://libdspace.uwaterloo.ca/4983/1/Schneider_Simone.pdf> abstract, pp. 41, 185, 207.
Schrems et al., "In Vivo Confocal Microscopy Comparison of the Anterior Human Corneal Structures by Laser Scanning and White Light Systems in Normal Diseased Corneas," ARVO 2009 Poster.
Shahatit et al., "#D975 In Vivo Morphology of Corneal Nerves in Patients with Corneal Allodynia," ARVO 2009 Poster.
Shahatit et al., In Vivo Morphology of Corneal Nerves in Patients with Corneal Allodynia, ARVO 2009 Abstract.
Turhan et al., "Dendritic Cell Recruitment to the Cornea is Differentially Regulated in Steady State and Inflammation," ARVO 2011 Meeting Abstract.
Turhan et al., "Dendritic Cell Recruitment to the Cornea is Differentially Regulated in Steady State and Inflammation," ARVO 2011 Poster.
Yamagami et al., "Distinct populations of dendritic cells in the normal human donor corneal epithelium," Invest Ophthalmol Vis Sci., 46(12):4489-4494 (2005).
Zheng et al., "Identification of Novel Subsets of Plasmacytoid and Conventional Dendritic Cells in the Cornea," ARVO 2010 Meeting Poster.
Zheng et al., "Identification of Novel Subsets of Plasmacytoid and Conventional Dendritic Cells in the Cornea," ARVO 2010 Meeting Abstract.
Office Action issued in U.S. Appl. No. 13/971,609 dated Dec. 2, 2014, 79 pages.
Notice of Allowance issued in U.S. Appl. No. 13/971,609 dated Jul. 8, 2015, 13 pages.
Kheirkhah et al., "Autologous Serum Tears May Result in Subclinical Changes in Corneal Immunity: An In Vivo Confocal Microscopy Study," Investigative Ophthalmology & Visual Science Jun. 2013, vol. 54, 978, Abstract, 1 page.
You et al., "Laser in Vivo Confocal Microscopy Demonstrates a Lower Density of Peripheral Corneal Nerve Fibers Compared to the Central Cornea in Normal Subjects," Investigative Ophthalmology & Visual Science Jun. 2013, vol. 54, 531, Abstract, 1 page.
Colon et al., "Morphologic Dendritic Immune Cells Parameters Reveal Differential Characteristics between the Central and Peripheral Cornea: an In Vivo Confocal Microscopy Normative Data," Investigative Ophthalmology & Visual Science Jun. 2013, vol. 54, 2063, Abstract 1 page.
Cavalcanti et al., "In Vivo Confocal Microscopy Demonstrates Bilateral Increase in Epithelial Corneal Dendritic Immune Cells in Unilateral Herpes Zoster Ophthalmicus," Investigative Ophthalmology & Visual Science Jun. 2013, vol. 54, 2159, Abstract, 1 page.
Hamrah et al., "An explanation for refractory dry eye symptoms despite significant improvement in dry eye signs post-treatment for meibomian gland dysfunction (MGD)," American Academy of Optometry, Program No. 110010, Oct. 2011, Abstract, 1 page.
Colon et al, "In Vivo Confocal Microscopy of the Immune Cells in the Cornea of Normal Subjects Demonstrates Irregular Peripheral Distribution of Dendritic Cells," Investigative Ophthalmology & Visual Science Mar. 2012, vol. 53, 94, Poster, 1 page.
Williams et al., "In Vivo Confocal Microscopy as a Tool to Evaluate Cellular Changes in the Cornea and Conjunctiva in Ocular Allergy and Non-Allergic Ocular Inflammatory Diseases," Conjunctiva: Biology and Pathophysiology, May 8, 2012, Poster, 1 page.
Vora et al., "In Vivo Confocal Microscopy Analysis and Image-Guided Therapy of Limbal Stem Cell Insufficiency," Corneal Stem Cells II May 8, 2012, Poster, 1 page.
Trinidad et al., "Epithelial Immune Cell Alterations and the Effect of Anti-Inflammatory Treatment in Patients with Dry Eye Syndrome: An In Vivo Confocal Microscopy Study," Investigative Ophthalmology & Visual Science Mar. 2012, vol. 53, 584, Poster, 1 page.
Hamrah et al., "An Explanation for Refractory Dry Eye Symptoms Despite Significant Improvement in Dry Eye Signs Post-Treatment for Meibomian Gland Dysfunction," American Academy of Optometry, Program No. 110010, Oct. 2011, Poster, 1 page.
Yao et al., "Dry Eye Syndrome: An Update in Office Management" Am. J. Med. 124:1016-1018, 2011.
Girish et al., "Affordable image analysis using NIH Image/ImageJ," Indian J. Cancer 41(1):47, 2004.
Meijering et al., "Design and validation of a tool for neurite tracing and analysis in fluorescence microscopy images," Cytometry Part A, 58A(2):167-176, Apr. 2004.
Oliveira-Soto and Efron, "Morphology of corneal nerves using confocal microscopy," Cornea 20(4):374-384, May 2001.
Ibrahim et al., "The efficacy, sensitivity, and specificity of in vivo laser confocal microscopy in the diagnosis of meibomian gland dysfunction," Ophthalmology, 117(4):665-672, Apr. 2010.
Geerling et al., "The International Workshop on Meibomian Gland Dysfunction: Report of the Subcommittee on Management and Treatment of Meibomian Gland Dysfunction," Investigative Ophthalmology & Visual Science, 52(4):2050-2064 (Special Issue, 2011).
Asbell et al., "The International Workshop on Meibomian Gland Dysfunction: Report of the Clinical Trials Subcommittee," Investigative Ophthalmology & Visual Science, 52(4):2065-2085 (Special Issue, 2011).
International Search Report and Written Opinion issued in PCT/US2013/027177 dated Jul. 11, 2013 (8 pages).
Em et al., "In vivo confocal microscopy in blepharitis," Klin Monbl Augenheilkd, 222(11):894-900 (2005) (Abstract).
International Preliminary Report on Patentability issued in PCT/US2013/027177 dated Aug. 26, 2014 (6 pages).

Normal Subject  Acute Allergy

FIG. 42A
FIG. 42B
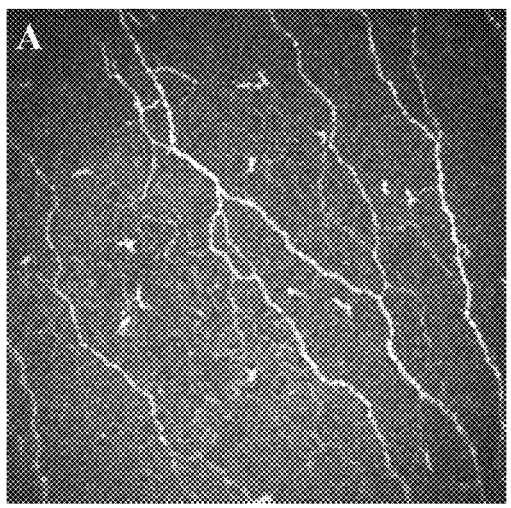
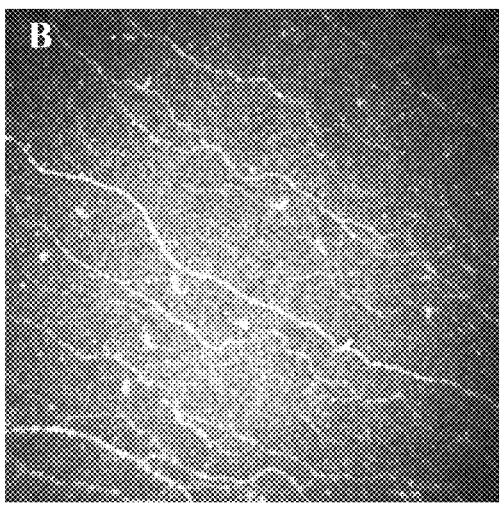
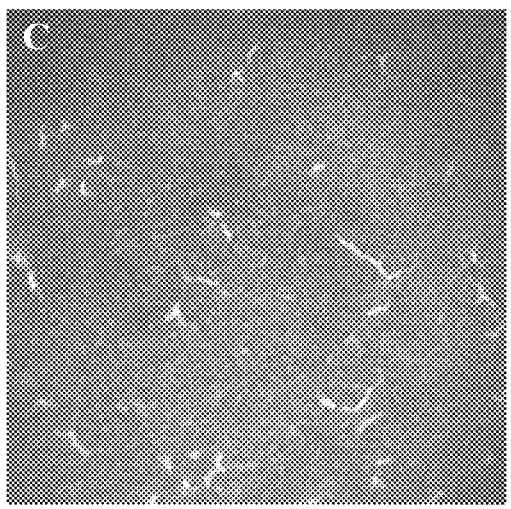
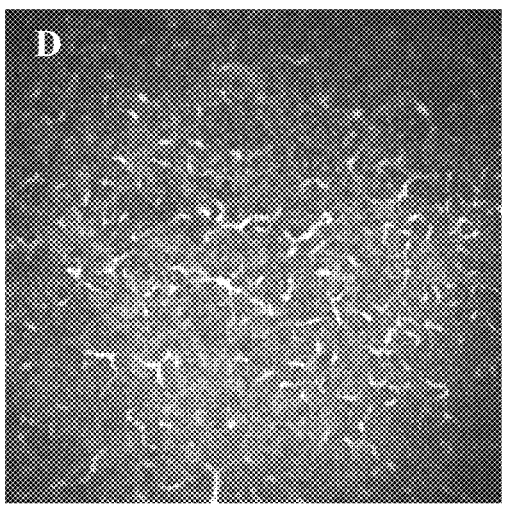
FIG. 42C
FIG. 42D

Pre-treatment      3 months on treatment

Pre-treatment      3 months on treatment

INFLAMMATORY EYE DISORDERS

CLAIM OF PRIORITY

This application is a continuation of U.S. patent application Ser. No. 14/379,380, filed on Aug. 18, 2014, which is a U.S. national stage under 35 U.S.C. § 371 of International Patent Application Number PCT/US2013/027181, filed on Feb. 21, 2013, which claims priority to U.S. Provisional Patent Application Ser. No. 61/601,149, filed on Feb. 21, 2012. The entire contents of the foregoing are incorporated by reference.

FEDERALLY SPONSORED RESEARCH

This invention was made with Government support under grant number NIH K12-EY016335 and NIH K08-EY020575 awarded by the National Institutes of Health. The Government has certain rights in the invention.

BACKGROUND OF THE INVENTION

Eye inflammation is common and occurs in humans of all ages. It can last from a few minutes to years, depending on the type and severity of the underlying disease, disorder, or condition. Non-limiting causes of eye inflammation include infection (e.g., bacterial, fungal, viral, or parasitic infection), allergy, autoimmune disorders (e.g., ankylosing spondylitis, Behcet's syndrome, dermatomyositis, Graves' disease, juvenile rheumatoid arthritis, multiple sclerosis, psoriatic arthritis, Reiter's syndrome, rheumatoid arthritis, Sjogren's syndrome, systemic lupus erythematosus, and Wegener's granulatomatosis), dry eye syndrome, irritation, and injury or trauma to the eye or eyelid.

Dry eye syndrome is one of the most common eye problems affecting the general population. Dry eye syndrome can cause problems that range in severity from mildly irritating to debilitating. In healthy subjects, the eye produces a tear film that covers and protects the surface of the eye. The tear film is normally a stable, homogenous layer that provides the cornea and conjunctiva with protection from the air. Patients with dry eye syndrome lack a sufficient tear film (e.g., lack of tears and/or unstable tears) on some surfaces on the cornea and conjunctiva that leads to symptoms of irritation and changing vision. Patients having eye inflammation (e.g., subjects having dry eye syndrome) are commonly prescribed artificial tears, an oral antibiotic, and/or cyclosporine, and occasionally short-term use of steroids.

SUMMARY OF THE INVENTION

The invention is based, in part, on the discovery that efficacy of treatment of eye inflammation or dry eye syndrome in a subject correlates with changes in one or more of the following ocular physical features that can be determined (e.g., using in vivo confocal microscopy): (i) a decrease in the number or percentage of hyperreflective superficial epithelial cells present in the cornea (e.g., in the center of the cornea), (ii) a decrease in the average size of superficial epithelial cells present in the cornea (e.g., in the center of the cornea), (iii) an elevation in the density of superficial epithelial cells present in the cornea (e.g., in the center of the cornea), (iv) a decrease in the density of dendritic immune cells present in the cornea (e.g., in the center of the cornea), (v) a decrease in the average size of dendritic immune cells present in the cornea (e.g., in the center of the cornea), (vi) a decrease in the average area covered by dendritic immune cells present in the cornea (e.g., in the center of the cornea), (vii) an elevation in the density or average length of nerves present in the cornea, (viii) an elevation in the amount of branching in nerves present in the cornea, and (ix) an elevation in the total number of nerves present in the cornea (e.g., as compared to the corresponding levels in the subject prior to treatment or at an earlier time point in treatment). The invention is also based, in part, on the discovery that subjects having eye inflammation (e.g., allergy, limbal stem cell insufficiency, or graft versus host disease) have specific ocular physical features (e.g., the number and/or average density of dendritic inflammatory cells present in the peripheral cornea), that can be determined (e.g., using in vivo confocal microscopy), and can be used to select a therapy.

In view of these discoveries, provided herein are methods of evaluating efficacy of a treatment in a subject having eye inflammation (e.g., a subject having dry eye syndrome, a subject having limbal stem cell deficiency, or a subject having graft versus host disease) and selecting a subject for participation in a clinical study. These methods require determining in an eye of a subject or obtaining (or reviewing previously obtained or recorded) medical information for the subject regarding one or more of (i) the number or percentage of hyperreflective superficial epithelial cells present in the cornea (e.g., in the center of the cornea), (ii) the average size of superficial epithelial cells present in the cornea (e.g., in the center of the cornea), (iii) the density of superficial epithelial cells present in the cornea (e.g., in the center of the cornea), (iv) the density of dendritic immune cells present in the cornea (e.g., in the center of the cornea), (v) the average size of dendritic immune cells present in the cornea (e.g., in the center of the cornea), (vi) the average area covered by dendritic immune cells present in the cornea (e.g., in the center of the cornea), (vii) the density or average length of nerves present in the cornea, (viii) the amount of branching in nerves present in the cornea, and (ix) the total number of nerves present in the cornea. In some embodiments, the determining is performed using in vivo confocal microscopy. In these methods one or more of the following ocular physical features indicates that the treatment was effective in the subject: (i) a decrease in the number or percentage of hyperreflective superficial epithelial cells present in the center of the cornea, (ii) a decrease in the average size of superficial epithelial cells present in the cornea (e.g., in the center of the cornea), (iii) an elevation in the density of superficial epithelial cells present in the cornea (e.g., in the center of the cornea), (iv) a decrease in the density of dendritic immune cells present in the cornea (e.g., in the center of the cornea), (v) a decrease in the average size of dendritic immune cells present in the cornea (e.g., in the center of the cornea), (vi) a decrease in the average area covered by dendritic immune cells present in the cornea (e.g., in the center of the cornea), (vii) an elevation in the density or average length of nerves present in the cornea, (viii) an elevation in the amount of branching in nerves present in the cornea, and (ix) an elevation in the total number of nerves present in the cornea (e.g., as compared to the corresponding levels in the subject prior to treatment or at an earlier time point in treatment). Some embodiments further include identifying the treatment administered to a subject having an eye with one or more of the following (i) a decrease in the number or percentage of hyperreflective superficial epithelial cells present in the center of the cornea, (ii) a decrease in the average size of superficial epithelial cells present in the cornea (e.g., in the center of the cornea), (iii) an elevation in the density of superficial epithelial cells present in the cornea (e.g., in the center of the cornea), (iv) a decrease in the density of dendritic immune cells present in the cornea (e.g., in the center of the cornea), (v) a decrease in the average size of dendritic immune cells present in the cornea (e.g., in the center of the cornea), (vi) a decrease in the average area covered by dendritic immune cells present in the cornea (e.g., in the center of the cornea), (vii) an elevation in the density or average length of nerves present in the cornea, (viii) an elevation in the amount of branching in nerves present in the cornea, and (ix) an elevation in the total number of nerves present in the cornea (e.g., as compared to the corresponding levels in the subject prior to treatment or at an earlier time point in treatment) as being effective in the subject.

Also provided are methods of treatment that include selectively administering to an eye(s) of a subject having dry eye syndrome, determined to have an elevated density of dendritic immune cells present in the center of the cornea as compared to a reference level, a topical steroid solution; or selectively topically or orally administering to a subject having dry eye syndrome, determined to have a substantially the same or a decreased density of dendritic immune cells present in the center of the cornea as compared to a reference level, at least two immunosuppressive agents. Also provided are methods of using a topical steroid solution for treating a subject having dry eye syndrome determined to have an elevated density of dendritic immune cells present in the center of the cornea as compared to a reference level. Also provided herein are a topical steroid solution for use in treating a subject having dry eye syndrome determined to have an elevated density of dendritic immune cells present in the center of the cornea as compared to a reference level and/or for use in the manufacture of a medicament for treating dry eye syndrome in a subject (e.g., for treating dry eye syndrome in a subject determined to have an elevated density of dendritic immune cells present in the center of the cornea as compared to a reference level). Also provided are methods of using at least two immunosuppressive agents (e.g., formulated for topical or oral administration) for treating a subject having dry eye syndrome determined to have substantially the same or a decreased density of dendritic immune cells present in the center of the cornea as compared to a reference level. Also provided are at least two immunosuppressive agents (e.g., formulated for topical or oral administration) for use in treating a subject having dry eye syndrome determined to have substantially the same or a decreased density of dendritic immune cells present in the center of the cornea as compared to a reference level and/or for use in the manufacture of a medicament for treating dry eye syndrome in a subject (e.g., for treating dry eye syndrome in a subject determined to have substantially the same or a decreased density of dendritic immune cells present in the center of the cornea as compared to a reference level).

Also provided are methods of treating a subject that include selectively topically and/or orally administering to a subject, determined to have an elevated number or elevated average density of dendritic inflammatory cells present in the peripheral cornea as compared to a corresponding reference value, at least one anti-inflammatory steroid and/or at least one immunosuppressive agent (e.g., at least one calcineurin inhibitor). Also provided are methods of using at least one anti-inflammatory steroid and/or at least one immunosuppressive agent (e.g., at least one calcineurin inhibitor) (e.g., formulated for topical and/or oral administration) for treating a subject determined to have an elevated number or elevated average density of dendritic inflammatory cells present in the peripheral cornea as compared to a corresponding reference value. Also provided are at least one anti-inflammatory steroid and/or at least one immunosuppressive agent (e.g., at least one calcineurin inhibitor) (e.g., formulated for topical and/or oral administration) for use in treating a subject determined to have an elevated number or elevated average density of dendritic inflammatory cells present in the peripheral cornea as compared to a corresponding reference value and/or for use in the manufacture of a medicament for treating a subject determined to have an elevated number or elevated average density of dendritic inflammatory cells present in the peripheral cornea as compared to a corresponding reference value.

Also provided are methods of selecting a subject for participation in a clinical study that include determining in an eye of a subject or obtaining (or reviewing previously obtained or recorded) medical information for the subject regarding the number or average density of dendritic inflammatory cells present in the peripheral cornea. In some embodiments, the determining is performed using in vivo confocal microscopy.

Provided herein are methods of evaluating efficacy of a treatment in a subject having eye inflammation (e.g., a subject having dry eye syndrome, a subject having allergy, a subject having limbal stem cell deficiency, or a subject having graft versus host disease) that include: (a) determining in an eye of a subject having eye inflammation (e.g., a subject having dry eye syndrome, a subject having allergy, a subject having limbal stem cell deficiency, or a subject having graft versus host disease), or alternatively obtaining, providing, or using previously determined information regarding, one or more of (i) the number or percentage of hyperreflective superficial epithelial cells present in the cornea, (ii) the average size of superficial epithelial cells present in the cornea, (iii) the density of superficial epithelial cells present in the cornea, (iv) the density of dendritic immune cells present in the cornea, (v) the average size of dendritic immune cells present in the cornea, (vi) the average area covered by dendritic immune cells present in the cornea, (vii) the density or average length of nerves present in the cornea, (viii) the amount of branching in nerves present in the cornea, and (ix) the total number of nerves present in the cornea at a first time point; (b) determining in the eye of the subject, or alternatively obtaining, providing, or using previously determined information regarding, one or more of (i) the number or percentage of hyperreflective superficial epithelial cells present in the cornea, (ii) the average size of superficial epithelial cells present in the cornea, (iii) the density of superficial epithelial cells present in the cornea, (iv) the density of dendritic immune cells present in the cornea, (v) the average size of dendritic immune cells present in the cornea, (vi) the average area covered by dendritic immune cells present in the cornea, (vii) the density or average length of nerves present in the cornea, (viii) the amount of branching in nerves present in the cornea, and (ix) the total number of nerves present in the cornea at a second time point; and (c) comparing the one or more of (i) the number or percentage of hyperreflective superficial epithelial cells present in the cornea, (ii) the average size of superficial epithelial cells present in the cornea, (iii) the density of superficial epithelial cells present in the cornea, (iv) the density of dendritic immune cells present in the cornea, (v) the average size of dendritic immune cells present in the cornea, (vi) the average area covered by dendritic immune cells present in the cornea, (vii) the density or average length of nerves present in the cornea, (viii) the amount of branching in nerves present in the cornea, and (ix) the total number of nerves present in the cornea determined at the first and second time points, where (i) the first time point is prior to treatment and the second time point is any time point following the initiation of treatment, or (ii) the first time point is following the initiation of treatment and the second time point is at a later time point during or after treatment; and one or more of a decrease in the number or percentage of hyperreflective superficial epithelial cells present in the cornea, a decrease in the average size of superficial epithelial cells present in the cornea, an elevation in the density of superficial epithelial cells present in the cornea, a decrease in the density of dendritic immune cells present in the cornea, a decrease in the average size of dendritic immune cells present in the cornea, a decrease in the average area covered by dendritic immune cells present in the cornea, an elevation in the density or average length of nerves present in the cornea, an elevation in the amount of branching in nerves present in the cornea, and an elevation in the total number of nerves present in the cornea determined at the second time point compared to the first time point indicates that the treatment was effective in the subject, and optionally, further including (d) identifying the treatment administered to a subject having in an eye one or more of a decrease in the number or percentage of hyperreflective superficial epithelial cells present in the cornea, a decrease in the average size of superficial epithelial cells present in the cornea, an elevation in the density of superficial epithelial cells present in the cornea, a decrease in the density of dendritic immune cells present in the cornea, a decrease in the average size of dendritic immune cells present in the cornea, a decrease in the average area covered by dendritic immune cells present in the cornea, an elevation in the density or average length of nerves present in the cornea, an elevation in the amount of branching in nerves present in the cornea, and an elevation in the total number of nerves present in the cornea determined at the second time point compared to the first time point, as being effective in the subject. In some embodiments, the superficial epithelial cells are present in the center of the cornea. In some embodiments, the dendritic immune cells are present in the center of the cornea. In some embodiments, the determining in (a) and (b) is performed using in vivo confocal microscopy.

Some embodiments further include assessing, or alternatively obtaining, providing, or using previously determined information regarding, one or more symptoms of dry eye syndrome in the subject at the first and second time point. In some embodiments, one or more of (i) the number or percentage of hyperreflective superficial epithelial cells present in the cornea, (ii) the average size of superficial epithelial cells present in the cornea, and (iii) the density of superficial epithelial cells present in the cornea is determined in the subject or obtained (e.g., obtained from previously recorded medical information) for the subject, at the first and second time points. In some embodiments, one or more of (iv) the density of dendritic immune cells present in the cornea, (v) the average size of dendritic immune cells present in the cornea, (vi) the average area covered by dendritic immune cells present in the cornea is determined in the subject, or alternatively obtaining, providing, or using previously determined information regarding, at the first and second time points. In some embodiments, one or more of (vii) the density or average length of nerves present in the cornea, (viii) the amount of branching in nerves present in the cornea, and (ix) the total number of nerves present in the cornea is determined in the subject, or alternatively obtained or provided from or using previously determined information for the subject, at the first and second time points.

Some embodiments further include administering to the subject a treatment for eye inflammation (e.g., a treatment for dry eye syndrome). In some embodiments, the subject is a participant in a clinical trial.

Also provided are methods of selecting a subject for participation in a clinical study that include: (a) determining in an eye of a subject, or alternatively obtaining, providing, or using previously determined information regarding, one or more of (i) the number or percentage of hyperreflective superficial epithelial cells present in the cornea, (ii) the average size of superficial epithelial cells present in the cornea, (iii) the density of superficial epithelial cells present in the cornea, (iv) the density of dendritic immune cells present in the cornea, (v) the average size of dendritic immune cells present in the cornea, (vi) the average area covered by dendritic immune cells present in the cornea, (vii) the density or average length of nerves present in the cornea, (viii) the amount of branching in nerves present in the cornea, and (ix) the total number of nerves present in the cornea; (b) comparing the one or more of (i) the number or percentage of hyperreflective superficial epithelial cells present in the cornea, (ii) the average size of superficial epithelial cells present in the cornea, (iii) the density of superficial epithelial cells present in the cornea, (iv) the density of dendritic immune cells present in the cornea, (v) the average size of dendritic immune cells present in the cornea, (vi) the average area covered by dendritic immune cells present in the cornea, (vii) the density or average length of nerves present in the cornea, (viii) the amount of branching in nerves present in the cornea, and (ix) the total number of nerves present in the cornea, determined in the eye of the subject to one or more corresponding reference values; and (c) selecting a subject having one or more of (i) an elevation in the number or percentage of hyperreflective superficial epithelial cells present in the cornea, (ii) an elevation in the average size of superficial epithelial cells present in the cornea, (iii) a decrease in the density of superficial epithelial cells present in the cornea, (iv) an elevation in the density of dendritic immune cells present in the cornea, (v) an elevation in the average size of dendritic immune cells present in the cornea, (vi) an elevation in the average area covered by dendritic immune cells present in the cornea, (vii) a decrease in the density or average length of nerves present in the cornea, (viii) a decrease in the amount of branching in nerves present in the cornea, and (ix) a decrease in the total number of nerves present in the cornea, compared to the one or more corresponding reference values for participation in a clinical study. In some embodiments, the superficial epithelial cells are present in the center of the cornea. In some embodiments, the dendritic immune cells are present in the center of the cornea. In some embodiments, the determining in (a) is performed using in vivo confocal microscopy.

In some embodiments, the one or more corresponding reference values are threshold values. In some embodiments, the one or more corresponding reference values are one or more of (i) the number or percentage of hyperreflective superficial epithelial cells present in the cornea, (ii) the average size of superficial epithelial cells present in the cornea, (iii) the density of superficial epithelial cells present in the cornea, (iv) the density of dendritic immune cells present in the cornea, (v) the average size of dendritic immune cells present in the cornea, (vi) the average area covered by dendritic immune cells present in the cornea, (vii) the density or average length of nerves present in the cornea, (viii) the amount of branching in nerves present in the cornea, and (ix) the total number of nerves present in the cornea, determined in (or recorded or previously observed for) the eye of a healthy subject. In some embodiments, the one or more corresponding reference values are determined using in vivo confocal microscopy. In some embodiments, the reference value is determined in a cohort of reference subjects. In some embodiments, the reference value is statistically determined in a cohort of reference subjects, e.g., is the median, mean, or a percentile (e.g., tertile, quartile, or quintile) cut-off value (e.g., the top percentile, e.g., top tertile, quartile, or quintile cut-off value) in a cohort of reference subjects.

In some embodiments, the subject is diagnosed as having dry eye syndrome. In some embodiments, the subject has limbal stem cell deficiency and/or graft versus host disease.

In some embodiments, one or more of (i) the number or percentage of hyperreflective superficial epithelial cells present in the cornea, (ii) the average size of superficial epithelial cells present in the cornea, (iii) the density of superficial epithelial cells present in the cornea is determined in the subject or obtained (e.g., obtained from previously recorded medical information) for the subject. In some embodiments, one or more of (iv) the density of dendritic immune cells present in the cornea, (v) the average size of dendritic immune cells present in the cornea, (vi) the average area covered by dendritic immune cells present in the cornea is determined in the subject or obtained (e.g., obtained from previously recorded medical information) for the subject. In some embodiments, one or more of vii) the density or average length of nerves present in the cornea, (viii) the amount of branching in nerves present in the cornea, and (ix) the total number of nerves present in the cornea is determined in the subject or obtained (e.g., obtained from previously recorded medical information) for the subject.

Also provided are methods of treating a subject having dry eye syndrome that include selectively administering to an eye(s) of a subject having dry eye syndrome, determined to have an elevated number or density of dendritic immune cells present in the center of the cornea as compared to a reference level, a topical steroid solution; or selectively orally or topically administering to a subject having dry eye syndrome, determined to have no substantial change or a decreased number or density of dendritic immune cells present in the center of the cornea as compared to a reference level, two or more immunosuppressive agents. Also provided are methods of using a topical steroid solution for treating a subject having dry eye syndrome determined to have an elevated number or density of dendritic immune cells present in the center of the cornea as compared to a reference level. Also provided are topical steroid solutions for use in treating a subject having dry eye syndrome determined to have an elevated number or density of dendritic immune cells present in the center of the cornea as compared to a reference level and/or for use in the manufacture of a medicament for treating dry eye syndrome in a subject (e.g., for treating dry eye syndrome in a subject determined to have an elevated number or density of dendritic immune cells present in the center of the cornea as compared to a reference level. Also provided are methods of using two or more immunosuppressive agents (e.g., formulated for oral or topical administration) for treating a subject having dry eye syndrome determined to have an elevated number or density of dendritic immune cells present in the center of the cornea as compared to a reference level. Also provided are two or more immunosuppressive agents (e.g., formulated for oral or topical administration) for use in treating a subject having dry eye syndrome determined to have an elevated number or density of dendritic immune cells present in the center of the cornea as compared to a reference level and/or for use in the manufacture of a medicament for treating dry eye syndrome in a subject (e.g., for treating dry eye syndrome in a subject determined to have an elevated number or density of dendritic immune cells present in the center of the cornea as compared to a reference level.

In some embodiments, the topical steroid solution contains a steroid selected from the group of: loteprednol etabonate, dexamethasone, hydrocortisone, prednisolone, prednisone, methylprednisolone, betamethasone, dexamethasone, triamcinolone, beclometasone, fludrocortisone, deoxycorticosterone, and aldosterone. In some embodiments, the topical steroid solution contains loteprednol etabonate. In some embodiments, the topical steroid solution is administered at least once a day.

In some embodiments, at least one of the at least two immunosuppressive agents is a steroid (e.g., a steroid selected from the group of loteprednol etabonate, dexamethasone, hydrocortisone, prednisolone, prednisone, methylprednisolone, betamethasone, dexamethasone, triamcinolone, beclometasone, fludrocortisone, deoxycorticosterone, and aldosterone). In some embodiments, at least one of the two immunosuppressive agents is selected from the group of pimecrolimus, tacrolimus, sirolimus, and cyclosporine. In some embodiments, at least one of the at least two immunosuppressive agents is selected from the group consisting of pimecrolimus, tacrolimus, sirolimus, and cyclosporine. In some embodiments, the at least two immunosuppressive agents are administered at least twice a week (e.g., at least once a day).

Some embodiments further include determining, or alternatively obtaining, providing, or using previously determined information regarding, the number or average density of dendritic inflammatory cells present in the center of the cornea in an eye of the subject, and comparing the number or average density of dendritic inflammatory cells present in the center of the cornea in the eye of the subject to a corresponding reference value. In some embodiments, the determining is performed using in vitro confocal microscopy. Some embodiments further include selecting a subject determined to have an elevated number or density of dendritic inflammatory cells present in the center of the cornea in the eye of the subject as compared to the corresponding reference value.

Also provided are methods of treating a subject that include selectively topically or orally administering to a subject determined to have an elevated number or elevated average density of dendritic inflammatory cells present in the peripheral cornea as compared to a corresponding reference value, at least one anti-inflammatory steroid and/or at least one immunosuppressive agent. Also provided are methods of using at least one anti-inflammatory steroid and/or at least one immunosuppressive agent (e.g., formulated for topical or oral administration) for treating a subject determined to have an elevated number or elevated average density of dendritic inflammatory cells present in the peripheral cornea as compared to a corresponding reference value. Also provided are at least one anti-inflammatory steroid and/or at least one immunosuppressive agent (e.g., formulated for topical or oral administration) for use in treating a subject determined to have an elevated number or elevated average density of dendritic inflammatory cells present in the peripheral cornea as compared to a corresponding reference value and/or for use in the manufacture of a medicament for treating a subject determined to have an elevated number or elevated average density of dendritic inflammatory cells present in the peripheral cornea as compared to a corresponding reference value. In some embodiments, the subject is diagnosed as having eye inflammation. In some embodiments, the subject has limbal stem cell insufficiency. In some embodiments, the at least one anti-inflammatory steroid is selected from the group consisting of: hydrocortisone, cortisone, prednisone, prednisolone, methylprednisolone, dexamethasone, betamethasone, triamcinolone, beclometasone, fludrocortisone, deoxycorticosterone, and aldosterone. In some embodiments, the at least one immunosuppressive agent is a calcineurin inhibitor. In some embodiments, the at least one calcineurin inhibitor is selected from the group of pimecrolimus, tacrolimus, sirolimus, and cyclosporine.

Some embodiments further include determining, or alternatively obtaining, providing, or using previously determined information regarding, the number or average density of dendritic inflammatory cells present in the peripheral cornea in an eye of the subject; and comparing the number or average density of dendritic inflammatory cells present in the peripheral cornea in the eye of the subject to a corresponding reference value. In some embodiments, the determining is performed using in vitro confocal microscopy. Some embodiments further include selecting a subject determined to have an elevated number or density of dendritic inflammatory cells present in the peripheral cornea in the eye of the subject as compared to the corresponding reference value.

Also provided are methods of selecting a subject for participation in a clinical study that include: (a) determining in an eye of a subject, or alternatively obtaining, providing, or using previously determined information regarding, the number or average density of dendritic inflammatory cells present in the peripheral cornea; (b) comparing the number or average density of dendritic inflammatory cells present in the peripheral cornea in the eye of the subject to a corresponding reference value; and (c) selecting a subject having an elevation in the number or average density of dendritic inflammatory cells compared to the corresponding reference value for participation in a clinical study. In some embodiments, the corresponding reference value is a threshold value. In some embodiments, the corresponding reference value is the number or average density of dendritic inflammatory cells present in the peripheral cornea in an eye of a healthy subject.

In any of the methods described herein, the subject can have eye inflammation (e.g., a subject having or diagnosed as having dry eye syndrome, allergy, limbal stem cell deficiency, or graft versus host disease). In any of the methods described herein, the subject can be at increased risk of developing eye inflammation (e.g., a subject at increased risk of developing dry eye syndrome, limbal stem cell deficiency, graft versus host disease, or allergy, or a subject with a history of prior eye inflammation). In any of the methods described herein, the subject can present with one or more physical symptoms of eye inflammation that are observable upon examination without the use of an in vivo confocal microscope (e.g., any of the in vivo confocal microscopes described herein or known in the art). In some embodiments of any of the methods described herein, the subject can be receiving or have been previously treated or received treatment for eye inflammation (e.g., treatment for dry eye syndrome, limbal stem cell insufficiency, graft versus host disease, or allergy).

By the term "efficacy" or "efficacy of treatment" is meant the ability of a treatment (e.g., a therapeutic treatment for an eye inflammatory disorder, e.g., dry eye syndrome) to reduce the number of symptoms of a disease or disorder in a subject (e.g., reduce the number of symptoms of dry eye syndrome) and/or decrease (e.g., a significant, detectable, or observable decrease) the severity, frequency, and/or duration of one or more (e.g., at least two, three, or four) symptoms of a disease or disorder in a subject (e.g., reduce the severity, frequency, and/or duration of one or more symptoms of dry eye syndrome in a subject).

By the term "dry eye syndrome" is a multifactorial disease of the ocular surface and tear film characterized by symptoms of discomfort, visual impairment, and tear film instability. Non-limiting symptoms of dry eye syndrome include stinging, burning, or scratchy sensation in the eye, stringy mucus in or around the eye, increased eye irritation from wind and smoke, eye fatigue after short periods of reading, sensitivity to light, periods of excessive tearing, blurred vision, red eyes, and pain in the eyes. Additional physical symptoms of dry eye syndrome that can be determined using imaging, e.g., in vivo confocal microscopy are described herein. Additional symptoms of dry eye syndrome are known in the art (see, e.g., Yao et al., *Am. J. Med.* 124:1016-1018, 2011). Dry eye syndrome has a variety of different causes. Non-limiting causes of dry eye syndrome include blepharitis, environmental dryness, menopause, infection, Sjogren's syndrome, graft versus host disease, and trauma (e.g., surgical trauma, e.g., refractive surgery). Dry eye syndrome is also known as dry eye disease by those in the art.

By the term "hyperreflective" is meant a cell or cellular structure that reflects more light (e.g., visible light) than a corresponding reference cell or cellular structure (e.g., a cell or cellular structure in an eye of a subject not having an eye disorder, e.g., a subject not having dry eye syndrome). Non-limiting cellular structures that can be hyperreflective include the cytoplasm of a cell or the cell border (e.g., tight junctions). Non-limiting examples of cells that can be hyperreflective include superficial epithelial cells (e.g., superficial epithelial cells present in the center of the cornea). The hyperreflectivity of a cell or cellular structures can be determined in vivo, for example, using the in vivo confocal microscopy methods described herein.

By the term "superficial epithelial cell present in the cornea" is meant an epithelial cell that is present at or near the surface of the cornea.

By the term "center of the cornea" is meant an approximately circular area having a diameter of less than 5 mm (e.g., a diameter less than 4.5 mm, a diameter less than 4 mm, or a diameter of less than 3 mm) from the geometric center point of the cornea. As used herein, the phrase "in the cornea" may include, e.g., an area corresponding to the center of the cornea.

By the term "peripheral cornea" is meant an area in the cornea that falls outside the center of the cornea (as described above).

By the term "in vivo confocal microscopy" is meant the use of a confocal microscope to visualize one or more tissue(s) (e.g., cornea), cells (e.g., superficial epithelial cells present in the cornea), and/or cellular substructures (e.g., nerve branching in the cornea) present within a mammal (e.g., a human). Methods of performing in vivo confocal microscopy are described herein.

By the term "dendritic immune cell," "dendritic inflammatory cell," or "dendritic cell" is meant a bone-marrow derived hyperreflective corpuscular cell with tree-like processes. Dendritic immune cells can act as antigen-presenting cells (e.g., they can phagocytose or endocytose an antigen, and transport and present the antigen to T-lymphocyte(s)). The normal (healthy) cornea (e.g., central cornea) contains immature/precursor-type dendritic cells under steady state conditions; however, these cells can upregulate maturation markers, such as MHC class II molecules, and can increase in reflectivity and size.

By the term "length of a nerve" or "nerve length" is generally meant the distance between the cell body (soma) of the nerve cell and the distal end of the axon (end of the axon that is not proximal to the cell body) of the nerve cell, or the distance between (i) a distal end of a dendrite (end of a dendrite that is not proximal to the cell body) that extends from the cell body at a position approximately opposite to the position in the cell body where the axon extends from the cell body, and (ii) the distal end of the axon of the nerve cell. In some embodiments, the length of a nerve or nerve length can be determined in the cornea of a subject using in vivo confocal microscopy methods, e.g., methods known by those skilled in the art or any of the methods described herein. In some embodiments, nerve length is determined, e.g., by in vivo confocal microscopy, and represented as the sum of the length of the nerve fibers observed per frame, and may be converted into units of microns per $mm^2$.

By the term "reference value" is meant a value that is used for comparative purposes. In some embodiments, a reference value for one or more of the ocular physical parameters described herein can be a threshold value. In some embodiments, a reference value for the one or more ocular physical parameters can be a level or value of the one or more ocular physical parameters measured in a healthy subject (e.g., a subject that does not have dry eye, e.g., does not present with one or more symptoms of an eye disorder (e.g., dry eye syndrome) or a subject that has not been diagnosed as having an eye disorder (e.g., dry eye syndrome)). Additional examples of reference values are described herein.

By the term "topical solution" as used in herein is meant a pharmaceutically acceptable solution (e.g., buffer) that contains a therapeutically effective amount of one or more (e.g., at least two, three, or four) agents (e.g., one or more topically-active steroids). Non-limiting examples of steroids that can be included in these solutions include: loteprednol etabonate, dexamethasone, rimexolone, hydrocortisone, prednisolone, prednisolone acetate, prednisone, methylprednisolone, betamethasone, dexamethasone, triamcinolone, beclometasone, fludrocortisone, deoxycorticosterone, and aldosterone. In some embodiments, a topical solution can contain a combination of at least one steroid and at least one calcineurin inhibitor (e.g., prednisolone and cyclosporine).

By the term "immunosuppressive agent" is meant an agent that inhibits or prevents an activity of the immune system in one or more tissue(s) in the body of a subject. Non-limiting examples of immunosuppressive agents include antibodies (e.g., fully human or humanized antibodies) that specifically bind to CD20, CD25 (e.g., basiliximab or daclizumab), or CD3 (e.g., muromonab); calcineurin inhibitors (e.g., ciclosporin, pimecrolimus, tacrolimus, sirolimus, and/or cyclosporine); interferons (e.g., interferon-β); steroids (e.g., any of the steroids known in the art or described herein); interleukin-1 receptor antagonists; myophenolate mofetil; Prograph®; azathioprine; methotrexate; and/or TNF-α binding proteins (e.g., antibodies and/or soluble TNF-α receptors, e.g., infliximab, etanercept, and/or adalimumab).

By the term "anti-inflammatory steroid" is meant a steroid that reduces inflammation in one or more tissue(s) in a mammal, generally, by binding to glucocorticoid receptors. Non-limiting examples of anti-inflammatory steroids include: hydrocortisone, cortisone, prednisone, prednisolone, methylprednisolone, dexamethasone, betamethasone, triamcinolone, beclometasone, fludrocortisone, deoxycorticosterone, and aldosterone. In some embodiments, an anti-inflammatory steroid can be orally administered to a subject.

By the term "calcineurin inhibitor" is meant an agent that mediates a significant or detectable decrease in the phosphatase activity of calcineruin. Non-limiting examples of calcineurin inhibitors include pimecrolimus, tacrolimus, sirolimus, and cyclosporine.

By the term "subject" is meant any mammal (e.g., a human, mice, rat, and rabbit).

Other definitions appear in context throughout this disclosure. Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

BRIEF DESCRIPTION OF THE DRAWINGS

FIG. 42 is a set of four in vivo confocal microscopy corneal images from (A) an eye from a healthy subject, (B) an eye from a subject having evaporate dry eye syndrome, (C) an eye from a subject having mixed mechanism dry eye syndrome, and (D) an eye from a subject having aqueous-deficient dry eye syndrome.

DETAILED DESCRIPTION OF THE INVENTION

Figure 1:
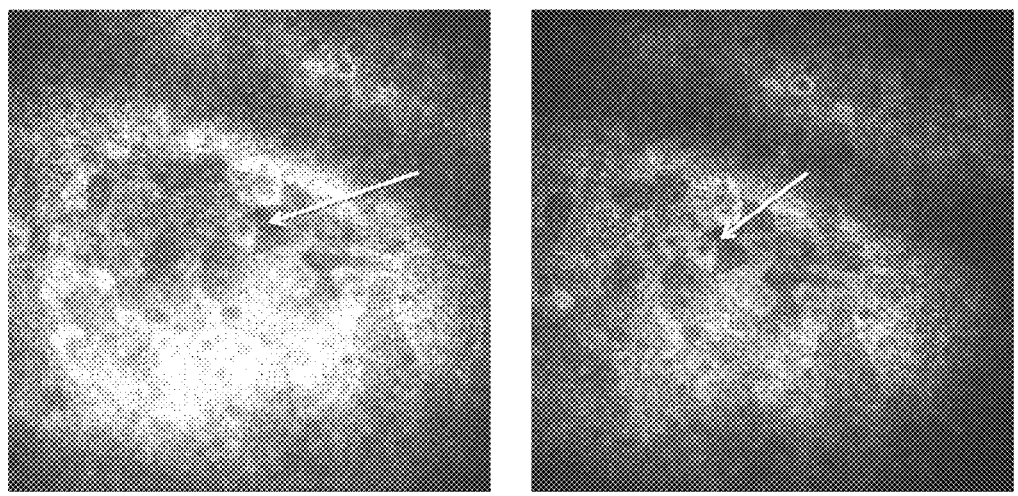
FIG. 1 is set of two in vivo confocal microscopic images of superficial epithelial cells in the central cornea of the right eye of a human subject having dry eye syndrome (human subject #1) prior to treatment.

The invention is based, at least in part, on the discovery that efficacy of treatment of eye inflammation (e.g., treatment of dry eye syndrome, graft versus host disease, limbal stem cell insufficiency, or allergy) in a subject correlates with changes in one or more of the following ocular physical features that can be determined (e.g., using in vivo confocal microscopy): (i) the number or percentage of hyperreflective superficial epithelial cells present in the cornea (e.g., in the center of the cornea), (ii) the average size of superficial epithelial cells present in the cornea (e.g., in the center of the cornea), (iii) the density of superficial epithelial cells present in the cornea (e.g., in the center of the cornea), (iv) the density of dendritic immune cells present in the cornea (e.g., in the center of the cornea), (v) the average size of dendritic immune cells present in the cornea (e.g., in the center of the cornea), (vi) the average area covered by dendritic immune cells present in the cornea (e.g., in the center of the cornea), (vii) the density or average length of nerves present in the cornea, (viii) the amount of branching in nerves present in the cornea, and (ix) the total number of nerves present in the cornea. The invention is also based, in part, on the discovery that subjects having eye inflammation (e.g., subjects having allergy, limbal stem cell insufficiency, graft versus host disease, or dry eye syndrome) have specific physical features (e.g., the number and/or average density of dendritic inflammatory cells present in the peripheral cornea), that can be determined (e.g., using in vivo confocal microscopy), and can be used to select a therapy. In some embodiments, the subjects has not been identified as having any one particular ocular disease. In some embodiments, the subject can have one or more different ocular conditions (e.g., one or more of dry eye syndrome, allergy, infection, limbal stem cell insufficiency, or graft versus host disease).

In view of these discoveries, provided herein are methods of evaluating efficacy of a treatment in a subject having eye inflammation (e.g., a subject having dry eye syndrome, limbal stem cell insufficiency, allergy, or graft versus host disease) and selecting a subject for participation in a clinical study. These methods require determining in an eye of a subject one or more of (i) the number or percentage of hyperreflective superficial epithelial cells present in the cornea (e.g., in the center of the cornea), (ii) the average size of superficial epithelial cells present in the cornea (e.g., in the center of the cornea), (iii) the density of superficial epithelial cells present in the cornea (e.g., in the center of the cornea), (iv) the density of dendritic immune cells present in the cornea (e.g., in the center of the cornea), (v) the average size of dendritic immune cells present in the cornea (e.g., in the center of the cornea), (vi) the average area covered by dendritic immune cells present in the cornea (e.g., in the center of the cornea), (vii) the density or average length of nerves present in the cornea, (viii) the amount of branching in nerves present in the cornea, and (ix) the total number of nerves present in the cornea. Also provided are methods of selecting a subject for participation in a clinical study that include determining in an eye of a subject the number or average density of dendritic inflammatory cells present in the peripheral cornea. In some embodiments of the methods described herein, the determining is performed using in vivo confocal microscopy.

Also provided are methods of treatment that include selectively administering to an eye(s) of a subject having eye inflammation (e.g., a subject having dry eye syndrome), determined to have an elevated density of dendritic immune cells present in the center of the cornea as compared to a reference level, a topical steroid solution; or selectively orally or topically administering to a subject having eye inflammation (e.g., a subject having dry eye syndrome), determined to have no substantial change or a decreased density of dendritic immune cells present in the center of the cornea as compared to a reference level, at least two immunosuppressive agents. Also provided are methods of treating a subject that include selectively orally or topically administering to a subject, determined to have an elevated number or elevated average density of dendritic inflammatory cells present in the peripheral cornea as compared to a corresponding reference value, at least one anti-inflammatory steroid and/or at least one immunosuppressive agent (e.g., at least one calcineurin inhibitor).

Eye Inflammation

Eye inflammation is common and occurs in humans of all ages. It can last from a few minutes to years, depending on the type and severity of the underlying disease, disorder, or condition. Inflammation can occur in one or both eyes at a time, and it may be accompanied by symptoms including itching, excessive tear production, and/or eye discharge. Additional non-limiting symptoms of eye inflammation include pain, redness, swelling, tearing, and unusual warmth or heat. Inflammation can be caused by a variety of different causes. Non-limiting causes of eye inflammation include infection (e.g., bacterial, fungal, viral, or parasitic infection) (e.g., blepharitis, chalazion, conjunctivitis, dacryocystitis, iritis, keratitis, periorbital cellulitis, scleritis, sinusitis, and stye or bordeolum), allergy (e.g., drug allergies, food allergies, hay fever or allergic reaction to an allergen, and insect bite allergy)(e.g., chronic or acute allergy), autoimmune disorders (e.g., ankylosing spondylitis, Behcet's syndrome, dermatomyositis, Graves' disease, juvenile rheumatoid arthritis, multiple sclerosis, psoriatic arthritis, Reiter's syndrome, rheumatoid arthritis, Sjogren's syndrome, systemic lupus erythematosus, and Wegener's granulomatosis), graft versus host disease, dry eye syndrome, limbal stem cell insufficiency, irritation, and injury or trauma to the eye or eyelid (e.g., blunt trauma, corneal abrasion or ulcer, foreign objects or materials, hematoma, insect bite or sting, irritants, and orbital bone fracture). The treatment of eye inflammation typically administered to a subject will depend on the underlying cause of the disease. In some embodiments, the treatment can be, e.g., one or more of an eye lubricant (e.g., liquid or ointment), oral or topical antibiotic, an allergy treatment (e.g., an anti-histamine or cromolyn), and/or an immunosuppressive agent (e.g., a topical steroid or cyclosporine). The treatment prescribed to a patient, or the efficacy of a prescribed treatment, can depend upon the identification of the cause of the eye inflammation in the subject.

Subjects can be diagnosed as having eye inflammation by a medical professional (e.g., a physician, a physician's assistant, a nurse, a nurse's assistant, or a laboratory technician). In any of the methods described herein, the subject can be a child, a teenager, or an adult (e.g., at least 18, 25, 30, 40, 50, 60, 70, 80, or 90 years old). The subject can be a male or a female. A subject diagnosed as having eye inflammation may present with one or more (e.g., two, three, four, five, six, seven, eight, nine, and ten) of the symptoms of eye inflammation described herein. In some embodiments, a subject having eye inflammation (e.g., a low level of inflammation) may not present with a symptom of eye inflammation that can be easily detected by basic examination of an eye(s) of the subject (examination of the patient that does not involve the magnification of the tissues of the eye). In some embodiments, the subject can be diagnosed as having eye inflammation based, in part, on the detection of one or more (e.g., two, three, four, five, six, seven, eight, nine, or ten) of the ocular physical parameters described herein. For example, the subject can be diagnosed as having eye inflammation based on the detection of one or more (e.g., 2, 3, 4, 5, 6, 7, 8, 9, 10, 11, 12, 13, 14, 15, 16, 17, 18, or 19) of the following ocular physical parameters (e.g., using in vivo confocal microscopy): an elevation in the number or percentage of hyperreflective superficial epithelial cells present in the cornea (e.g., in the center of the cornea), an elevation in the average size of superficial epithelial cells present in the cornea (e.g., in the center of the cornea), a decrease in the density of superficial epithelial cells present in the cornea (e.g., in the center of the cornea), an elevation in the density of dendritic immune cells present in the cornea (e.g., in the center of the cornea), an elevation in the average size of dendritic immune cells present in the cornea (e.g., in the center of the cornea), an elevation in the average area covered by dendritic immune cells present in the cornea (e.g., in the center of the cornea), a decrease in the density or average length of nerves present in the cornea, a decrease in the amount of branching in nerves present in the cornea, a decrease in the total number of nerves present in the cornea, an elevation in the number or average density of dendritic inflammatory cells present in the peripheral cornea, an elevation in the hyperreflectivity of epithelial cells in the conjunctiva, an elevation in dendritic cell density in the conjunctiva, an elevation in the average dendritic cell size in the conjunctiva, an elevation in the number of hyperreflective dendritic cells in the conjunctiva, an elevation in the dilation of the lumen of blood vessels in the conjunctiva, an elevation in the average size of inflammatory cells in the blood vessels in the conjunctiva, an elevation in the sticking (elevation in the average time of transitory residence) of inflammatory cells to the blood vessels walls in the conjunctiva, an elevation in the average size of inflammatory cells in the lymph vessels in the conjunctiva, an elevation in the number of inflammatory cells present in the lymph vessels of the conjunctiva, as compared to a reference level of the one or more ocular physical parameters. In some embodiments, the subject may be identified as being at increased risk of developing eye inflammation (e.g., at increased risk of developing dry eye disorder, allergy, graft versus host disease, or limbal stem cell deficiency). In some embodiments, the subject may be suspected of having eye inflammation (e.g., eye inflammation caused by dry eye disorder, allergy, limbal stem cell deficiency, graft versus host disease, or any of the other causes of eye inflammation described herein). In some embodiments, the subject may have a history of previous eye inflammation. In some embodiments, the subject may be receiving a treatment or have previously received a treatment for eye inflammation.

The reference level as described herein can be a threshold level or can be a level of the one or more ocular physical parameters in a healthy subject (e.g., a subject that does not have one or more symptoms of eye inflammation, or a subject that has not been diagnosed as having eye inflammation or an eye disorder) or the same subject at an earlier time points. Non-limiting exemplary threshold values for the density of hyperreflective superficial epithelial cells present in the cornea (e.g., in the center of the cornea) are 65, 70, 75, 80, 85, 90, 95, 100, 105, 110, 115, 120, 125, 130, 135, 140, 145, 150, 155, 160, or 165 cells/mm$^2$, or ranges of 65-75, 75-85, 85-95, 95-105, 105-115, 115-125, 125-135, 135-145, 145-155, or 155-165 cells/mm$^2$. Non-limiting examples of threshold values for the average size of superficial epithelial cells present in the cornea (e.g., in the center of the cornea) are 360, 365, 370, 375, 380, 385, 390, 395, 400, 405, 410, 415, 420, 425, 430, 435, 440, 445, 450, 455, or 460 µm$^2$, or ranges of 360-370, 370-380, 380-390, 390-400, 400-410, 410-420, 420-430, 430-440, 440-450, or 450-460 µm$^2$. Non-limiting examples of threshold values for the density of superficial epithelial cells present in the cornea (e.g., in the center of the cornea) are 1800, 1850, 1900, 1950, 2000, 2050, 2100, 2150, 2200, 2250, 2300, 2350, 2400, 2450, or 2500 cells/mm$^2$, or ranges of 1800-1900, 1900-2000, 2000-2100, 2100-2200, 2200-2300, 2300-2400, or 2400-2500 cells/mm$^2$. Non-limiting examples of threshold values for the length of nerves present in the cornea are a total nerve length of 9000, 10000, 11000, 12000, 13000, 14000, 15000, 16000, 17000, 18000, 19000, 20000, 21000, or 22000 µm/mm$^2$, or ranges of 9000-10000, 10000-11000, 11000-12000, 12000-13000, 13000-14000, 14000-15000, 15000-16000, 17000-18000, 18000-19000, 19000-20000, 20000-21000, or 21000-22000 µm/mm$^2$. Non-limiting examples of threshold values for the amount of branching in nerves present in the cornea are 4, 5, 6, 7, 8, 9, 10, or 11 total number of nerve branches per frame (460 µm×345 µm frame), or ranges of 4-11, 4-10, 5-10, 5-8, or 6-11 total number of nerve branches per frame (460 µm×345 µm frame). Non-limiting examples of threshold values for the total number of nerves present in the cornea are 9, 10, 11, 12, 13, 14, 15, or 16 total number of nerves present per frame (460 µm×345 µm frame), or ranges of 9-16, 10-16, 10-15, 11-15, 9-12, or 12-16 total number of nerves per frame (460 µm×345 µm frame). Non-limiting threshold values for the density of dendritic immune cells in the cornea (e.g., in the center of the cornea) are 0, 5, 10, 15, 20, 25, 30, 35, 40, 45, 50, 55, 60, 65, or 70 cells/mm$^2$, or the ranges of 0-10, 10-20, 20-30, 30-40, 40-50, 50-60, 60-70, 10-50, or 20-70 cells/mm$^2$. Additional threshold values can be determined using methods known in the art or those described herein.

The methods for determining the above ocular physical parameters are described herein. A physician can also monitor a subject for the development of eye inflammation by assessing one or more of these parameters at different points over time (e.g., at least once every six months, at least once a year, at least once every two years, and at least once every three years).

A subject determined to have one or more (e.g., two, three, four, five, six, seven, eight, nine, ten, eleven, twelve, thirteen, fourteen, fifteen, sixteen, seventeen, eighteen, nineteen) of: an elevation in the number or percentage of hyperreflective superficial epithelial cells present in the cornea (e.g., in the center of the cornea), an elevation in the average size of superficial epithelial cells present in the cornea (e.g., in the center of the cornea), a decrease in the density of superficial epithelial cells present in the cornea (e.g., in the center of the cornea), an elevation in the density of dendritic immune cells present in the cornea (e.g., in the center of the cornea), an elevation in the average size of dendritic immune cells present in the cornea (e.g., in the center of the cornea), an elevation in the average area covered by dendritic immune cells present in the cornea (e.g., in the center of the cornea), a decrease in the density or average length of nerves present in the cornea, a decrease in the amount of branching in nerves present in the cornea, a decrease in the total number of nerves present in the cornea, an elevation in the number or average density of dendritic inflammatory cells present in the peripheral cornea, an elevation in the reflectivity of epithelial cells in the conjunctiva, an elevation in dendritic cell density in the conjunctiva, an elevation in the average dendritic cell size in the conjunctiva, an elevation in the number of hyperreflective dendritic cells in the conjunctiva, an elevation in the dilation of the lumen of blood vessels in the conjunctiva, an elevation in the average size of inflammatory cells in the blood vessels in the conjunctiva, an elevation in the sticking (elevation in the average time of transitory residence) of inflammatory cells to the blood vessels walls in the conjunctiva, an elevation in the average size of inflammatory cells in the lymph vessels in the conjunctiva, an elevation in the number of inflammatory cells present in the lymph vessels of the conjunctiva, as compared to a reference level of the one or more ocular physical parameters, can also be selected for treatment (e.g., any of the treatments described herein). The methods can also include recording the results of any of the methods described herein (e.g., diagnosed as having an eye inflammation (e.g., diagnosed as having dry eye syndrome, limbal stem cell deficiency, allergy, or graft versus host disease), or selected for treatment of eye inflammation (e.g., selected for treating of dry eye syndrome, limbal stem cell deficiency, allergy, or graft versus host disease)) in the subject's medical records (e.g., recording the results in a computer readable medium), performing a diagnostic test for eye inflammation (e.g., dry eye syndrome, limbal stem cell deficiency, allergy, or graft versus host disease) on one or more lineal family members of a subject diagnosed as having eye inflammation (e.g., diagnosed as having dry eye syndrome, limbal stem cell deficiency, allergy, or graft versus host disease) using the methods described herein, or monitoring one or more lineal family members of a subject diagnosed as having eye inflammation (e.g., diagnosed as having dry eye disorder, allergy, limbal stem cell insufficiency, or graft versus host disease) using the methods described herein for the development of eye inflammation (e.g., the development of dry eye syndrome, limbal stem cell deficiency, allergy, or graft versus host disease) (e.g., using any of the methods described herein).

Dry Eye Syndrome

Dry eye syndrome is one of the most common eye problems affecting the general population. A tear film normally provides the cornea and conjunctiva with protection from the air. Patients with dry eye syndrome lack a tear film on some surfaces of the cornea and conjunctiva that leads to symptoms of irritation and changing vision. Non-limiting examples symptoms of dry eye syndrome include: stinging, burning, or scratchy sensation in the eyes, stringy mucus in or around the eyes, increased eye irritation from smoke or wind, eye fatigue after short periods of reading, sensitivity to light, periods of excessive tearing, and blurred vision (often worsening at the end of the day or after focusing for a prolonged period). Patients having dry eye syndrome are commonly prescribed artificial tears, an oral antibiotic, and/or cyclosporine. Dry eye syndrome is also referred to as dry eye disease in the art.

In some embodiments, a subject having dry eye syndrome does not have a detectable or observable amount of inflammation (e.g., a subject in a later stage of the disease). In some embodiments, a subject having dry eye syndrome can have an abnormality in the nerves in the cornea (e.g., any of the nerve cell changes observed in subjects having dry eye syndrome described herein) and abnormal epithelial cells in the cornea (e.g., any of the epithelial cell changes observed in subjects having dry eye syndrome described herein), while showing no change in dendritic immune cells in the cornea (e.g., compared to subjects not having eye disorder (e.g., a subject not having dry eye syndrome).

A subject can be diagnosed as having dry eye syndrome by assessment of one or more (e.g., two, three, four, five, six, seven, eight, nine, or ten) of the above symptoms of dry eye syndrome in a subject. Another test that is used to diagnose dry eye syndrome is the Schirmer's tear test (e.g., a test which measures tear production using a blotting strips of paper). Additional tests for diagnosing dry eye syndrome assess the quality of the subject's tears (e.g., the tear quality test commercially available from TearLab Corporation). Additional tests that can, e.g., be performed to diagnose dry eye syndrome include corneal staining (e.g., fluorescein staining) and conjunctival staining (e.g., lissamine green or rose bengal staining)

Subjects can be diagnosed as having dry eye syndrome by a medical professional (e.g., a physician, a physician's assistant, a nurse, a nurse's assistant, or a laboratory technician). In any of the methods described herein, the subject can be a child, a teenager, or an adult (e.g., a subject at least 18, 25, 30, 40, 50, 60, 70, 80, or 90 years old). The subject can be a male or a female. A subject diagnosed as having dry eye syndrome may present with one or more (e.g., two, three, four, five, six, seven, eight, nine, and ten) of the symptoms of dry eye syndrome described herein. In some embodiments, a subject having dry eye syndrome may not present with a symptom of dry eye syndrome that can be easily detected by basic examination of an eye(s) of the subject (examination of the patient that does not involve the magnification of the tissues of the eye). In some embodiments, the subject can be diagnosed as having dry eye syndrome based, in part, on the detection of one or more (e.g., two, three, four, five, six, seven, eight, or nine) of the ocular physical parameters described herein. For example, the subject can be diagnosed as having dry eye syndrome based on the detection of one or more of the following ocular physical parameters (e.g., using in vivo confocal microscopy): an elevation in the number or percentage of hyperreflective superficial epithelial cells present in the cornea (e.g., in the center of the cornea), an elevation in the average size of superficial epithelial cells present in the cornea (e.g., in the center of the cornea), a decrease in the density of superficial epithelial cells present in the cornea (e.g., in the center of the cornea), an elevation in the density of dendritic immune cells present in the cornea (e.g., in the center of the cornea), an elevation in the average size of dendritic immune cells present in the cornea (e.g., in the center of the cornea), an elevation in the average area covered by dendritic immune cells present in the cornea (e.g., in the center of the cornea), a decrease in the density or average length of nerves present in the cornea, a decrease in the amount of branching in nerves present in the cornea, and a decrease in the total number of nerves present in the cornea, as compared to a reference level of the one or more ocular physical parameters. The one or more references level(s) as described herein can be a threshold level (e.g., any of the threshold values described herein) or can be a level of the one or more ocular physical parameters in a healthy subject (e.g., a subject that does not have one or more symptoms of dry eye syndrome or an eye disorder, or a subject that has not been diagnosed as having dry eye syndrome or an eye disorder) or the same subject at an earlier time point (e.g., prior to onset of disease). The methods for determining the above ocular physical parameters are described herein. A physician can also monitor a subject for the development of dry eye syndrome by assessing one or more of these parameters at different time points over time (e.g., at least once every six months, at least once a year, at least once every two years, and at least once every three years).

A subject determined to have one or more (e.g., two, three, four, five, six, seven, eight, or nine) of: an elevation in the number or percentage of hyperreflective superficial epithelial cells present in the cornea (e.g., in the center of the cornea), an elevation in the average size of superficial epithelial cells present in the cornea (e.g., in the center of the cornea), a decrease in the density of superficial epithelial cells present in the cornea (e.g., in the center of the cornea), an elevation in the density of dendritic immune cells present in the cornea (e.g., in the center of the cornea), an elevation in the average size of dendritic immune cells present in the cornea (e.g., in the center of the cornea), an elevation in the average area covered by dendritic immune cells present in the cornea (e.g., in the center of the cornea), a decrease in the density or average length of nerves present in the cornea, a decrease in the amount of branching in nerves present in the cornea, and a decrease in the total number of nerves present in the cornea, as compared to a reference level of the one or more ocular physical parameters, can also be selected for treatment (e.g., any of the treatments described herein).

In Vivo Microscopy

In vivo microscopy (e.g., in vivo confocal microscopy) is a noninvasive procedure that allows the imaging of the living cornea and conjunctiva at the cellular level. Additional non-invasive procedures can be used to perform the methods described herein. A non-invasive procedure, e.g., is one that does not require the puncturing or incision in the tissue of the subject (e.g., in the cornea of the subject).

In vivo microscopy is a technique that enables the study of corneal epithelial cells, corneal dendritic cells, corneal nerves, conjunctival epithelial cells, conjunctival dendritic cells, conjunctival blood vessels, and conjunctival lymphatic vessels. Exemplary methods for detecting these specific cells and structures are described herein.

In vivo confocal microscopes are commercially available from, e.g., Nidek Technologies (Gamagori, Japan) and Heidelberg Engineering GmbH (Dossenheim, Germany). In the methods described herein, the confocal microscopes are commonly equipped with an 35× to 70× immersion lens. For example, a Confoscan microscopy equipped with a 40×/0.75 objective lens or a Heidelberg Engineering GmbH microscope can be equipped with a 63× water-contact lens covered with a sterile single-use polymethylmethacrylate cap (Tomocap, Heidelberg Engineering). The Confoscan microscope, e.g., can produce images of 460 µm by 345 µm, with a magnification of 500× and a lateral resolution of 1 µm/pixel. The Heidelberg microscope, e.g., can produce images of 400 µm by 400 µm, with a magnification of 800× and a lateral resolution of 1 µm/pixel. The subject is typically administered a topical anesthesia (e.g., 0.5% proparacaine hydrochloride) prior to contacting the immersion lens with the subject's eye tissue. A subject can also be administered a lubricating solution (e.g., 2.5% hydroxypropyl methylcellulose) prior to contacting the immersion lens with the subject's eye tissue. The digital images collected can be stored on a computer workstation using commonly known methods. The resulting images can be analyzed using a variety of commercially available software. Non-limiting examples of software that can be used to analyze the collected images include ImageJ software (ImageJ software described in Girish et al., *Indian J. Cancer* 41:47, 2004) and NeuronJ software (Meijering et al., *Cytometry A* 58:167-176, 2004).

Changes in Superficial Epithelial Cells Present in the Cornea

As noted above, the present invention is based, in part, on the discovery that efficacy of treatment of eye inflammation (e.g., treatment of dry eye syndrome or limbal stem cell insufficiency) in humans can be determined by detecting one or more of the change in the number or percentage of hyperreflective superficial epithelial cells present in the cornea (e.g., in the center of the cornea), the change in the average reflectivity of superficial epithelial cells present in the cornea (e.g., in the center of the cornea), the change in the average size of superficial epithelial cells present in the cornea (e.g., in the center of the cornea), and the change in the density of superficial epithelial cells present in the cornea (e.g., in the center of the cornea), where one or more of a decrease in the number or percentage of hyperreflective superficial epithelial cells present in the cornea (e.g., in the center of the cornea), a decrease in the average size of superficial epithelial cells present in the cornea (e.g., in the center of the cornea), and an elevation in the density of superficial epithelial cells present in the cornea (e.g., in the center of the cornea) following treatment or at a later time point during treatment as compared to an earlier time point (e.g., a time point prior to treatment or at an earlier time point during treatment) in the same subject indicate that the treatment is effective.

Exemplary in vivo confocal microscopic methods for determining these changes in superficial epithelial cells present in the cornea are described in the Examples. However, the methods described in the Examples are not limiting. One skilled in the art will recognize that modifications of these methods can be made (e.g., change in the level of magnification, change in autobrightness, the use of gel or the type of caps for the microscope objective lens) without significantly compromising the quality of the images obtained. In some embodiments, two or more images (e.g., three, four, or five images) can be obtained from an eye of the subject. A change in the number or percentage of hyperreflective superficial epithelial cells or the average reflectivity of superficial epithelial cells present in the cornea can be assessed using methods known in the art, e.g., the ImageJ, NIDEK, and Cell Count, Heidelberg Engineering GmbH software. A change in the average size or density of superficial epithelial cells present in the center of the cornea can be assessed using methods known in the art, e.g., the ImageJ, NIDEK, and Cell Count, Heidelberg Engineering GmbH software.

Changes in Dendritic Immune Cells Present in the Central and Peripheral Cornea

The present invention is further based, in part, on the discovery that efficacy of treatment of eye inflammation (e.g., treatment of dry eye syndrome or limbal stem cell insufficiency) in humans can be determined by detecting one or more of a change in the density of dendritic immune cells present in the cornea (e.g., in the center of the cornea), a change in the average size of dendritic immune cells present in the cornea (e.g., in the center of the cornea), and a change in the average area covered by dendritic immune cells present in the cornea (e.g., in the center of the cornea), where one or more of a decrease in the density of dendritic immune cells present in the cornea (e.g., in the center of the cornea), a decrease in the average size of dendritic immune cells present in the cornea (e.g., in the center of the cornea), and a decrease in the average area covered by dendritic immune cells present in the cornea (e.g., in the center of the cornea) following treatment or at a later time point during treatment as compared to an earlier time point (e.g., a time point prior to treatment or at an earlier time point during treatment) in the same subject indicate that the treatment is effective.

Exemplary methods using in vivo confocal microscopy for determining these changes in the dendritic immune cells present in the cornea are described in the Examples. However, the methods described in the Examples are not limiting. One skilled in the art will recognize that modifications of these methods can be made (e.g., change in the level of magnification) without significantly compromising the quality of the images obtained.

Dendritic cells can be morphologically identified as bright individual tree-like structures with cell bodies, which allows for the differentiation of these structures from the corneal nerves. The number of dendritic cells present in the cornea can be counted using software (e.g., Cell Count, Heidelberg Engineering GmbH). The average dendritic cell size and average dendritic cell area can also be analyzed using software (e.g., ImageJ software described in Girish et al., *Indian J. Cancer* 41:47, 2004). Although exemplary software programs are recited above, skilled artisans will appreciate that a number of other suitable software programs are available.

Subjects having acute allergy have also been discovered to have an elevation in dendritic cell density in the peripheral cornea, an elevation in the average dendritic cell size in the peripheral cornea, and an elevation in the number or percentage of hyperreflective dendritic cells in the peripheral cornea. As described herein, the detection of one or more of a change in the dendritic cell density in the peripheral cornea, a change in the average dendritic cell size, a change in the number or percentage of hypperreflective dendritic cells in the peripheral cornea in a subject can be used to select a treatment for a subject having eye inflammation (e.g., a subject having dry eye syndrome, limbal stem cell insufficiency, allergy, or graft versus host disease).

Changes in Nerve Cells in the Cornea

It has further been discovered that efficacy of treatment of eye inflammation (e.g., treatment of dry eye syndrome or limbal stem cell insufficiency) in humans can be determined by detecting one or more of a change in the density or average length of nerves present in the cornea, a change in the amount of branching in nerves present in the cornea, and a change in the total number of nerves present in the cornea, where one or more of an elevation in the density or average length of nerves present in the cornea, an elevation in the amount of branching in nerves present in the cornea, and an elevation in the total number of nerves present in the cornea following treatment or at a later time point during treatment as compared to an earlier time point (e.g., a time point prior to treatment or at an earlier time point during treatment) in the same subject indicate that the treatment is effective.

Exemplary in vivo confocal microscopic methods for determining these changes in the nerve cells present in the cornea are described in the Examples. However, the methods described in the Examples are not limiting. One skilled in the art will recognize that modifications of these methods can be made (e.g., change in the level of magnification) without significantly compromising the quality of the images obtained.

Nerve analysis can be done, e.g., using a software program (e.g., the semi-automated tracing program NeuronJ (Meijering et al., *Cytometry A* 58:167-176, 2004), a plug-in for ImageJ (ImageJ software described in Girish et al., *Indian J. Cancer* 41:47, 2004)). In some embodiments, nerve density can be assessed by measuring the total length of the nerve fibers in micrometers per frame. Nerve branching is defined as the total number of nerve branches in one image. The number of total nerves measured is defined as the number of all nerves, including main nerve trunks and branches in one image. Although exemplary software programs are recited above, skilled artisans will appreciate that a number of other suitable software programs are available.

Determining Efficacy of a Treatment for Dry Eye Syndrome

Provided herein are methods of determining the efficacy of a treatment for eye inflammation (e.g., treatment for dry eye syndrome or limbal stem cell insufficiency) in a subject. These methods include determining in an eye of a subject having eye inflammation (e.g., a subject having dry eye syndrome or limbal stem cell insufficiency) one or more (e.g., two, three, four, five, six, seven, eight, or nine) of (i) the number or percentage of hyperreflective superficial epithelial cells present in the cornea (e.g., in the center of the cornea), (ii) the average size of superficial epithelial cells present in the cornea (e.g., in the center of the cornea), (iii) the density of superficial epithelial cells present in the cornea (e.g., in the center of the cornea), (iv) the density of dendritic immune cells present in the cornea (e.g., in the center of the cornea), (v) the average size of dendritic immune cells present in the cornea (e.g., in the center of the cornea), (vi) the average area covered by dendritic immune cells present in the cornea (e.g., in the center of the cornea), (vii) the density or average length of nerves present in the cornea, (viii) the amount of branching in nerves present in the cornea, and (ix) the total number of nerves present in the cornea at a first time point; determining one or more of (i) the number or percentage of hyperreflective superficial epithelial cells present in the cornea (e.g., in the center of the cornea), (ii) the average size of superficial epithelial cells present in the cornea (e.g., in the center of the cornea), (iii) the density of superficial epithelial cells present in the cornea (e.g., in the center of the cornea), (iv) the density of dendritic immune cells present in the cornea (e.g., in the center of the cornea), (v) the average size of dendritic immune cells present in the cornea (e.g., in the center of the cornea), (vi) the average area covered by dendritic immune cells present in the cornea (e.g., in the center of the cornea), (vii) the density or average length of nerves present in the cornea, (viii) the amount of branching in nerves present in the cornea, and (ix) the total number of nerves present in the cornea in the eye of the subject at a second time point; and comparing the one or more of (i)-(ix) determined at the first and second time points, where the first time point is prior to treatment and the second time point is any time point following the initiation of treatment, or the first time point is following the initiation of treatment and the second time point is at a later time point during or after treatment; and one or more (e.g., two, three, four, five, six, seven, eight, or nine) of a decrease in the number or percentage of hyper-reflective superficial epithelial cells present in the cornea (e.g., in the center of the cornea), a decrease in the average size of superficial epithelial cells present in the cornea (e.g., in the center of the cornea), an elevation in the density of superficial epithelial cells present in the cornea (e.g., in the center of the cornea), a decrease in the density of dendritic immune cells present in the cornea (e.g., in the center of the cornea), a decrease in the average size of dendritic immune cells present in the cornea (e.g., in the center of the cornea), and a decrease in the average area covered by dendritic immune cells present in the center of the cornea, an elevation in the density or average length of nerves present in the cornea, an elevation in the amount of branching in nerves present in the cornea, and an elevation in the total number of nerves present in the cornea, determined at the second time point compared to the first time point indicates that the treatment was effective in the subject. In some embodiments, the determining is performed using in vivo confocal microscopy.

Alternatively, in the above methods, a subject that has one or more (e.g., two, three, four, five, six, seven, eight, or nine) of an elevation or no substantial change in the number or percentage of hyperreflective superficial epithelial cells present in the cornea (e.g., in the center of the cornea), an elevation or no substantial change in the average size of superficial epithelial cells present in the cornea (e.g., in the center of the cornea), a decrease or no substantial change in the density of superficial epithelial cells present in the cornea (e.g., in the center of the cornea), an elevation or no substantial change in the density of dendritic immune cells present in the cornea (e.g., in the center of the cornea), an elevation or no substantial change in the average size of dendritic immune cells present in the cornea (e.g., in the center of the cornea), and an elevation in the average area covered by dendritic immune cells present in the cornea (e.g., in the center of the cornea), a decrease or no substantial change in the density or average length of nerves present in the cornea, a decrease or no substantial change in the amount of branching in nerves present in the cornea, and a decrease or no substantial change in the total number of nerves present in the cornea, determined at the second time point compared to the first time point indicates that the treatment was not effective in the subject. Some embodiments, where the treatment has been indicated to be ineffective in the subject, further include administering, recommending, or prescribing an alternate treatment to the subject. In some embodiments, the alternate treatment can be a different therapeutic agent or a different combination of one or more therapeutic agents. In some embodiments, the alternate treatment can be an increased dosage of one or more therapeutic agents currently being taken by the subject, an increase in the frequency of administration of one or more therapeutic agents currently being taken by the subject, or an alteration in the route of delivery of one or more therapeutic agents being currently taken by the subject. Some embodiments further include recording the results of these methods in the subject's medical records (e.g., recording the results in a computer readable medium), performing a diagnostic test for eye inflammation (e.g., dry eye syndrome, limbal stem cell deficiency, allergy, or graft versus host disease) on one or more lineal family members of the subject using the methods described herein, or monitoring one or more lineal family members of the subject diagnosed using the methods described herein for the development of eye inflammation (e.g., the development of dry eye syndrome, limbal stem cell deficiency, allergy, or graft versus host disease) (e.g., using any of the methods described herein).

Some embodiments further include assessing of one or more (e.g., two, three, four, or five) additional symptoms of eye inflammation (e.g., one or more symptoms of dry eye syndrome) in the subject at the first and/or second time point (e.g., additional symptoms of dry eye syndrome that can be assessed without the use of a microscope). Some embodiments further include performing a tear production test (e.g., Schirmer's test) or a tear quality test (e.g., TearLab® Osmolarity Test, TearLab Corporation) at the first and/or second time point. In some embodiments, the methods are performed as part of a clinical trial or are performed as part of a treatment regimen.

In some embodiments, these methods can be performed by a medical professional (e.g., a physician, a physician's assistant, a nurse, a nurse's assistant, or a laboratory technician). In some embodiments, the subject has been diagnosed as having eye inflammation (e.g., diagnosed as having dry eye syndrome, limbal stem cell insufficiency, graft versus host disease, or allergy). In some embodiments, the subject has an increased risk of developing eye inflammation (e.g., increased risk of developing dry eye syndrome, limbal stem cell insufficiency, or graft versus host disease, allergy) or is suspected of having eye inflammation (e.g., suspected of having dry eye syndrome, limbal stem cell insufficiency, allergy, or graft versus host disease). In some embodiments, the subject has one or more symptoms of eye inflammation (e.g., one or more symptoms of dry eye syndrome, limbal stem cell insufficiency, graft versus host disease, or allergy). In some embodiments, the subject does not present with a symptom of eye inflammation (e.g., a symptom of dry eye syndrome, limbal stem cell insufficiency, allergy, or graft versus host disease) that can be observed without the use of a microscope. In some embodiments, the subject has a form of eye inflammation (e.g., a form of dry eye syndrome, limbal stem cell insufficiency, graft versus host disease, or allergy) that is refractory to previous therapeutic treatment. In some embodiments, the subject has had eye inflammation (e.g., dry eye syndrome, limbal stem cell insufficiency, allergy, or graft versus host disease) for at least one week (e.g., at least two weeks, three weeks, one month, two months, three months, four months, six months, or one year). In some embodiments, the eye inflammation (e.g., dry eye syndrome) can be caused by an autoimmune condition (e.g., any of the autoimmune conditions described herein).

In some embodiments, the subject has a form of dry eye syndrome with both an evaporative and aqueous deficient component. In some embodiment, the subject has aqueous deficient form of dry eye syndrome (e.g., caused by Sjogren's syndrome or graft-versus-host disease). An aqueous deficient form of dry eye syndrome implies that a failure of lacrimal tear secretion is the cause of symptoms and ocular changes in the subject, and can be, e.g., caused by lacrimal acinar destruction or dysfunction. In some embodiments, the subject has an evaporative form of dry eye syndrome. An evaporative form of dry eye syndrome is characterized by, e.g., an excessive water loss from an exposed ocular surface in the presence of normal lacrimal secretory function.

In some embodiments, the subject is a child, a teenager, or an adult (e.g., at least 18, 20, 25, 30, 35, 40, 45, 50, 55, 60, 65, 70, 75, 80, or 90 years old). In some embodiments, the subject is a female (e.g., a post-menopausal female). In some embodiments, the subject is a male. In some embodiments, the subject is already receiving a treatment for eye inflammation (e.g., a treatment for dry eye syndrome, limbal stem cell insufficiency, graft versus host disease, or allergy), the subject terminates the previous treatment for eye inflammation (e.g., treatment for dry eye syndrome, limbal stem cell insufficiency, graft versus host disease, or allergy), and the efficacy of a new treatment is determined using the methods described herein. In some embodiments, the subject is already receiving a treatment for eye inflammation (e.g., treatment for dry eye syndrome, limbal stem cell insufficiency, graft versus host disease, or allergy), the subject begins to take one or more additional (new) therapeutic agent(s) in combination with the old treatment, and the efficacy of the combination of the one or more additional (new) therapeutic agents and the old treatment are determined using the methods described above. In some embodiments, the subject is already receiving a one or more therapeutic agent(s) for eye inflammation (e.g., one or more therapeutic agent(s) for dry eye syndrome, limbal stem cell insufficiency, allergy, or graft versus host disease), and the efficacy of an increased dosage and/or an increased frequency of dosing of the previously administered one or more therapeutic agent(s) is determined using the methods described herein. In some embodiments, the subject is already receiving one or more therapeutic agent(s) for eye inflammation (e.g., one or more therapeutic agent(s) for dry eye syndrome, limbal stem cell insufficiency, graft versus host disease, or allergy), and the efficacy of an alternative route of administration of the one or more therapeutic agent(s) previously administered to the subject is determined using the methods described above.

In some embodiments, the amount of time between the first and the second time point can be at least one week (e.g., at least two weeks, three weeks, one month, two months, three months, four months, six months, or one year).

Some embodiments further include administering a treatment (e.g., one or more therapeutic agents) to the subject between the first and second time points. Some embodiments further include administering a treatment to the subject prior to the first time point. Some embodiments further include determining one or more (e.g., two, three, four, five, six, seven, eight, or nine) of (i)-(ix) at one or more additional time points (e.g., after the second time point) in the eye of the subject having eye inflammation (e.g., a subject having dry eye syndrome, limbal stem cell insufficiency, graft versus host disease, or allergy). In some embodiments, the one or more additional time points occur after the end of the therapeutic treatment.

Methods of Treating a Subject

Also provided are methods of treating a subject having eye inflammation (e.g., a subject having dry eye syndrome, limbal stem cell insufficiency, graft versus host disease, or allergy) that include selectively administering to an eye(s) of a subject having eye inflammation (e.g., subject having dry eye syndrome, limbal stem cell insufficiency, graft versus host disease, or allergy) and determined to have an elevated density of dendritic immune cells present in the center of the cornea as compared to a reference level, a topical steroid solution; or selectively orally or topically administering to a subject having eye inflammation (e.g., a subject having dry eye syndrome, limbal stem cell insufficiency, graft versus host disease, or allergy) and determined to have substantially no change or a decreased density of dendritic immune cells present in the center of the cornea as compared to a reference level, at least two (e.g., three, or four) immunosuppressive agents (e.g., at least one steroid).

Some embodiments further include one or more of: determining a level of dendritic immune cells present in the center of the cornea of the subject; comparing the level of dendritic immune cells present in the center of the cornea of the subject to a reference level; and selecting a subject that has an elevated level of dendritic immune cells present in the center of the cornea as compared to the reference level for treatment. Some embodiments further include selecting a subject having eye inflammation (e.g., a subject having dry eye syndrome, limbal stem cell insufficiency, graft versus host disease, or allergy). In some embodiments, the determining is performed using in vivo confocal microscopy.

In some embodiments, these methods are performed by a medical professional (e.g., a physician, a physician's assistant, a nurse, a nurse's assistant, or a laboratory technician). In some embodiments, the subject may already be taking one or more pharmaceutical agents for treatment of eye inflammation (e.g., one or more pharmaceutical agents for treatment of dry eye syndrome, graft versus host disease, limbal stem cell insufficiency, or allergy), and the subject is instructed or advised to discontinue taking one or more of the previously prescribed one or more pharmaceutical agents. In some embodiments, the subject may already be taking one or more pharmaceutical agents for treatment of eye inflammation (e.g., one or more pharmaceutical agents for treatment of dry eye syndrome, limbal stem cell insufficiency, allergy, or graft versus host disease), and the topical steroid solution or the topically- or orally-administered at least two (e.g., three or four) immunosuppressive agents is administered to the subject in combination with the one or more pharmaceutical agents previously taken by the subject.

In some embodiments, the reference level can be a threshold level or can be the density of dendritic immune cells present in the center of the cornea in a healthy subject (e.g., a subject that does not have an eye disorder, or does not have one or more symptoms of an eye disorder (e.g., an inflammatory eye disease such as dry eye syndrome, acute allergy, and chronic allergy) or a subject that has not been diagnosed as having an eye disorder (e.g., an inflammatory eye disease such as dry eye syndrome, acute allergy, or chronic allergy)) or the same subject at an earlier time point.

Figure 15:
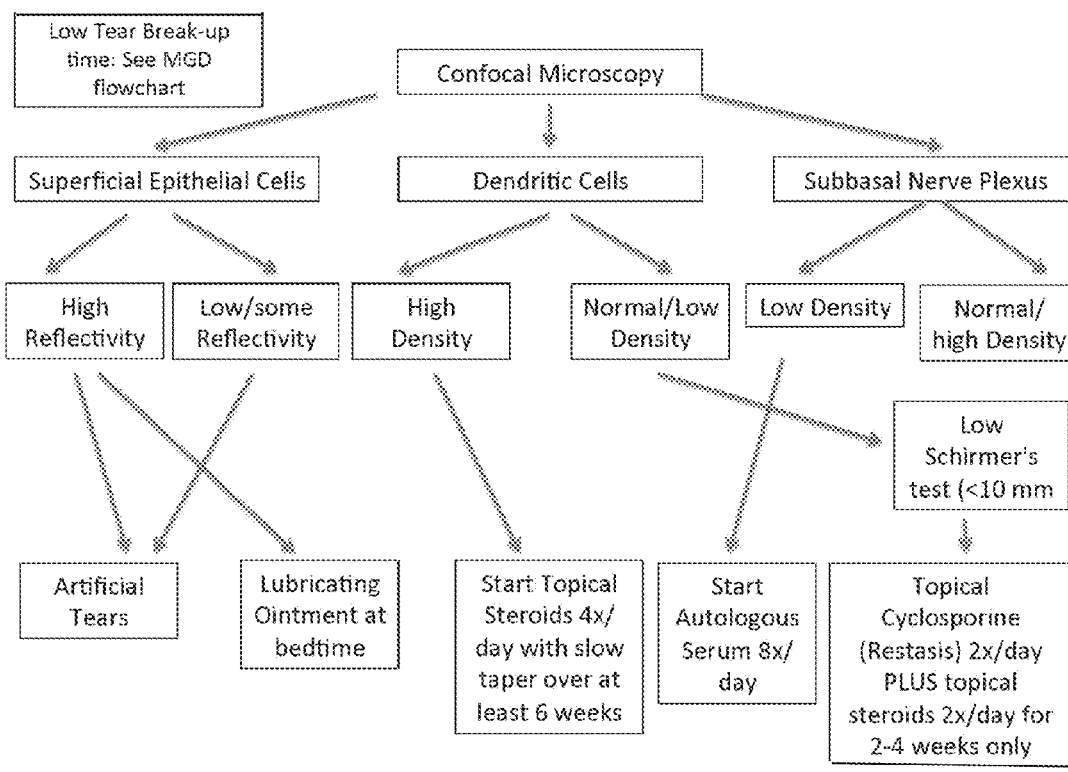
FIG. 15 is a flow chart showing the therapeutic treatments provided herein that include the selective administration of one or more therapeutic agents to a subject having dry eye syndrome on the basis of the number of hyperreflective superficial epithelial cells present in the central cornea, the density of dendritic immune cells in the central cornea, and the density of nerves in the cornea (as determined using in vivo confocal microscopy) as compared to a corresponding reference value. The therapeutic treatments shown can be cumulative (e.g., a subject having an elevated or "high" number of hyperreflective superficial epithelial cells and an elevated or "high" density of dendritic immune cells in the central cornea (as compared to corresponding reference values) can be administered artificial tears in combination with a topical steroid solution).

In some embodiments, the topical steroid solution contains one or more (e.g., two, three, or four) steroid(s) selected from the group of loteprednol etabonate, cortisone, dexamethasone, hydrocortisone, prednisolone, prednisone, methylprednisolone, betamethasone, dexamethasone, rimexolone, prednisolone acetate, triamcinolone, beclometasone, fludrocortisone, deoxycorticosterone, aldosterone, betamethasone, deoxycorticosterone, and aldosterone. In some embodiments, the topical steroid solution comprises loteprednol etabonate. In some embodiments, the topical steroid solution comprises 1% or 0.12% prednisolone acetate. Additional examples of topical steroid solutions are known in the art. In some embodiments, the topical steroid solution is administered to an eye of the subject at least once a day (e.g., at least twice, three times, or four times a day). In some embodiments, the administration of the topical steroid solution occurs before bedtime and/or shortly after awakening (e.g., within one hour of awakening) in the morning. Additional non-limiting methods of treating a subject having dry eye syndrome are shown in FIG. 15.

In some embodiments, the at least two (e.g., three or four) immunosuppressive agents that is topically administered is selected from the group of antibodies (e.g., fully human or humanized antibodies) that specifically bind to CD20, CD25 (e.g., basiliximab or daclizumab), or CD3 (e.g., muromonab); calcineurin inhibitors (e.g., ciclosporin, pimecrolimus, tacrolimus, sirolimus, and/or cyclosporine); interferons (e.g., interferon-β); steroids (e.g., any of the steroids known in the art or described herein); interleukin-1 receptor antagonists; myophenolate mofetil; Prograph®; azathioprine; methotrexate; and/or TNF-α binding proteins (e.g., antibodies and/or soluble TNF-α receptors, e.g., infliximab, etanercept, and/or adalimumab). Additional examples of immunosuppressive agents that can be topically administered are known in the art.

In some embodiments, the at least one of the at least two immunosuppressive agents is a steroid (e.g., one or more of loteprednol etabonate, cortisone, dexamethasone, hydrocortisone, prednisolone, prednisone, methylprednisolone, betamethasone, dexamethasone, triamcinolone, beclometasone, fludrocortisone, deoxycorticosterone, aldosterone, betamethasone, deoxycorticosterone, and/or aldosterone). In some embodiments, at least one of the at least two immunosuppressive agents is a steroid and at least one of the at least two immunosuppressive agents is selected from pimecrolimus, tacrolimus, sirolimus, and cyclosporine. Additional examples of immunosuppressive agents that can be used in these methods are known in the art.

In some embodiments, the at least two (e.g., three or four) immunosuppressive agents are topically and/or orally administered to an eye of the subject at least twice a week (e.g., at least twice, three times, or four times a day). In some embodiments, the topical and/or oral administration of the at least two immunosuppressive agents occurs before bedtime and/or shortly after awakening (e.g., within one hour of awakening) in the morning. In some embodiments, the at least two immunosuppressive agents are formulated together (e.g., present in the same liquid formulation for optical administration). In some embodiments, the at least two immunosuppressive agents are formulated as separate compositions (e.g., each formulated in separate liquid formulations for optical administration).

Also provided are methods of treating a subject (e.g., a subject having eye inflammation, e.g., a subject having dry eye syndrome, acute allergy, chronic allergy, limbal stem cell insufficiency, or graft versus host disease, or any of the other inflammatory eye diseases described herein) that include selectively orally or topically administering to a subject, determined to have an elevated number or elevated average density of dendritic inflammatory cells present in the peripheral cornea as compared to a corresponding reference value, at least one (e.g., two, three, or four) anti-inflammatory steroid and/or at least one (e.g., two, three, or four) immunosuppressive agent (e.g., at least one calcineurin inhibitor).

Some embodiments further include one or more of: determining the level of the number or average density of dendritic inflammatory cells present in the peripheral cornea; comparing level of the number or average density of dendritic inflammatory cells present in the peripheral cornea of the subject to a reference level; and selecting a subject having an elevated number or average density of dendritic inflammatory cells present in the peripheral cornea as compared to the reference level for treatment. In some embodiments, the determining is performed using in vivo confocal microscopy. Some embodiments further include selecting a subject having an inflammatory eye disease (e.g., dry eye syndrome, acute allergy, chronic allergy, or any of the other inflammatory eye diseases described herein).

In some embodiments, these methods are performed by a medical professional (e.g., a physician, a physician's assistant, a nurse, a nurse's assistant, or a laboratory technician). In some embodiments, the subject may already be taking one or more pharmaceutical agents for treatment of inflammatory eye disorder, and the subject is instructed or advised to discontinue taking one or more of the previously prescribed one or more pharmaceutical agents. In some embodiments, the subject may already be taking one or more pharmaceutical agents for treatment of an inflammatory eye disorder, and the at least one anti-inflammatory steroid and/or the at least one immunosuppressive agent (e.g., at least one calcineurin inhibitor) is administered to the subject in combination with the one or more pharmaceutical agents previously taken by the subject.

In some embodiments, the reference level can be a threshold level or can be number or average density of dendritic inflammatory cells present in the peripheral cornea in a healthy subject (e.g., a subject that does not have one or more symptoms of eye disease (e.g., an inflammatory eye disease such as dry eye syndrome, acute allergy, or chronic allergy) or a subject that has not been diagnosed as having an eye disease (e.g., an inflammatory eye disease such as dry eye syndrome, acute allergy, or chronic allergy)) or the same subject at an earlier time point.

In some embodiments, the at least one anti-inflammatory steroid is selected from the group of: hydrocortisone, cortisone, prednisone, prednisolone, methylprednisolone, dexamethasone, betamethasone, triamcinolone, beclometasone, fludrocortisone, deoxycorticosterone, and aldosterone. Additional examples of anti-inflammatory steroids that can, e.g., be used in the methods described herein are known in the art. In some embodiments, the at least one anti-inflammatory steroid is administered to an eye of the subject at least once a day (e.g., at least twice, three times, four times a day). In some embodiments, the at least one anti-inflammatory steroid is orally administered to the subject at least once a week (e.g., at least twice a week or at least once a day). In some embodiments, the at least one anti-inflammatory steroid occurs before bedtime and/or shortly after awakening (e.g., within one hour of awakening) in the morning. In some embodiments, the at least one anti-inflammatory steroid and the at least one immunosuppressive agent (e.g., a calcineurin inhibitor) are administered at approximately the same time (e.g., within 10 minutes of each other).

In some embodiments, the at least one (e.g., two, three, or four) immunosuppressive agent is a calcineurin inhibitor (e.g., ciclosporin, pimecrolimus, tacrolimus, sirolimus, or cyclosporine). Additional examples of immunosuppressive agents that can be used in the methods described herein are known in the art and are described herein (e.g., any of the immunosuppressive agents described herein). In some embodiments, the at least one (e.g., two, three, or four) immunosuppressive agent is topically administered to an eye of the subject at least once a day (e.g., at least twice, three times, four times a day). In some embodiments, the at least one immunosuppressive agent is orally administered to the subject at least once a week (e.g., at least twice a week or at least once a day). In some embodiments, the topical administration of the at least one anti-inflammatory steroid and/or the at least one immunosuppressive agent occurs before bedtime and/or shortly after awakening (e.g., within one hour of awakening) in the morning. In some embodiments, the at least one anti-inflammatory agent and the at least one immunosuppressive agent are present in the same formulation (e.g., a pharmaceutically acceptable solution for optical administration or a solid formulation (e.g., a pill or capsule) for oral administration).

Selecting a Subject for Participation in a Clinical Study

Also provided are methods of selecting a subject (e.g., a subject having eye inflammation, e.g., dry eye syndrome, acute allergy, chronic allergy, limbal stem cell insufficiency, or graft versus host disease) for participation in a clinical study. These methods include determining a level of one or more (e.g., 2, 3, 4, 5, 6, 7, 8, 9, 10, 11, 12, 13, 14, 15, 16, 17, 18, or 19) of the following ocular physical parameters: (i) the number or percentage of hyperreflective superficial epithelial cells present in the cornea (e.g., in the center of the cornea), (ii) the average size of superficial epithelial cells present in the cornea (e.g., in the center of the cornea), (iii) the density of superficial epithelial cells present in the cornea (e.g., in the center of the cornea), (iv) the density of dendritic immune cells present in the cornea (e.g., in the center of the cornea), (v) the average size of dendritic immune cells present in the cornea (e.g., in the center of the cornea), (vi) the average area covered by dendritic immune cells present in the cornea (e.g., in the center of the cornea), (vii) the density or average length of nerves present in the cornea, (viii) the amount of branching in nerves present in the cornea, (ix) the total number of nerves present in the cornea, (x) the number or average density of dendritic inflammatory cells present in the peripheral cornea, (xi) the hyperreflectivity of epithelial cells in the conjunctiva, (xii) the dendritic cell density in the conjunctiva, (xiii) the average dendritic cell size in the conjunctiva, (xiv) the number of hyperreflective dendritic cells in the conjunctiva, (xv) the dilation of the lumen of blood vessels in the conjunctiva, (xvi) the average size of inflammatory cells in the blood vessels in the conjunctiva, (xvii) the sticking (the average time of transitory residence) of inflammatory cells to the blood vessels walls in the conjunctiva, (xviii) the average size of inflammatory cells in the lymph vessels in the conjunctiva, and (xix) the number of inflammatory cells present in the lymph vessels of the conjunctiva, as compared to a reference level of the one or more ocular physical parameters; comparing the one or more of (i)-(xix) (listed above) determined in the eye of the subject to one or more corresponding reference values; and selecting a subject having one or more (e.g., 2, 3, 4, 5, 6, 7, 8, 9, 10, 11, 12, 13, 14, 15, 16, 17, 18, or 19) of: an elevation in the number or percentage of hyperreflective superficial epithelial cells present in the cornea (e.g., in the center of the cornea), an elevation in the average size of superficial epithelial cells present in the cornea (e.g., in the center of the cornea), a decrease in the density of superficial epithelial cells present in the cornea (e.g., in the center of the cornea), an elevation in the density of dendritic immune cells present in the cornea (e.g., in the center of the cornea), an elevation in the average size of dendritic immune cells present in the cornea (e.g., in the center of the cornea), an elevation in the average area covered by dendritic immune cells present in the cornea (e.g., in the center of the cornea), a decrease in the density or average length of nerves present in the cornea, a decrease in the amount of branching in nerves present in the cornea, a decrease in the total number of nerves present in the cornea, an elevation in the number or average density of dendritic inflammatory cells present in the peripheral cornea, an elevation in the reflectivity of epithelial cells in the conjunctiva, an elevation in dendritic cell density in the conjunctiva, an elevation in the average dendritic cell size in the conjunctiva, an elevation in the number of hyperreflective dendritic cells in the conjunctiva, an elevation in the dilation of the lumen of blood vessels in the conjunctiva, an elevation in the average size of inflammatory cells in the blood vessels in the conjunctiva, an elevation in the sticking (elevation in the average time of transitory residence) of inflammatory cells to the blood vessels walls in the conjunctiva, an elevation in the average size of inflammatory cells in the lymph vessels in the conjunctiva, an elevation in the number of inflammatory cells present in the lymph vessels of the conjunctiva, compared to the one or more corresponding reference values for participation in a clinical study. In some embodiments, the determining is performed using in vivo confocal microscopy.

Alternatively, in the above methods, a subject having one or more (e.g., 2, 3, 4, 5, 6, 7, 8, 9, 10, 11, 12, 13, 14, 15, 16, 17, 18, or 19) of a decrease or no substantial difference in the number or percentage of hyperreflective superficial epithelial cells present in the cornea (e.g., in the center of the cornea), a decrease or no substantial difference in the average size of superficial epithelial cells present in the cornea (e.g., in the center of the cornea), an elevation or no substantial change in the density of superficial epithelial cells present in the cornea (e.g., in the center of the cornea), a decrease or no substantial change in the density of dendritic immune cells present in the cornea (e.g., in the center of the cornea), a decrease or no substantial change in the average size of dendritic immune cells present in the cornea (e.g., in the center of the cornea), a decrease or no substantial change in the average area covered by dendritic immune cells present in the cornea (e.g., in the center of the cornea), an elevation or no substantial change in the density or average length of nerves present in the cornea, an elevation or no substantial change in the amount of branching in nerves present in the cornea, an elevation or no substantial change in the total number of nerves present in the cornea, a decrease or no substantial change in the number or average density of dendritic inflammatory cells present in the peripheral cornea, a decrease or no substantial change in the hyperreflectivity of epithelial cells in the conjunctiva, a decrease or no substantial change in dendritic cell density in the conjunctiva, a decrease or no substantial change in the average dendritic cell size in the conjunctiva, a decrease or no substantial change in the number of hyperreflective dendritic cells in the conjunctiva, a decrease or no substantial change in the dilation of the lumen of blood vessels in the conjunctiva, a decrease or no substantial change in the average size of inflammatory cells in the blood vessels in the conjunctiva, a decrease or no substantial change in the sticking (a decrease or no substantial change in the average time of transitory residence) of inflammatory cells to the blood vessels walls in the conjunctiva, a decrease or no substantial change in the average size of inflammatory cells in the lymph vessels in the conjunctiva, a decrease or no substantial change in the number of inflammatory cells present in the lymph vessels of the conjunctiva, compared to the one or more corresponding reference values is selected for participation in a clinical study (e.g., selected as a control subject).

Also provided are methods of selecting a subject (e.g., a subject having dry eye syndrome, limbal stem cell insufficiency, allergy, or graft versus host disease) for participation in a clinical study that include: determining a level of one or more (e.g., 2, 3, 4, 5, 6, 7, 8, or 9) of the following ocular physical parameters: (i) the number or percentage of hyperreflective superficial epithelial cells present in the cornea (e.g., in the center of the cornea), (ii) the average size of superficial epithelial cells present in the cornea (e.g., in the center of the cornea), (iii) the density of superficial epithelial cells present in the cornea (e.g., in the center of the cornea), (iv) the density of dendritic immune cells present in the cornea (e.g., in the center of the cornea), (v) the average size of dendritic immune cells present in the cornea (e.g., in the center of the cornea), (vi) the average area covered by dendritic immune cells present in the cornea (e.g., in the center of the cornea), (vii) the density or average length of nerves present in the cornea, (viii) the amount of branching in nerves present in the cornea, and (ix) the total number of nerves present in the cornea; comparing the one or more of (i) the number or percentage of hyperreflective superficial epithelial cells present in the cornea (e.g., in the center of the cornea), (ii) the average size of superficial epithelial cells present in the cornea (e.g., in the center of the cornea), (iii) the density of superficial epithelial cells present in the cornea (e.g., in the center of the cornea), (iv) the density of dendritic immune cells present in the cornea (e.g., in the center of the cornea), (v) the average size of dendritic immune cells present in the cornea (e.g., in the center of the cornea), (vi) the average area covered by dendritic immune cells present in the cornea (e.g., in the center of the cornea), (vii) the density or average length of nerves present in the cornea, (viii) the amount of branching in nerves present in the cornea, and (ix) the total number of nerves present in the cornea, determined in the eye of the subject to one or more corresponding reference values; and selecting a subject having one or more (e.g., 2, 3, 4, 5, 6, 7, 8, or 9) of an elevation in the number or percentage of hyperreflective superficial epithelial cells present in the cornea (e.g., in the center of the cornea), an elevation in the average size of superficial epithelial cells present in the cornea (e.g., in the center of the cornea), a decrease in the density of superficial epithelial cells present in the cornea (e.g., in the center of the cornea), an elevation in the density of dendritic immune cells present in the cornea (e.g., in the center of the cornea), an elevation in the average size of dendritic immune cells present in the cornea (e.g., in the center of the cornea), an elevation in the average area covered by dendritic immune cells present in the cornea (e.g., in the center of the cornea), a decrease in the density or average length of nerves present in the cornea, a decrease in the amount of branching in nerves present in the cornea, a decrease in the total number of nerves present in the cornea, compared to the one or more corresponding reference values for participation in a clinical study. In some embodiments, the determining is performed using in vivo confocal microscopy.

Alternatively, in the above methods, a subject having one or more (e.g., 2, 3, 4, 5, 6, 7, 8, or 9) of an elevation or no substantial change in the number or percentage of hyperreflective superficial epithelial cells present in the cornea (e.g., in the center of the cornea), a decrease or no substantial change in the average size of superficial epithelial cells present in the cornea (e.g., in the center of the cornea), an elevation or no substantial change in the density of superficial epithelial cells present in the cornea (e.g., in the center of the cornea), a decrease or no substantial change in the density of dendritic immune cells present in the cornea (e.g., in the center of the cornea), a decrease or no substantial change in the average size of dendritic immune cells present in the cornea (e.g., in the center of the cornea), a decrease or no substantial change in the average area covered by dendritic immune cells present in the cornea (e.g., in the center of the cornea), an elevation or no substantial change in the density or average length of nerves present in the cornea, an elevation or no substantial change in the amount of branching in nerves present in the cornea, an elevation or no substantial change in the total number of nerves present in the cornea, compared to the one or more corresponding reference values is selected for participation in a clinical study (e.g., selected as a control subject).

Also provided are methods for selecting a subject (e.g., a subject having eye inflammation, e.g., acute or chronic allergy, dry eye syndrome, limbal stem cell insufficiency, or graft versus host disease) for participation in a clinical study that include: determining in an eye of the subject the number or average density of dendritic inflammatory cells present in the peripheral cornea; comparing the number or average density of dendritic inflammatory cells in the peripheral cornea in the eye of the subject to a corresponding reference value; and selecting a subject having an elevation in the number or average density of dendritic inflammatory cells compared to the corresponding reference value for participation in a clinical study. Alternatively, a subject that has a decrease or no substantial change in the number or average density of dendritic inflammatory cells in the peripheral cornea compared to the corresponding reference value is selected for participation in a clinical study (e.g., as a control subject).

In some embodiments of the methods described herein, the subject has been diagnosed with dry eye syndrome or another inflammatory eye disorder (e.g., any of the inflammatory eye disorders described herein, e.g., acute or chronic allergy, limbal stem cell insufficiency, or graft versus host disease). In some embodiments of the methods described herein, the subject has not been diagnosed as having dry eye syndrome or another inflammatory eye disorder (e.g., any of the inflammatory eye disorders described herein). In some embodiments of the methods described herein, the subject is at increased risk of developing dry eye syndrome or another inflammatory eye disorder (e.g., any of the inflammatory eye disorders described herein) or is suspected of having dry eye syndrome or another inflammatory eye disorder described herein. In some embodiments, the subject has at least one symptoms of dry eye syndrome or another inflammatory eye disorder (e.g., any of the inflammatory eye disorders described herein).

In some embodiments, the reference level can be a threshold level (e.g., any of the threshold values described herein) or can be a level of the one or more ocular physical parameters in a healthy subject (e.g., a subject that does not have one or more symptoms of an eye disorder (e.g., an inflammatory eye disease such as dry eye syndrome, acute allergy, or chronic allergy) or a subject that has not been diagnosed as having an eye disorder (e.g., an inflammatory eye disease such as dry eye syndrome, acute allergy, or chronic allergy)) or the same subject at an earlier time point.

The invention is further described in the following example, which does not limit the scope of the invention described in the claims.

EXAMPLES

Example 1. Detection of Changes in the Superficial Epithelial Cells Present in the Central Cornea of Patients Having Dry Eye Syndrome Upon Treatment In vivo confocal microscopy was performed to image the superficial epithelial cells present in the central corneas of three subjects having dry eye syndrome (i) before or at an early time point in therapy, and (ii) at a second later time point. Each of these patients demonstrated a good response to treatment for his or her dry eye syndrome.

Images were gathered from subject #1 prior to treatment and at 6-weeks after the initiation of treatment (topical loteprednol four times a day for four weeks, followed by twice daily administration of topical loteprednol, with daily administration of artificial tears and Refresh PM ointment at bedtime throughout the treatment period).

Images were gathered from subject #2 early in treatment (four weeks after the initiation of treatment) and at a later time point during treatment (twelve weeks after the initiation of treatment) (autologous serum eight times a day and loteprednol four times a day for four weeks, then loteprednol twice a day for two weeks, then loteprednol once a day for the long-term).

Images were gathered from subject #3 at a time point early in treatment (eight weeks after the initiation of treatment) and at a later time point (nine months after the initiation of treatment) (artificial tears).

Laser scanning in vivo confocal microscopy (Heidelberg Retina Tomograph 3 with the Rostock Cornea Module, Heidelberg Engineering GmbH, Dossenheim, Germany) of the central cornea was performed in these subjects. The microscope used a 670-nm red wavelength diode laser source and was equipped with a 63× objective immersion lens with a numerical aperture of 0.9 (Olympus, Tokyo, Japan). The laser confocal microscope provided images that represent a coronal section of the cornea of 400×400 µm, which is 160,000 µm$^2$ at a selected corneal depth, and separated from adjacent images by approximately 1 to 4 µm with a lateral resolution of 1 µm/pixel. Digital images were stored on a computer workstation at 30 frames per second. A disposable sterile polymethylmethacrylate cap (Tomo-Cap; Heidelberg, Engineering GmbH, Dossenheim, Germany) filled with a layer of hydroxypropyl methylcellulose 2.5% (GenTeal gel; Novartis Ophthalmics, East Hanover, N.J.) in the bottom, was mounted in front of the cornea module optics for each examination. One drop of topical anesthesia 0.5% proparacaine hydrochloride (Alcaine; Alcon, Fort Worth, Tex.) was instilled in both eyes, followed by a drop of hydroxypropyl methylcellulose 2.5% (GenTeal gel, Novartis Ophthalmics) in both eyes. One drop of hydroxypropyl methylcellulose 2.5% was also placed on the outside tip of the cap to improve optical coupling. The tip of the cap was manually advanced towards each patient's eye until the gel contacted the central surface of the cornea.

A total of six to eight volume and sequence scans were obtained from the center of each cornea, at least three of which were sequence scans with particular focus on the subepithelial area, the subbasal nerve plexus, and epithelial dendritic cells, typically at a depth of 14 to 81 µm. A representative image(s) were selected for analysis. The images were selected from the layer immediately at or posterior to the basal epithelial layer and anterior to the Bowman's layer. The criteria to select the images were the best focused and complete images, with the whole image in the same layer, without motion, without folds, and good contrast.

Epithelium reflectivity was assessed by the area of hyper-reflective cells compared to the area of normal cells, and quantitating the amount of hyperreflective nuclei of cells in a single frame (400 µm×400 µm). Epithelial cell size and density was analyzed by manual measurement of the area of the cell and the number of cells in a frame. Both parameters were measured using ImageJ software and the software provided with the microscope. Hyperreflective cells were measured and expressed as a percentage. As is known in the art, the epithelial layer depth may have minor variation from subject to subject or within the area of the cornea in a single subject. The morphology of cells present in the epithelial layer can be used to identify with precision the layer of the cornea to be analyzed.

Figure 2:
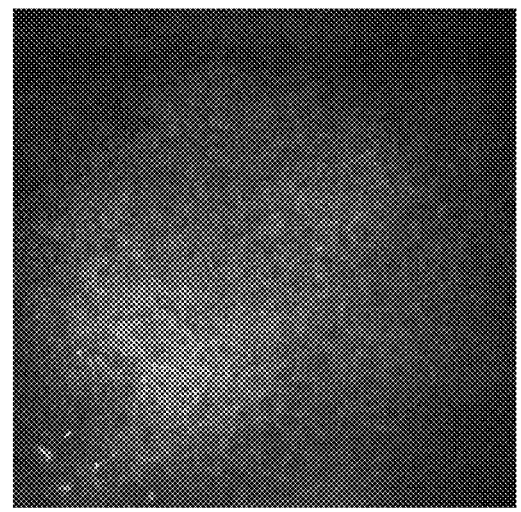
FIG. 2 is an in vivo confocal microscopic image of superficial epithelial cells in the central cornea of the right eye of human subject #1 at 6-weeks following the initiation of treatment (topical loteprednol four times a day for four weeks, followed by twice daily administration of topical loteprednol, daily administration of artificial tears and Refresh PM ointment at bedtime).
Figure 3:
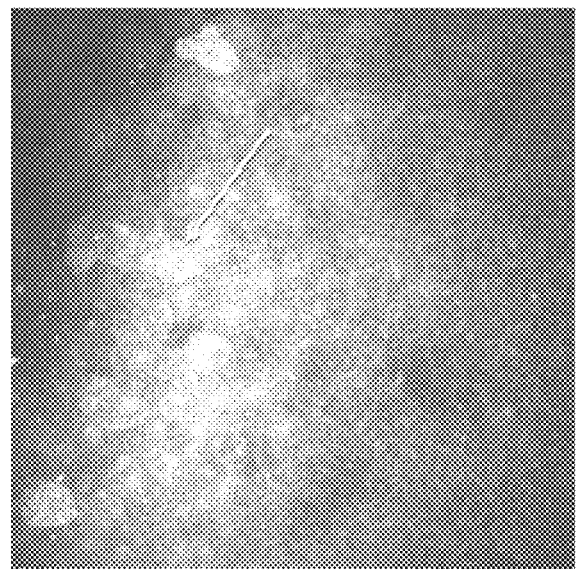
FIG. 3 is an in vivo confocal microscopic image of superficial epithelial cells in the central cornea of the left eye of a human subject having dry eye syndrome (human subject #2) at four weeks after the initiation of treatment (autologous serum eight times a day and loteprednol four times a day for four weeks, then loteprednol twice a day for two weeks, then loteprednol once a day for the long-term).
Figure 4:
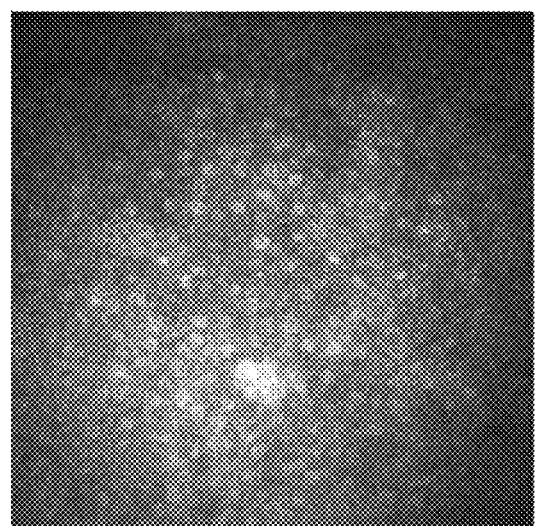
FIG. 4 is an in vivo confocal microscopic image of superficial epithelial cells in the central cornea of the left eye of human subject #2 at 12 weeks after the initiation of therapy (a time point that is eight weeks after the time FIG. 3 was taken).
Figure 5:
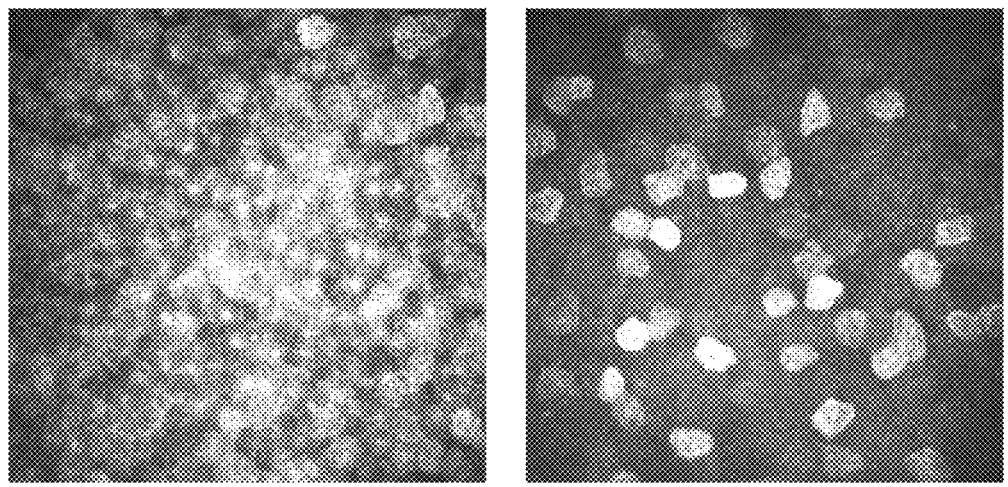
FIG. 5 is two in vivo confocal microscopic images of superficial epithelial cells in the central cornea of the right eye of a human subject having dry eye syndrome (human subject #3) at two months after the initiation of treatment (artificial tears).
Figure 6:
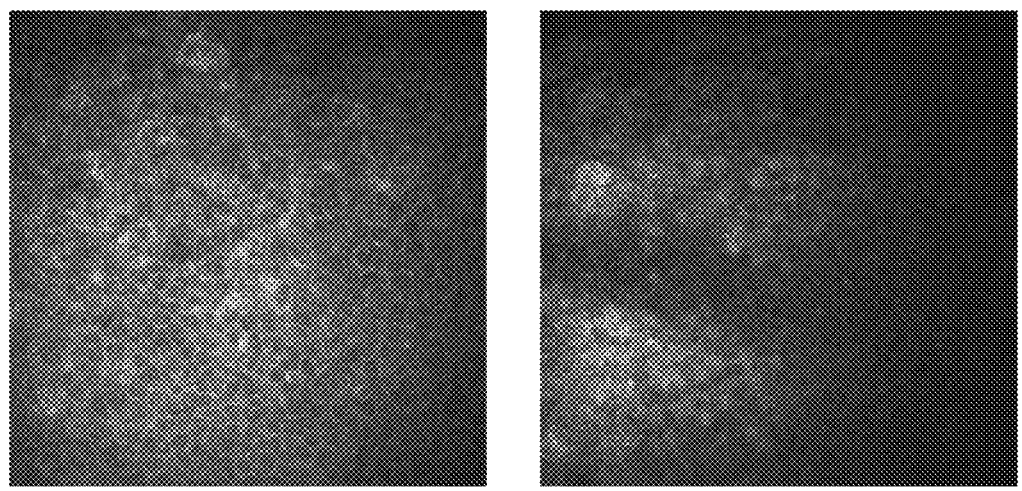
FIG. 6 is two in vivo confocal microscopic images of superficial epithelial cells in the central cornea of the right eye of human subject #3 at 9-months after the initiation of treatment (same treatment as described in FIG. 5; image taken at a time point that is 7-months later than the time the image in FIG. 5 was taken).

The in vivo confocal images gathered from each subject were examined. The images demonstrate that, in patients that show a good response to treatment for his or her dry eye syndrome, there is a decrease in the number or percentage of hyperreflective superficial epithelial cells present in the center of the cornea, a decrease in the average size of superficial epithelial cells present in the center of the cornea, and an elevation in the density of superficial epithelial cells present in the center of the cornea following treatment or at a later time point in treatment as compared to an earlier time point (prior to treatment or at an earlier time point in treatment) in the same subject (compare FIG. 2 to FIG. 1 (human subject #1); FIG. 4 to FIG. 3 (human subject #2), FIG. 6 to FIG. 5 (human subject #3).

These data indicate that efficacy of treatment of dry eye syndrome in humans can be determined by detecting one or more of the change in the number or percentage of hyper-reflective superficial epithelial cells present in the cornea (e.g., in the center of the cornea), the change in the average size of superficial epithelial cells present in the cornea (e.g., in the center of the cornea), and the change in the density of superficial epithelial cells present in the cornea (e.g., in the center of the cornea), where one or more of a decrease in the number or percentage of hyperreflective superficial epithelial cells present in the cornea (e.g., in the center of the cornea), a decrease in the average size of superficial epithelial cells present in the cornea (e.g., in the center of the cornea), and an elevation in the density of superficial epithelial cells present in the cornea (e.g., in the center of the cornea) following treatment or at a later time point during treatment as compared to an earlier time point (a time point prior to treatment or at an earlier time point during treatment) in the same subject indicate that the treatment is effective.

Example 2. Detection of Changes in the Dendritic Cells Present in the Central Cornea of Patients Having Dry Eye Syndrome Upon Treatment In vivo confocal microscopy was performed to image the dendritic cells present in the center of the corneas of two subjects (human subjects #1 and #2; described above) having dry eye syndrome (i) before or at an early time point in therapy, and (ii) at a later time point in therapy. Each of these patients demonstrated a good response to treatment for his or her dry eye syndrome.

Laser scanning in vivo confocal microscopy in these subjects was performed as described in Example 1. The resulting confocal images from two subjects were evaluated for density of immune cells present in the center of the cornea, the average size of dendritic immune cells present in the center of the cornea, and the average area covered by dendritic immune cells present in the center of the cornea. In vivo confocal microscopy images at a depth of 45 to 72 µm at the level of basal epithelial layers, basal lamina, or subbasal nerve plexus were chosen for analysis of dendritic cells. It is noted that the exact identity of the dendritic cells cannot be specified, as they could be monocytes or tissue macrophages, but most likely dendritic cells. Dendritic cells were morphologically identified as bright individual dendriform structures with cell bodies. The number of dendritic cells can be counted using software (Cell Count, Heidelberg Engineering GmbH) in the manual mode. The dendritic cell size and number of dendrites per dendritic cell can be analyzed using ImageJ software (available at NIH website). Dendritic cell size can be measured as the area covered by a single cell.

Figure 7:
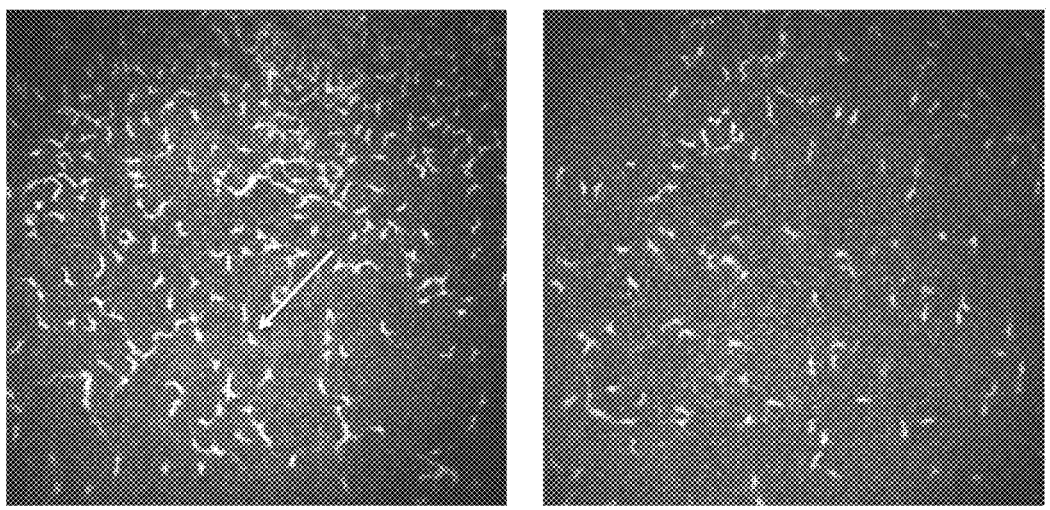
FIG. 7 is two in vivo confocal microscopic images of dendritic immune cells in the central cornea of right eye of human subject #1 (a subject having dry eye syndrome) prior to treatment.
Figure 8:
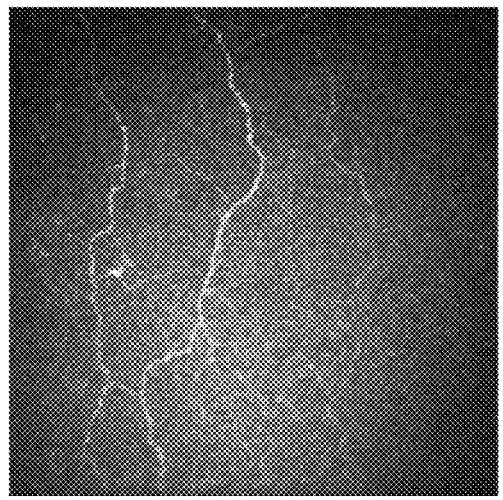
FIG. 8 is an in vivo confocal microscopic image of dendritic immune cells in the central cornea of the right eye of human subject #1 at 6-weeks post-treatment.
Figure 9:
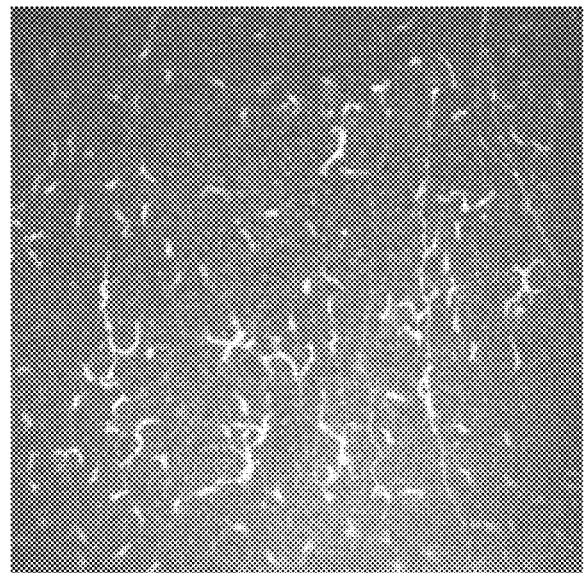
FIG. 9 is an in vivo confocal microscopic image of dendritic immune cells in the central cornea of the right eye of human subject #2 (a subject having dry eye syndrome) at an early time point in treatment.
Figure 10:
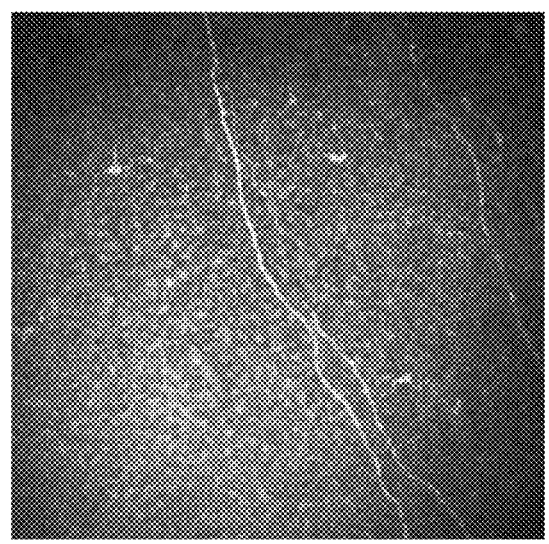
FIG. 10 is an in vivo confocal microscopic image of dendritic immune cells in the central cornea of the right eye of human subject #2 (a subject having dry eye syndrome) at 8-weeks post-treatment (a time point that is later than the time the image in FIG. 9 was taken).

The in vivo confocal images gathered from each subject were examined. The images demonstrate that, in patients that show a good response to treatment for his or her dry eye syndrome, there is a decrease in the density of dendritic immune cells present in the center of the cornea, a decrease in the average size of dendritic immune cells present in the center of the cornea, and a decrease in the average area covered by dendritic immune cells present in the center of the cornea following treatment as compared to prior to treatment or at an earlier time point in the treatment of the same subject (compare FIG. 8 to FIG. 7 (human subject #1); and FIG. 10 to FIG. 9 (human subject #2)).

These data indicate that efficacy of treatment of dry eye syndrome in humans can be determined by detecting one or more of the change in density of dendritic immune cells present in the cornea (e.g., in the center of the cornea), the change in the average size of dendritic immune cells present in the cornea (e.g., in the center of the cornea), and the change in the average area covered by dendritic immune cells present in the cornea (e.g., in the center of the cornea), where one or more of a decrease in the density of dendritic immune cells present in the cornea (e.g., in the center of the cornea), a decrease in the average size of dendritic immune cells present in the cornea (e.g., in the center of the cornea), and a decrease in the average area covered by dendritic immune cells present in the cornea (e.g., in the center of the cornea) following treatment or at a later time point during treatment as compared to an earlier time point (e.g., a time point prior to treatment or at an earlier time point during treatment) in the same subject indicate that the treatment is effective.

Example 3. Detection of Changes in the Corneal Nerves in Patients Having Dry Eye Syndrome Upon Treatment In vivo confocal microscopy was performed to image the nerve cells present in the corneas of two subjects (human subjects #1 and #2; described above) having dry eye syndrome (i) before or at an early time point in therapy, and (ii) at a later time point in therapy. Each of these patients demonstrated a good response to treatment for his or her dry eye syndrome.

Laser scanning in vivo confocal microscopy in these subjects was performed as described in Example 1. The nerve analysis can be done using the semi-automated tracing program NeuronJ (Meijering et al., *Cytometry A* 58:167-176, 2004), a plug-in for ImageJ (available at the imagescience.org website). Nerve density can be assessed by measuring the total length of the nerve fibers in micrometers per frame (160,000 $\mu m^2$). Main nerve trunks are defined as the total number of main nerve trunks in one image after analyzing the images anterior and posterior to the analyzed image to confirm that these did not branch from other nerves. Nerve branching is defined as the total number of nerve branches in one image. The number of total nerves measured is defined as the number of all nerves, including main nerve trunks and branches in one image. The grade of nerve tortuosity can be classified in four grades according to a tortuosity grading scale reported by Oliveira-Soto and Efron (*Cornea* 20:374-384, 2001).

Figure 11:
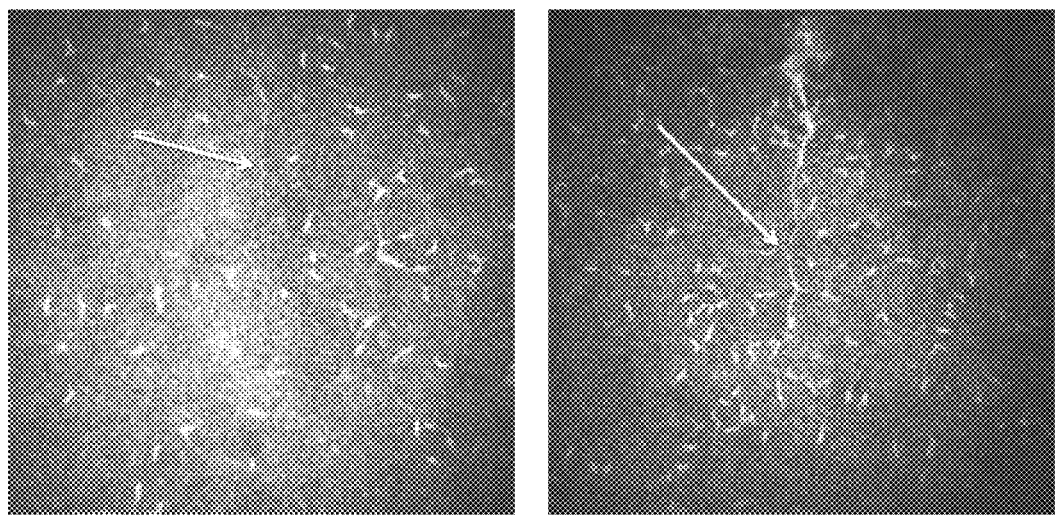
FIG. 11 is two in vivo confocal microscopic images of corneal subbasal nerves in the right eye of human subject #1 (a subject having dry eye syndrome) prior to treatment. The depth of the image on the left is 51 µm, and the depth of the image on the right is 55 µm.
Figure 12:
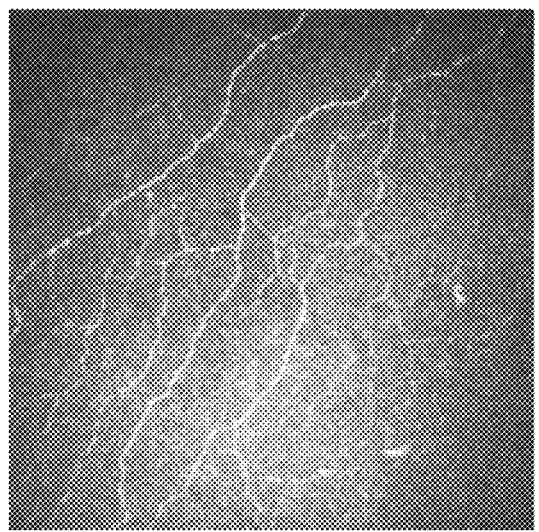
FIG. 12 is an in vivo confocal microscopic image of corneal subbasal nerves in the right eye of human subject #1 at 6-weeks post-treatment. The depth of the image is 65 µm.
Figure 13:
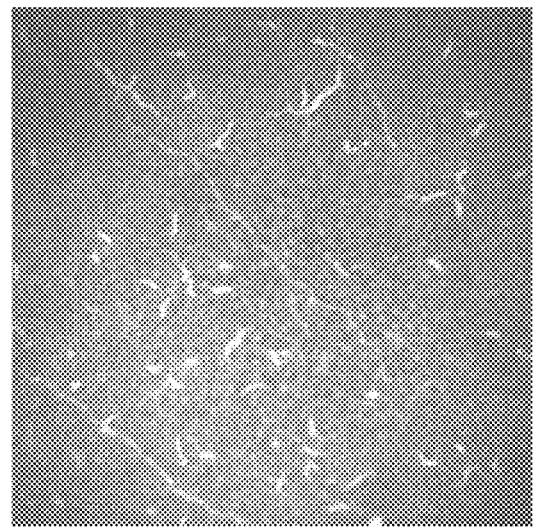
FIG. 13 is an in vivo confocal microscopic image of corneal subbasal nerves in the left eye of human subject #2 (a subject having dry eye syndrome) at an early time point in treatment. The depth of the image is 53 µm.
Figure 14:
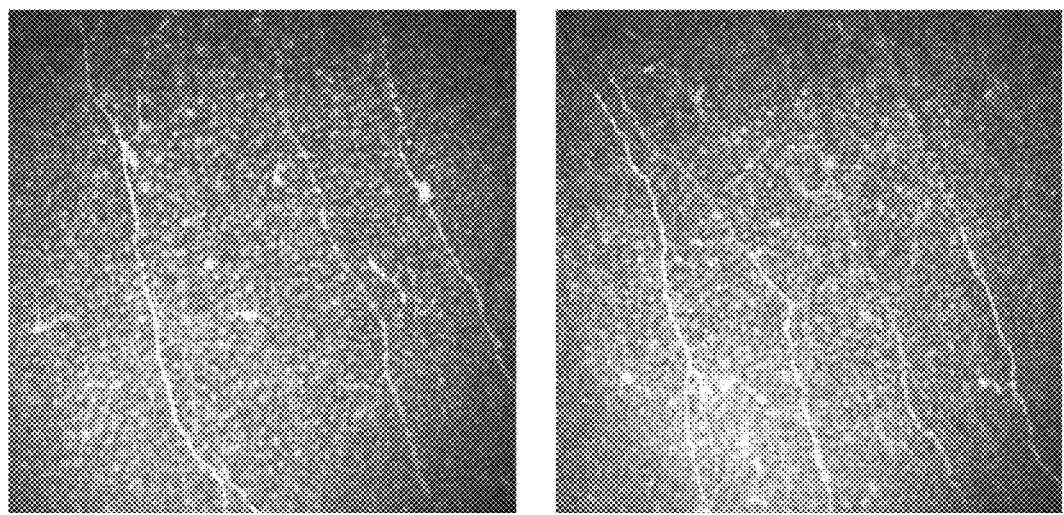
FIG. 14 is two in vivo confocal microscopic images of corneal subbasal nerves in the left eye of human subject #2 at 8-weeks post-treatment (a time point that is later than the time the image in FIG. 13 was taken). The depth of the image on the left is 67 µm, and the depth of the image on the right is 81 µm.

The in vivo confocal images gathered from each subject were examined. The images demonstrate that, in patients that show a good response to treatment for his or her dry eye syndrome, there is an elevation in the density or average length of nerves present in the cornea, an elevation in the amount of branching in nerves present in the cornea, and an elevation in the total number of nerves present in the cornea following treatment as compared to prior to treatment or at an earlier point of treatment in the same subject (compare FIG. 12 to FIG. 11 (human subject #1); and FIG. 14 to FIG. 13 (human subject #2)).

These data indicate that efficacy of treatment of dry eye syndrome in humans can be determined by detecting one or more of the change in the density or average length of nerves present in the cornea, the change in the amount of branching in nerves present in the cornea, and the change in the total number of nerves present in the cornea, where one or more of an elevation in the density or average length of nerves present in the cornea, an elevation in the amount of branching in nerves present in the cornea, and an elevation in the total number of nerves present in the cornea following treatment or at a later time point during treatment as compared to an earlier time point (e.g., a time point prior to treatment or at an earlier time point during treatment) in the same subject indicate that the treatment is effective.

Based on the data in this and the above examples, a physician can selectively prescribe, administer, or recommend a therapeutic treatment to a subject having dry eye syndrome based on ocular physical parameters determined using in vivo confocal microscopy (see, for example, the treatment flow chart shown in FIG. 15).

Example 4. Detection of Changes in the Eyes of Patients Having Acute or Chronic Allergy In vivo confocal microscopic images were gathered from the eyes of normal patients and patients having acute or chronic allergy. The specific eye structures analyzed were superficial epithelial cells in the central cornea, epithelial cells in the conjunctiva, dendritic cells in the conjunctiva, blood vessels in the conjunctiva, lymph vessels in the conjunctiva, dendritic cells in the peripheral cornea, and dendritic cells in the central cornea.

Figure 16:
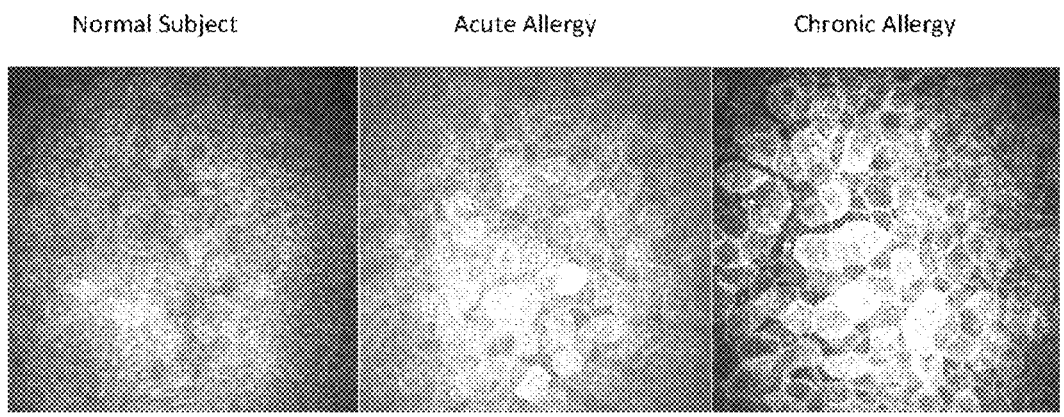
FIG. 16 is three in vivo confocal microscopic images of superficial epithelial cells in the central cornea of a normal subject (left image), a subject having acute allergy (center image), and a subject having chronic allergy (right image). These data show that patients with allergy have an elevated level of epithelial cell border reflectivity (change in tight junctions), an elevated level of epithelial cell reflectivity (squamous metaplasia), and an elevation in the average epithelial cell size in the central cornea as compared to a normal (healthy) subject.

In vivo confocal microscopic analysis of superficial epithelial cells in the central cornea were imaged as described above in Example 1. The resulting data show that subjects having either acute or chronic allergy have an increase in hyperreflective epithelial cells in the central cornea (e.g., an increase in the tight junction and squamous metaplasia light reflectivity) and an increase in the average epithelial cell size in the central cornea as compared to a normal (healthy) subject (FIG. 16; compare the center and right panels to the left panel).

Figure 17:
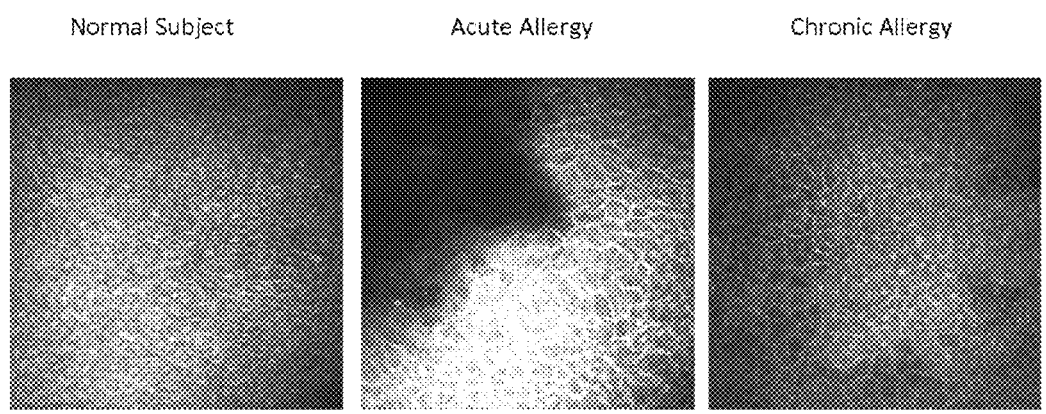
FIG. 17 is three in vivo confocal microscopic images of epithelial cells in the conjunctiva of a normal subject (left image), a subject having acute allergy (center image), and a subject having chronic allergy (right image). The depth of the right image is 39 µm. These data show that patients with allergy have an elevated level of epithelial cell border reflectivity (change in tight junctions) in the conjunctiva as compared to a normal (healthy) subject.

In vivo confocal microscopic analysis of the conjunctival epithelium was generally performed as described in Example 1, except that the microscope was aimed at the bulbar and the tarsal conjunctiva. The images were recorded, and the three best focused images were selected for analysis. The resulting data show that a subject having acute allergy has an elevation in the reflectivity of epithelial cells in the conjunctiva (e.g., elevated reflectivity of the tight conjunctions) as compared to a normal (healthy) control (FIG. 17; compare the center panel to the left panel). Although epithelial cells in the conjunctiva are naturally reflective, the data show a distinct elevation in the level of reflectivity of these epithelial cells in a subject having acute allergy.

Figure 18:
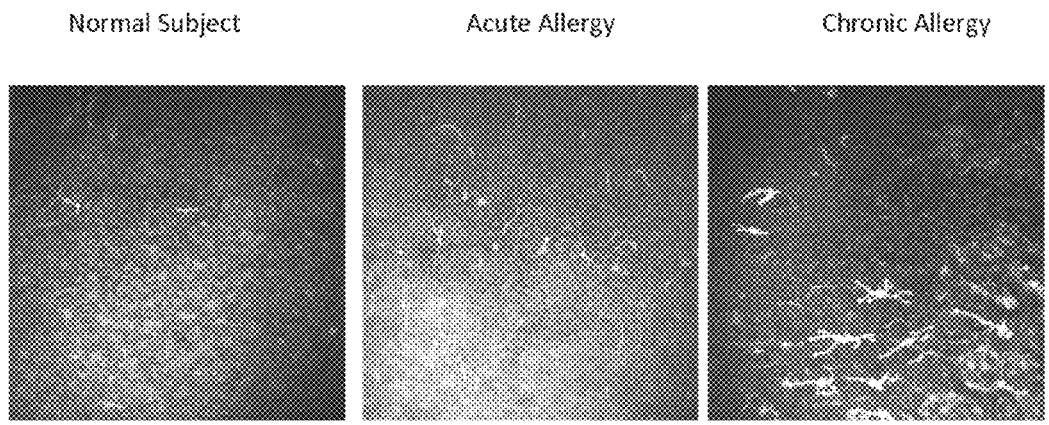
FIG. 18 is three in vivo confocal microscopic images of dendritic cells in the conjunctiva of a normal subject (left image), a subject having acute allergy (center image), and a subject having chronic allergy (right image). The depth of the right image is 53 µm. These data show that patients with allergy have an elevated dendritic cell density, an elevation in the average dendritic cell size, and an elevation in the level of dendritic cell reflectivity in the conjunctiva as compared to a normal (healthy) subject.

In vivo confocal microscopic analysis of conjuctival dendritic cells was generally performed as described in Example 1, except that the microscope was aimed at the subepithelial layers of the bulbar and the tarsal conjunctiva. The images were recorded and the three best focused images were selected to determine dendritic immune cell number and morphology. The resulting data show that subjects having acute or chronic allergy have an elevation in the density of dendritic cells in the conjunctiva, an elevation in the average dendritic cell size in the conjunctiva, and an elevation in the number or percentage of hyperreflective dendritic cells in the conjunctiva as compared to a healthy control (FIG. 18; compare the center and right panels to the left panel).

Figure 19:
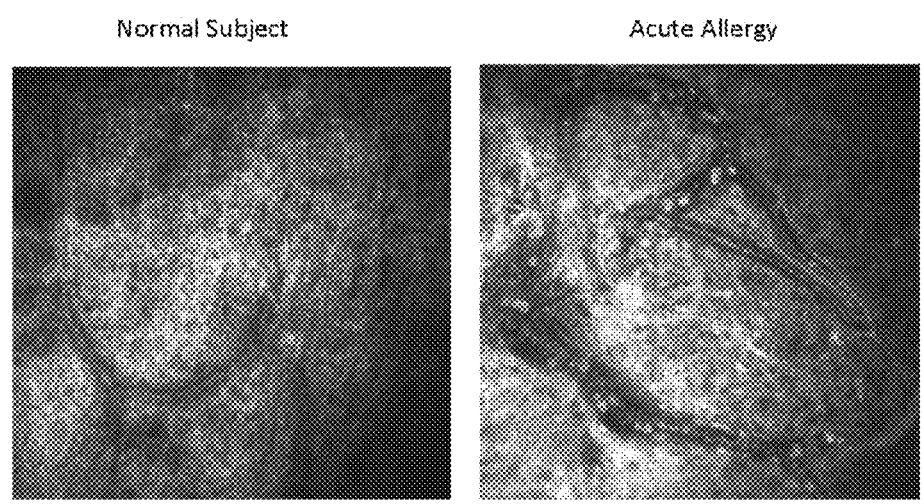
FIG. 19 is two in vivo confocal microscopic images of blood vessels in the conjunctiva of a normal subject (left image) and a subject having acute allergy (right image). The data show that a subject having acute allergy has an elevation in the diameter of the lumen of blood vessels, an elevation in the average inflammatory cell size, and an elevation in the sticking of inflammatory cells to the blood vessel wall (no movement) in the conjunctiva as compared to a normal (healthy) subject.

In vivo confocal microscopy of conjunctival blood vessels was generally performed as described in Example 1, except that the microscope was aimed at the blood vessels of the bulbar conjunctiva. The properties of the blood vessels, and the number and behavior (e.g., sticking to the blood vessel wall) of inflammatory cells, identified as round-shaped hyperreflective corpuscles was analyzed. The resulting data show that a subject having acute allergy has increased dilation in the lumen of blood vessels in the conjunctiva, an elevation in the average size of inflammatory cells present in the conjunctiva, and increased sticking (e.g., increased time of transient residence) of inflammatory cells to the blood vessel wall in the conjunctiva as compared to a normal (healthy) control (FIG. 19; compare the right panel to the left panel).

Figure 20:
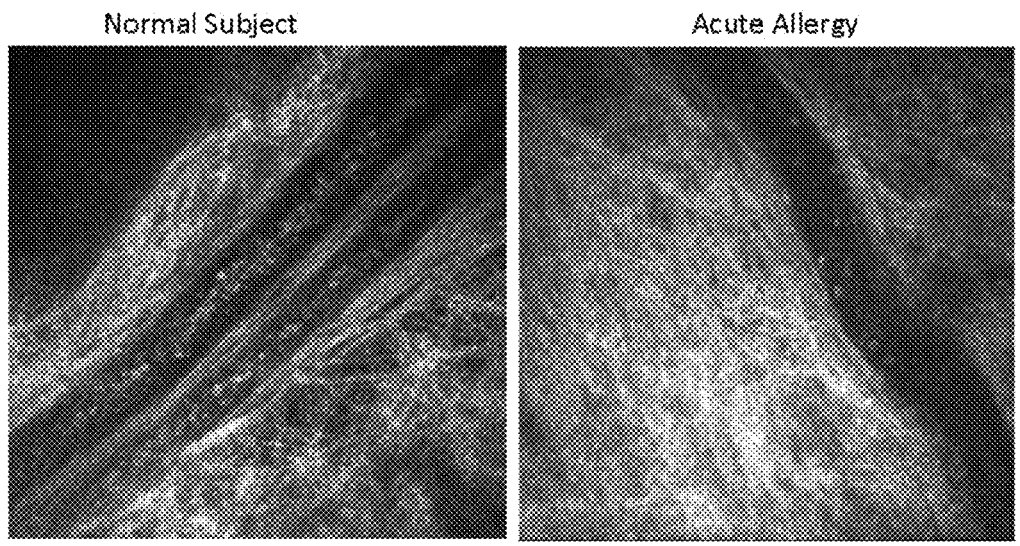
FIG. 20 is two in vivo confocal microscopic images of lymph vessels in the conjunctiva of a normal subject (left image) and a subject having acute allergy (right image). The data show that a subject having acute allergy has an elevation in the number of inflammatory cells present in the lymph vessel wall and an elevation in the average size of inflammatory cells in the lymph vessels of the conjunctiva as compared to a normal (healthy) subject.

Conjunctival lymphatic vessels were also imaged using in vivo confocal microscopy. This imaging was also performed as generally described in Example 1, except that the microscope was aimed at the lymphatic vessels of the bulbar conjunctiva. The resulting data show that a subject having acute allergy has an elevated number of inflammatory cells present in lymphatic vessels in the conjunctiva and an elevation in the average size of the inflammatory cells present in lymphatic vessels in the conjunctiva as compared to a normal (healthy) subject (FIG. 20; compare the right panel to the left panel).

Figure 21:
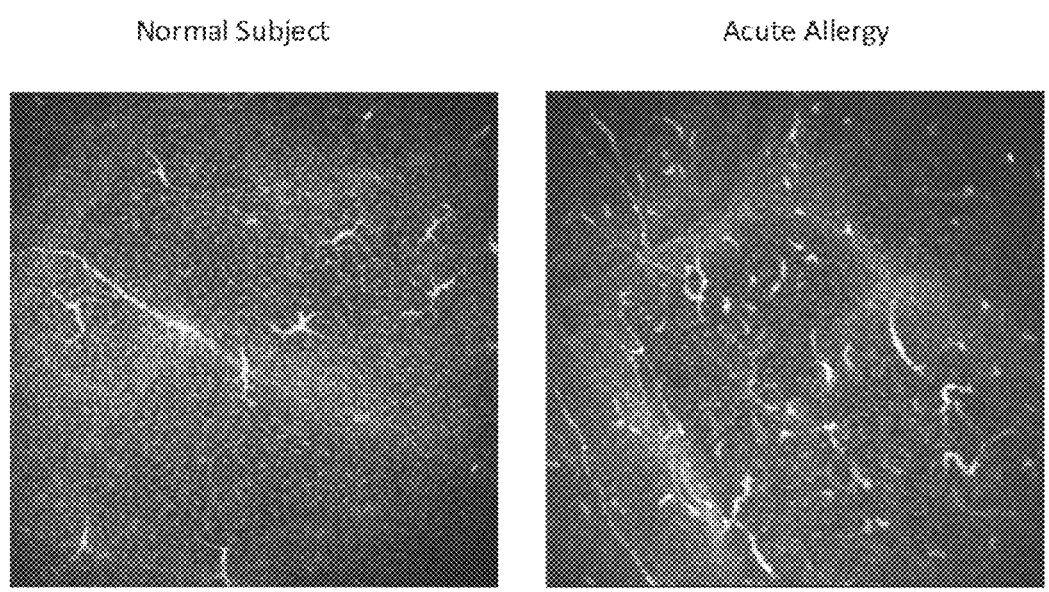
FIG. 21 is two in vivo confocal microscopic images of dendritic cells in the cornea of a normal subject (left image) and a subject having acute allergy (right image). The data show that a subject having an acute allergy has an elevation in the density of dendritic cells, an elevation in the average dendritic cell size, and an elevation in the level of dendritic cell reflectivity in the cornea as compared to a normal (healthy) subject.

Dendritic cells in the peripheral cornea were also imaged using in vivo confocal microscopy (performed as described in Examples 1 and 2). The data gathered show that a subject having acute allergy has an elevation in dendritic cell density in the peripheral cornea, an elevation in the average dendritic cell size in the peripheral cornea, and an elevation in the number of hyperreflective dendritic cells as compared to a normal (healthy) subject (FIG. 21; compare the right panel to the left panel).

Figure 22:
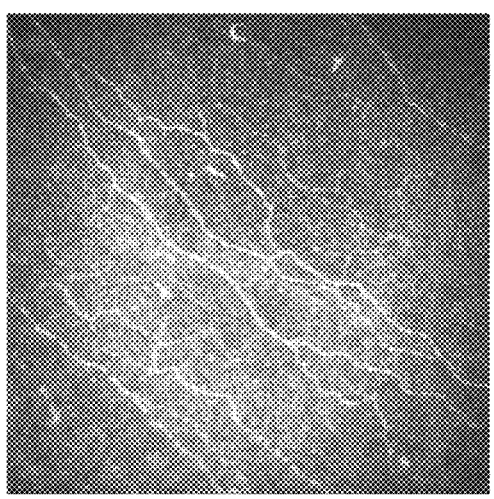
FIG. 22 is two in vivo confocal microscopic images of dendritic cells in the central cornea of a normal subject (left image) and a subject having acute allergy (right image). The data show that a subject having acute allergy has an elevation in the average dendritic cell size in the central cornea as compared to a healthy subject.
Figure 22:
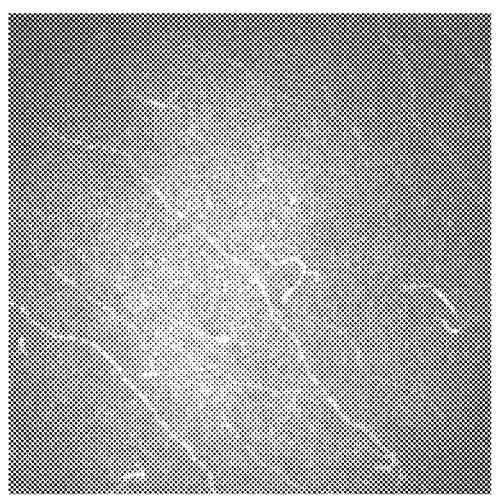

Dendritic cells in the central cornea were also imaged using in vivo confocal microscopy (performed as described in Examples 1 and 2). The resulting data show that a subject having acute allergy has an elevation in the average dendritic cell size in the central cornea as compared to a normal (healthy) subject (FIG. 22; compare the right panel to the left panel).

These data indicate that in vivo confocal microscopy can be used to identify subjects that can benefit from a specific therapeutic treatment. For example, in vivo confocal microscopic imaging can be performed on a subject, and the subject administered, prescribed, or recommended a specific treatment based on the physical substructures in the eye detected using in vivo confocal microscopy (e.g., any of the substructures described herein).

Example 5. Study of Ocular Physical Parameters in Subjects with Dry Eye Syndrome Additional experiments were performed to identify additional ocular structural changes that appear in subjects having dry eye syndrome.

Materials and Methods

Twenty-four eyes of 24 patients with dry eye syndrome (DES) and 15 eyes of 15 normal volunteers were included in the study. A detailed clinical history and slit lamp biomicroscopy examination was performed for each participant. DES was diagnosed based on symptoms (foreign body sensation and dryness of the eye) and a Schirmer I test result of <10 mm/5 minutes. Tear break-up time (TBUT) was recorded as the average of three successive measurements. The corneal fluorescein staining score was evaluated based on grades 0 to 3 in each of the four quadrants for a total score of 12, according to the National Eye Institute grading scale. All normal control subjects did not have any ocular irritation, did not use any ocular medication, and had normal Schirmer test (>10 mm/5 minutes) and normal slit lamp biomicroscopy exam. The exclusion criteria included history of ocular trauma, ocular surgery, contact lens use, drug allergy, diabetes, or the presence of other systemic or ocular disease except dry eye.

In vivo slit scanning confocal microscopy (Confoscan 4; Nidek Technologies, Gamagori, Japan) was performed in the central cornea of all subjects as has described herein. The contralateral eye was fixed to a light source to stabilize the patient's view. The microscope was equipped with a 40×/0.75 objective lens. One drop of topical anesthesia of 0.5% proparacaine hydrochloride (Alcaine, Alcon) was instilled in both eyes. A drop of 0.3% hypromellose (GenTeal gel, Novartis) was applied as coupling medium between the tip of the objective lens and the cornea. Full thickness confocal scans were acquired at a speed of 25 frames per second, obtaining 350 images per scan, every 7 µm. A second scan was obtained for the anterior cornea, obtaining sections every 3 µm. Each image represented a coronal section of 460×345 µm with a minimum axial step of 1 µm, magnification of 500×, and lateral resolution of 1 µm/pixel. A total of 4 to 8 scans were obtained for each cornea by the same experienced operator in all subjects, depending on full thickness or anterior scan mode.

A minimum of 3 representative images of the superficial epithelium, of the basal epithelium, and of the subbasal nerve plexus were selected for analysis for each eye. Two masked observers evaluated the in vivo confocal images for superficial epithelial cell density, superficial epithelial cell size, number of hyperreflective cells in the superficial epithelial cell layer, basal epithelial cell density, and analyzed the corneal subbasal nerve plexus. Briefly, nerve density was assessed by measuring the total length of the nerve fibers in micrometers per $mm^2$ (area of interest=0.1335 $mm^2$). Main nerve trunks were defined as the total number of main nerves in one image. Nerve branching was defined as the total number of nerve branches in one image. The number of total nerves measured was defined as the number of all nerves, including main nerve trunks and branches in one image. The grade of nerve tortuosity was classified in four grades according to a tortuosity grading scale reported by Oliveira-Soto et al. (*Cornea* 20:374-384, 2001). Statistical analysis was performed with SAS software version 9.2 (SAS Institute Inc., Cary, N.C., USA). Data from one randomly chosen eye per person was used for analysis. Data distribution and homogeneity of variance were analyzed. Comparisons were performed by two-tailed t-test and correlations were assessed by Pearson correlation coefficient. Differences were considered statistically significant for p-values less than 0.05.

Results

Twenty-four eyes of 24 patients with diagnosis of DES were included for analysis in the study and were compared with 15 eyes of 15 normal volunteers. The mean age of the DES patients was 55.1±19.1 with a male/female ratio of 10/14, and in the control group the mean age was 59±17 with a male/female ratio of 8/7. The clinical evaluation of DES was apparent in the DES group compared to the normal controls: TBUT (3.0±1.9 vs. 11.7±1.0; p<0.0001), Schirmer I test (3.3±2.2 vs. 13.1±1.0; p<0.0001), and corneal staining (3.2±1.4 vs. 0±0; p<0.0001). The demographics and clinical data of the DES group and control group are shown in Table 1.

TABLE 1

Demographic data of normal controls and patients with dry eye syndrome.

|  | Controls | Dry Eye Syndrome |
|---|---|---|
| Number of patients (n) | 15 | 24 |
| Age (mean ± SD) (years) | 59 ± 17 | 55.1 ± 19.1 |
| Gender (male/female) | 8/7 | 10/14 |
| Tear break up time (TBUT) (seconds) | 11.7 ± 1.0 | 3.0 ± 1.9 |
| Schirmer I test (mm) | 13.1 ± 1.0 | 3.6 ± 2.0 |
| Corneal fluorescein staining score | 0 | 3.3 ± 1.5 |

Values are mean ± standard deviation (SD).

The mean nerve parameters and corneal epithelial cell parameters for DES and normal control groups are shown in Table 2.

Figure 23:
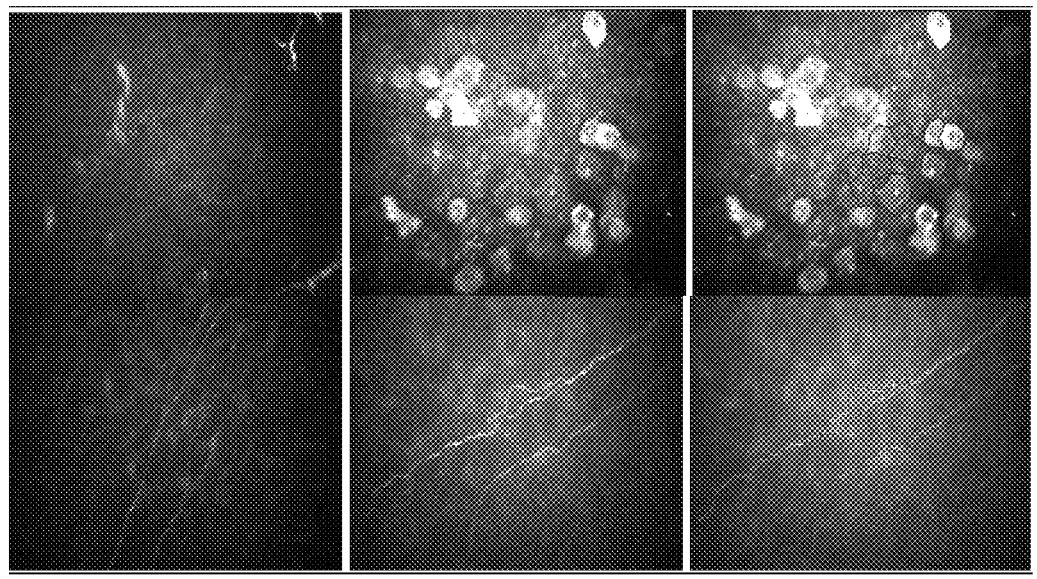
FIG. 23 is a set of six confocal microscopic images showing the corneal epithelium and the subbasal nerve plexus in patients with dry eye syndrome. The top left image shows superficial epithelial cells in the normal eye. The top center image shows superficial epithelial cells in a subject having dry eye syndrome. The top right image shows epithelial cell counting in a subject having dry eye syndrome. The bottom left image shows the sub-basal nerve plexus in a normal subject. The bottom center image is the sub-basal nerve plexus in a subject having dry eye syndrome. The bottom right image shows nerve density counting in a subject having dry eye syndrome using Image J software.
Figure 24:
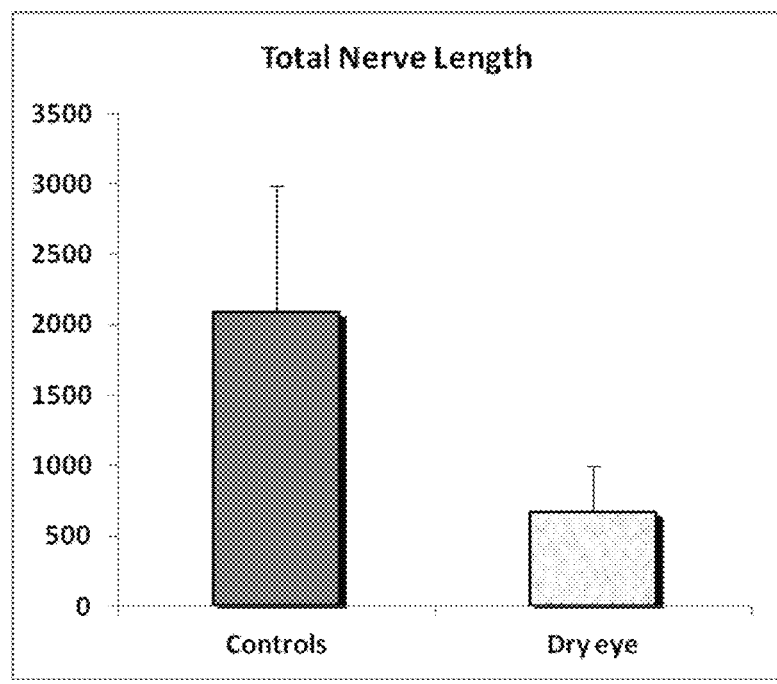
FIG. 24 is a graph showing the total nerve length in control subjects and subjects having dry eye syndrome. The error bars represent the standard deviation from the mean.
Figure 25:
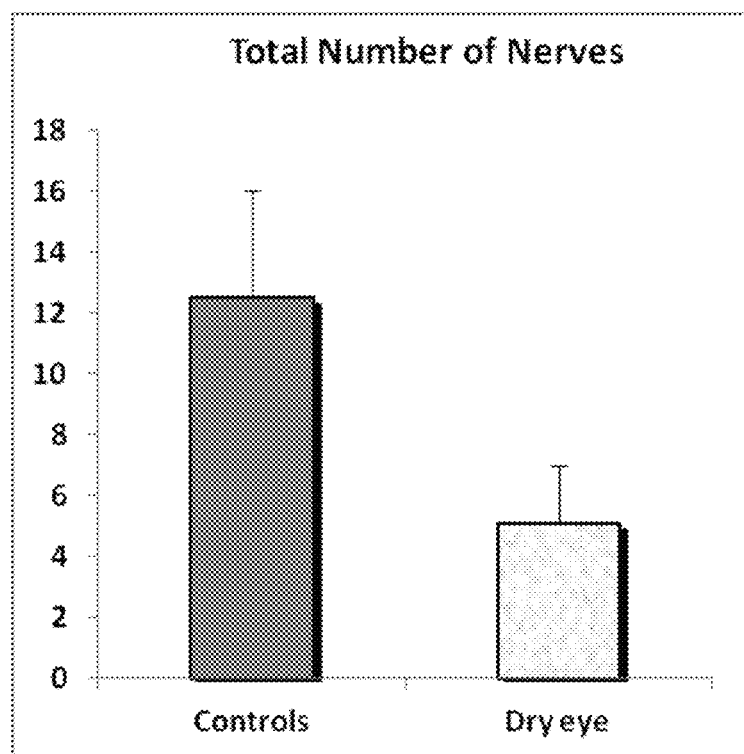
FIG. 25 is a graph showing the total number of corneal nerves in control subjects and subjects having dry eye syndrome. The error bars represent the standard deviation from the mean.
Figure 26:
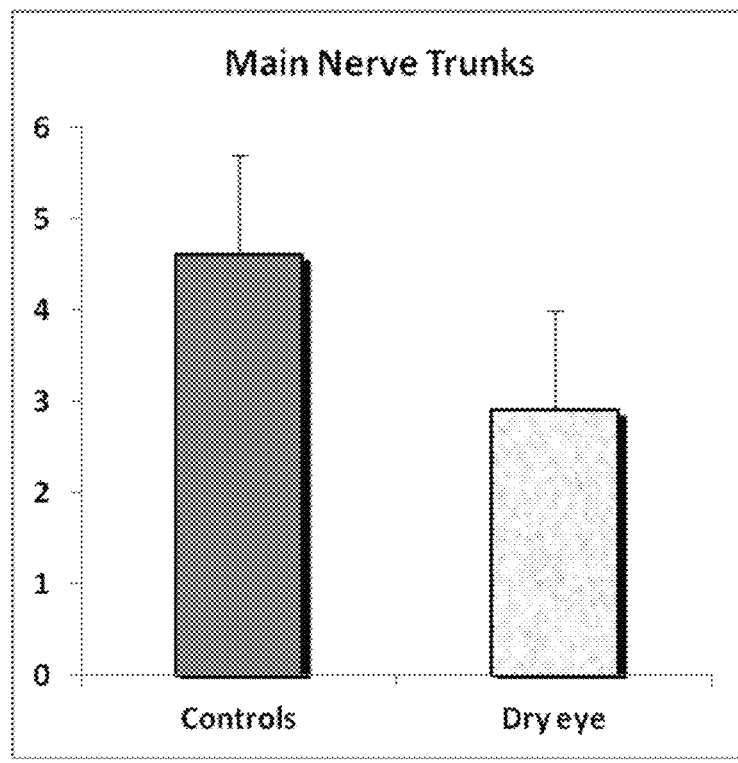
FIG. 26 is a graph showing the number of corneal main nerve trunks in control subjects and subjects having dry eye syndrome. The error bars represent the standard deviation from the mean.
Figure 27:
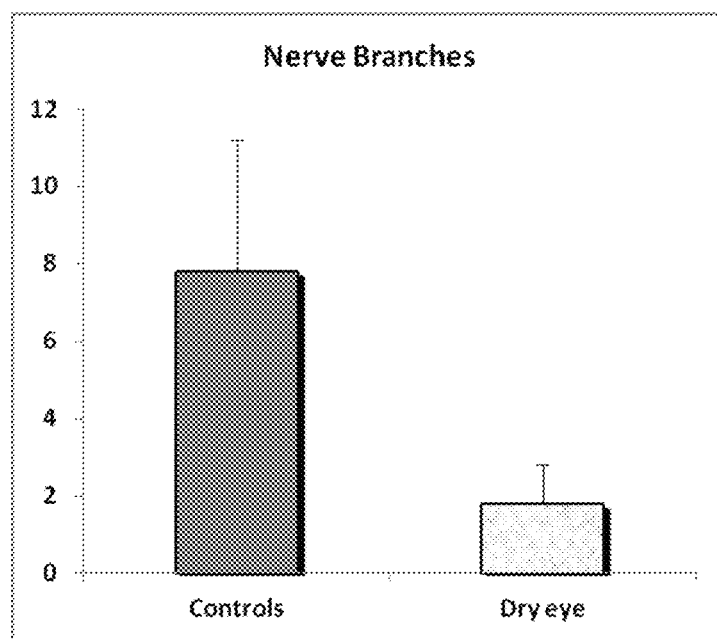
FIG. 27 is a graph showing the number of corneal nerve branches in control subjects and subjects having dry eye syndrome. The error bars represent the standard deviation from the mean.

In the group of patients with DES, the corneal subbasal nerve plexus was significantly reduced (FIG. 23). Specifically, the mean total nerve length (5,036.0±2,459.2 vs. 15,690.6±6,695.1 µm/mm2), total number of nerves (5.1±1.9 vs. 12.5±3.5; p<0.0001), main nerve trunks (2.9±1.1 vs. 4.6±1.1; p<0.0001), and number of branches (1.8±1.0 vs. 7.8±3.4; p<0.0001) were significantly lower as compared to controls (FIGS. 24-27). The nerve tortuosity was slightly increased in DES compared to controls, but did not reach statistical significance (1.9±0.7 vs. 1.6±0.3; p=0.124) (data not shown).

Figure 28:
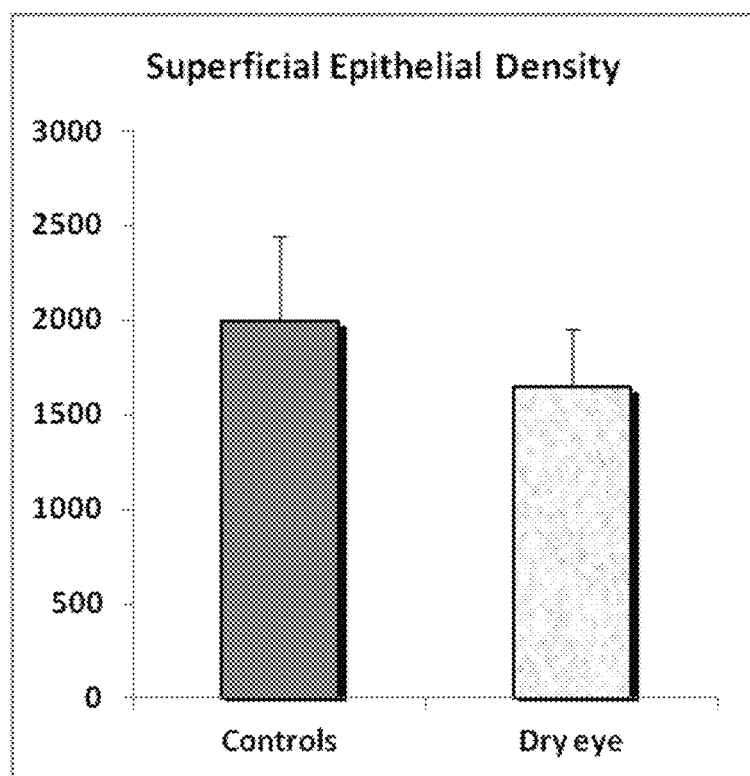
FIG. 28 is a graph showing the corneal superficial epithelial cell density in control subjects and subjects having dry eye syndrome. The error bars represent the standard deviation of the mean.
Figure 29:
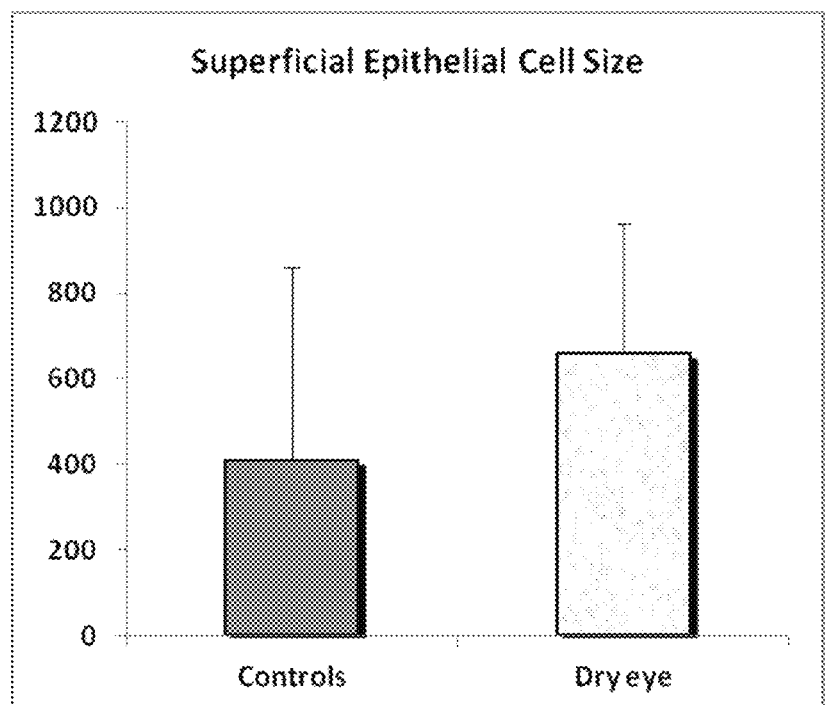
FIG. 29 is a graph showing the corneal superficial epithelial cell size in control subjects and subjects having dry eye syndrome. The error bars represent the standard deviation of the mean.
Figure 30:
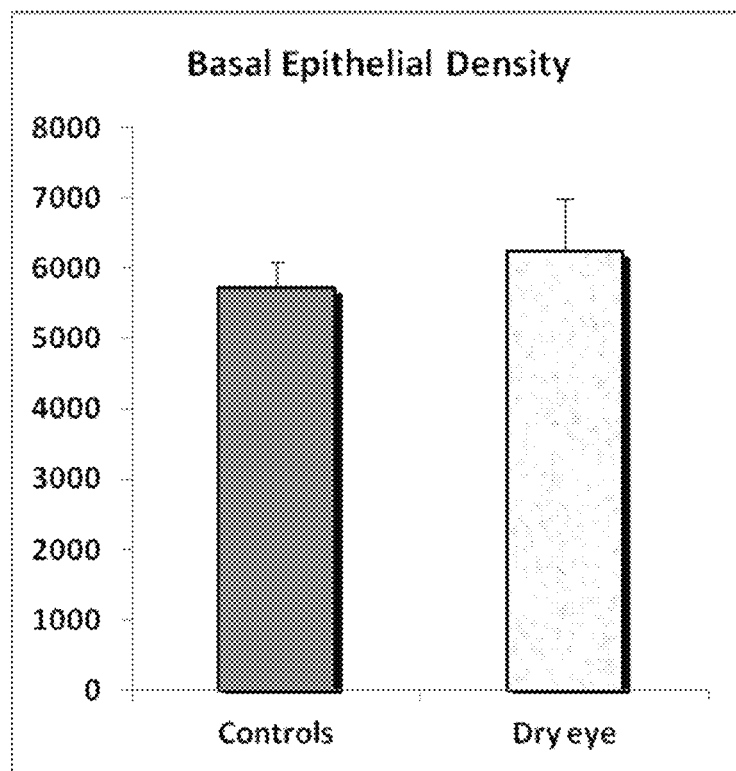
FIG. 30 is a graph showing the corneal basal epithelial density in control subjects and subjects having dry eye syndrome. The error bars represent the standard deviation of the mean.
Figure 31:
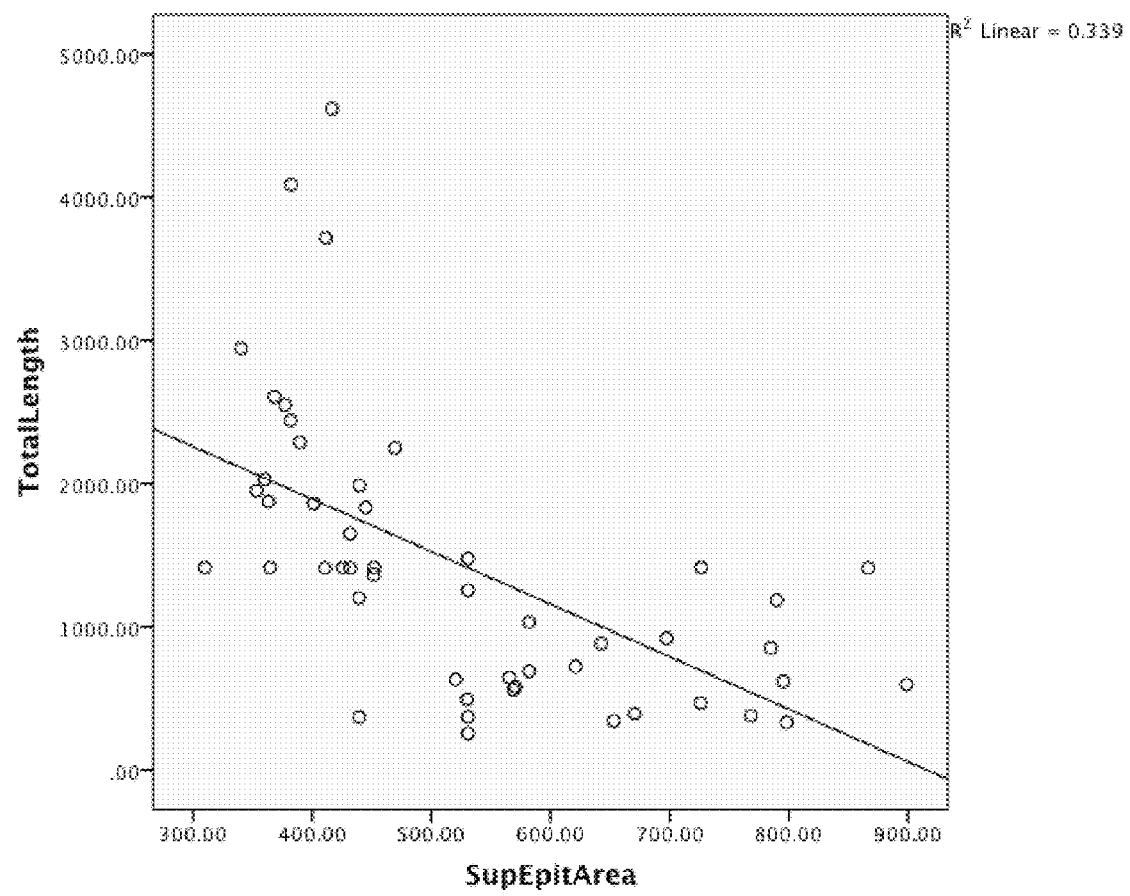
FIG. 31 is a linear regression analysis of the relationship between corneal total nerve length and corneal superficial epithelial cell area.
Figure 32:
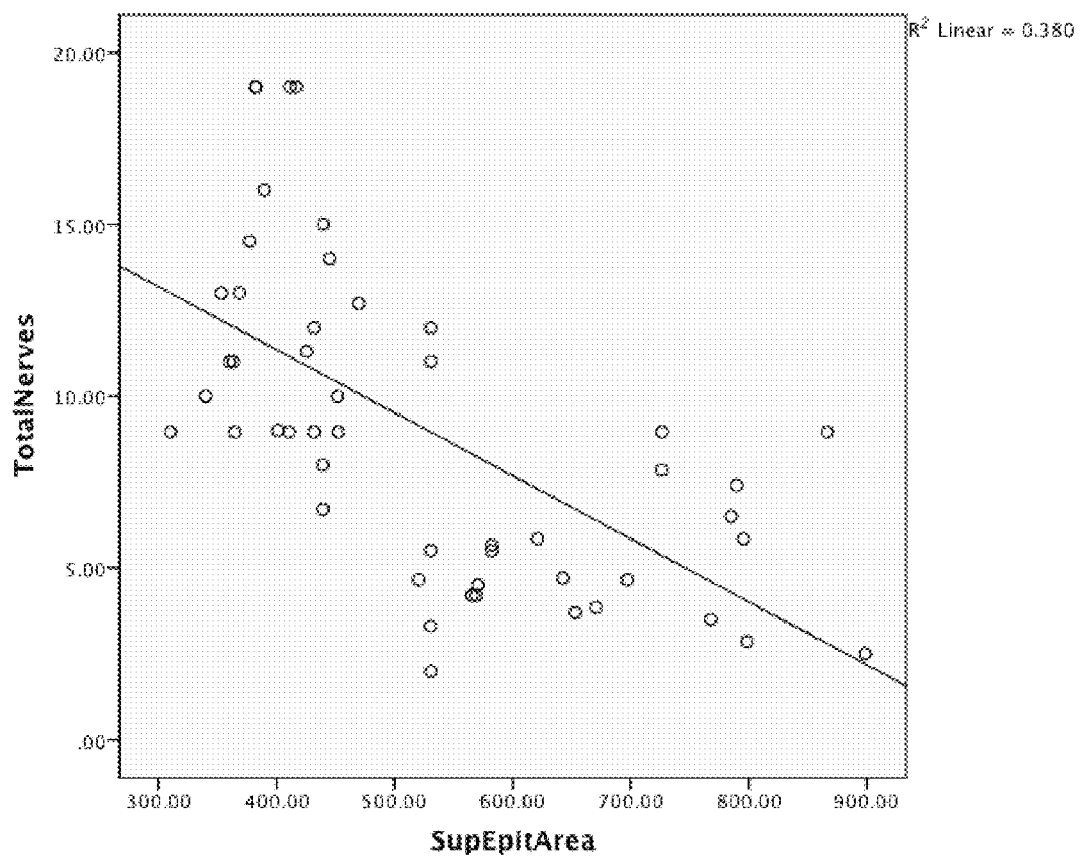
FIG. 32 is a linear regression analysis of the relationship between the total number of corneal nerves and the corneal superficial epithelial area.
Figure 33:
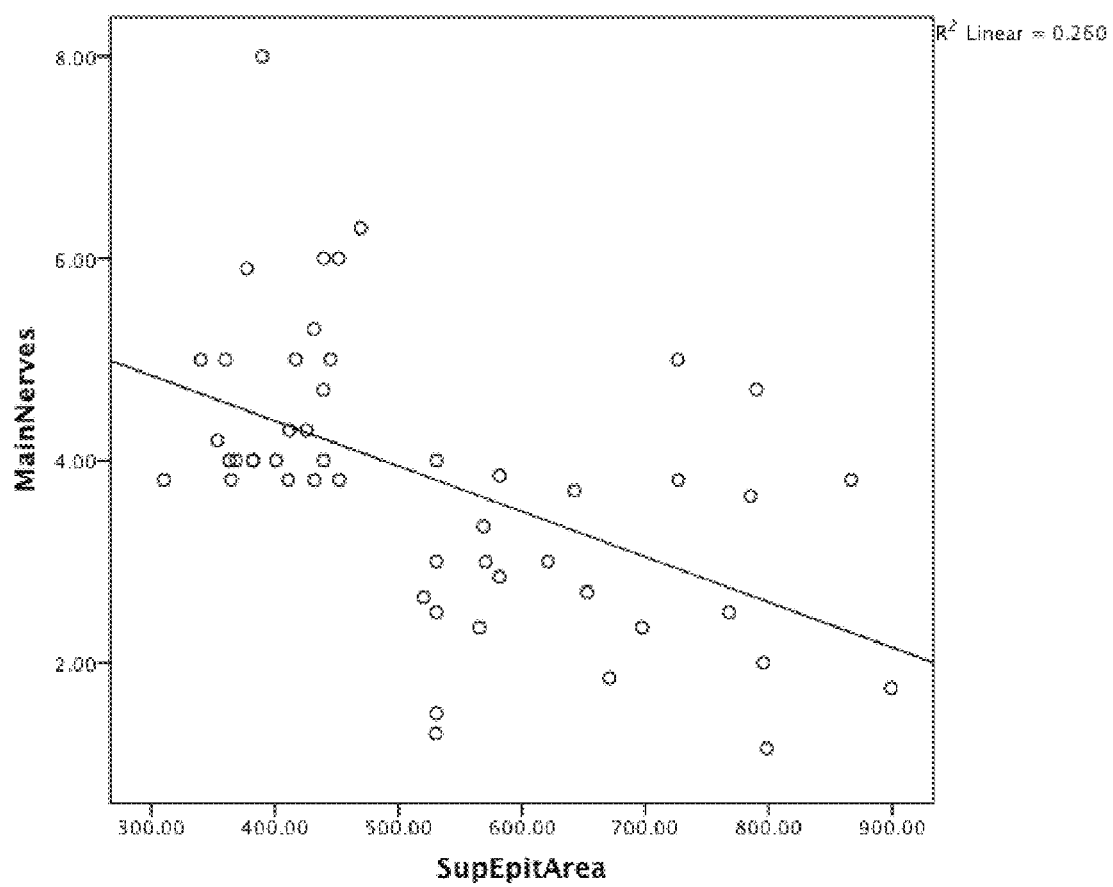
FIG. 33 is a linear regression analysis of the relationship between the number of corneal main nerves and the corneal superficial epithelial cell area.
Figure 34:
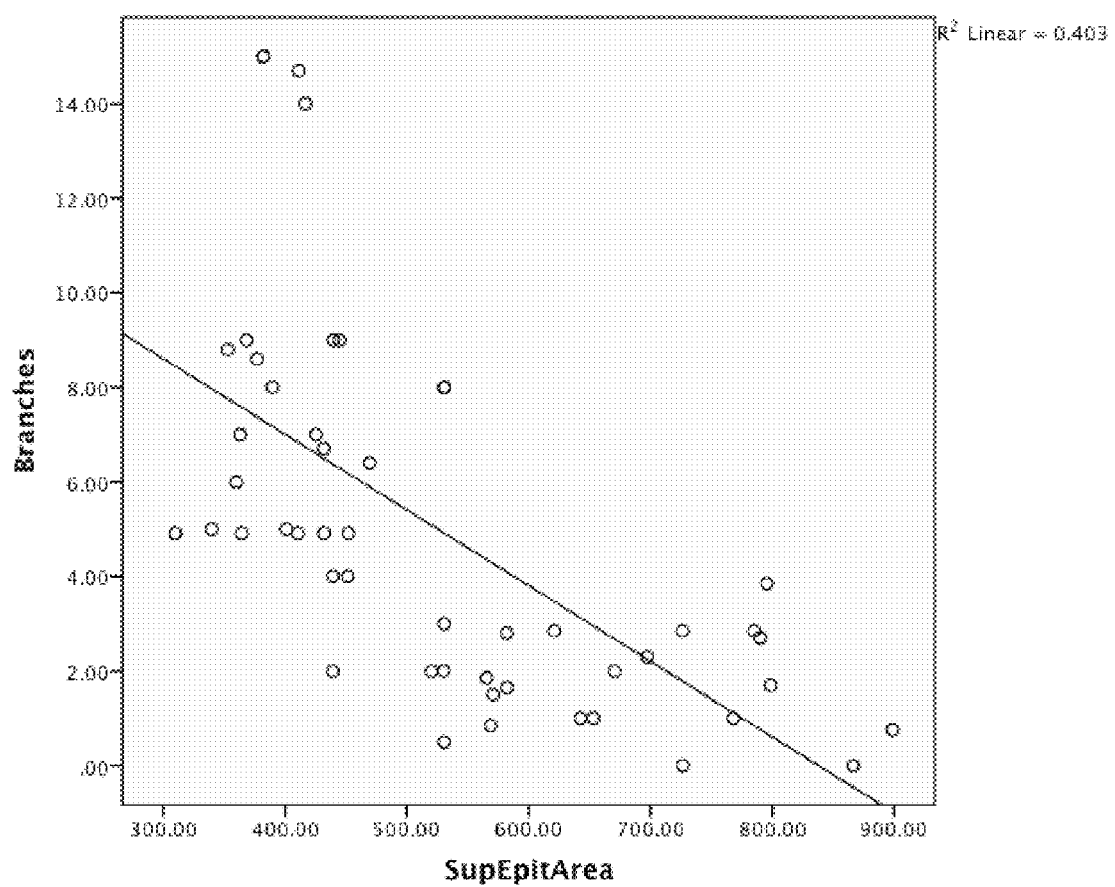
FIG. 34 is a linear regression analysis of the relationship between the number of corneal nerve branches and the corneal superficial epithelial cell area.

Patients with DES had a significant decrease in superficial epithelial cell density (1645.4±302.8 vs. 1993.5±448.9; p=0.003) and an increase in their size (660.8±123.2 vs. 410.7±53.0; p<0.0001) with a higher number of hyperreflective cells (229.0±70.0 vs. 115.6±93.1; p<0.0001) as compared to controls. The basal epithelial cell density was significantly increased in DES patients as compared to controls (6248.5±741.6 vs. 5718.3±367.8; p=0.002) (FIGS. 28-30).

TABLE 2

Corneal epithelial cell parameters and corneal subbasal nerve plexus parameters in control and dry eye syndrome groups.

|  | Control | Dry Eye | p-value |
|---|---|---|---|
| Epithelial cell parameters |  |  |  |
| Superficial epithelial density (cells/mm$^2$) | 1993.5 ± 448.9 | 1645.4 ± 302.8 | *p = 0.003 |
| Superficial epithelial cell size (µm$^2$) | 410.7 ± 53.0 | 660.8 ± 123.2 | *p < 0.001 |
| Hyperreflectivity cells (cells/mm$^2$) | 115.6 ± 93.1 | 229.0 ± 70.0 | *p < 0.001 |
| Basal epithelium (cells/mm$^2$) | 5718.3 ± 367.8 | 6248.5 ± 741.6 | *p = 0.002 |
| Corneal subbasal nerve plexus parameters |  |  |  |
| Total Nerve length (µm/mm$^2$) | 15,690.6 ± 6,695.1 | 5,035.0 ± 2,459.2 | *p < 0.001 |
| (µm/frame) | 2,094.7 ± 893.8 | 672.3 ± 328.3 |  |
| Total number of Nerves (no/frame) | 12.5 ± 3.5 | 5.1 ± 1.9 | *p < 0.001 |
| Main Nerves (no/frame) | 4.6 ± 1.1 | 2.9 ± 1.1 | *p < 0.001 |
| Branching (no/frame) | 7.8 ± 3.4 | 1.8 ± 1.0 | *p < 0.001 |
| Tortuosity | 1.6 ± 0.3 | 1.9 ± 0.7 | p = 0.124 |

Values reported as mean ± standard deviation.
*Statistically significant (p < 0.05) compared to controls.

Pearson correlation was performed to determine significant correlations between the corneal nerves and the epithelial parameters, and to assess associations between the in vivo confocal microscopy findings and the clinical tests performed to evaluate DES, such as corneal fluorescein staining score, TBUT, and Schirmer's test.

Figure 35:
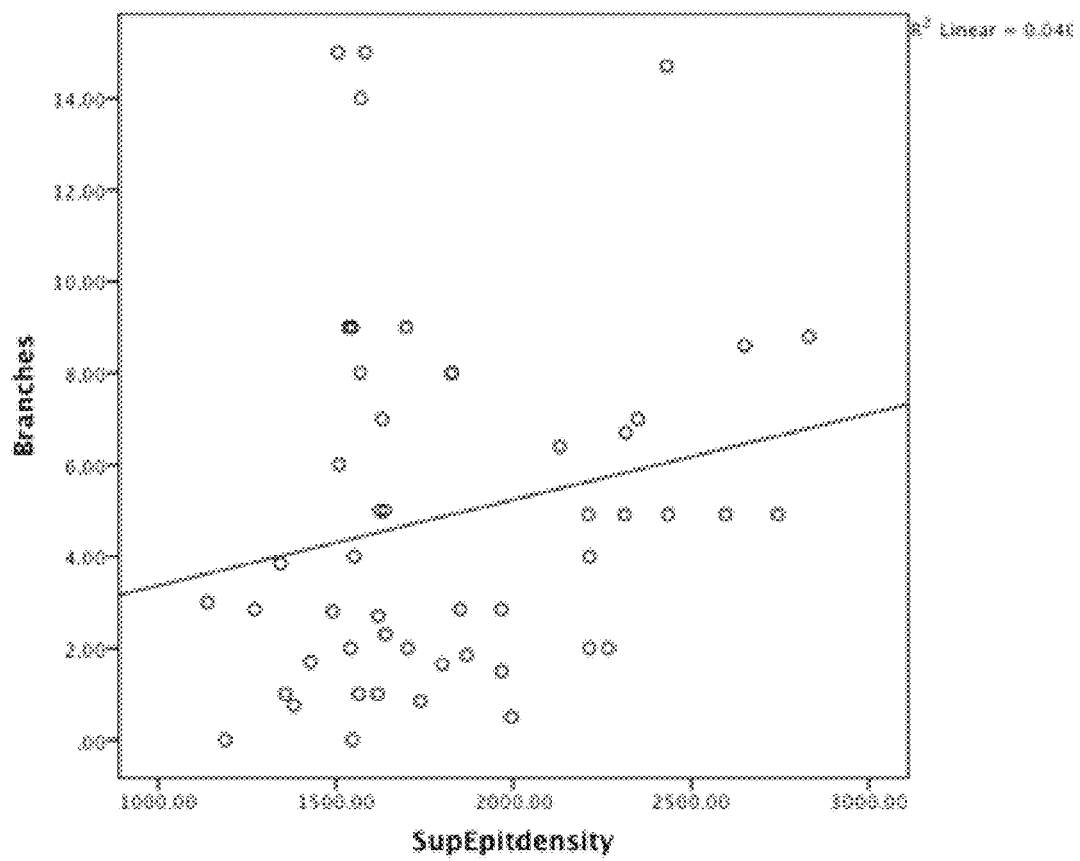
FIG. 35 is a linear regression analysis of the relationship between the number of corneal nerve branches and the corneal superficial cell density.
Figure 36:
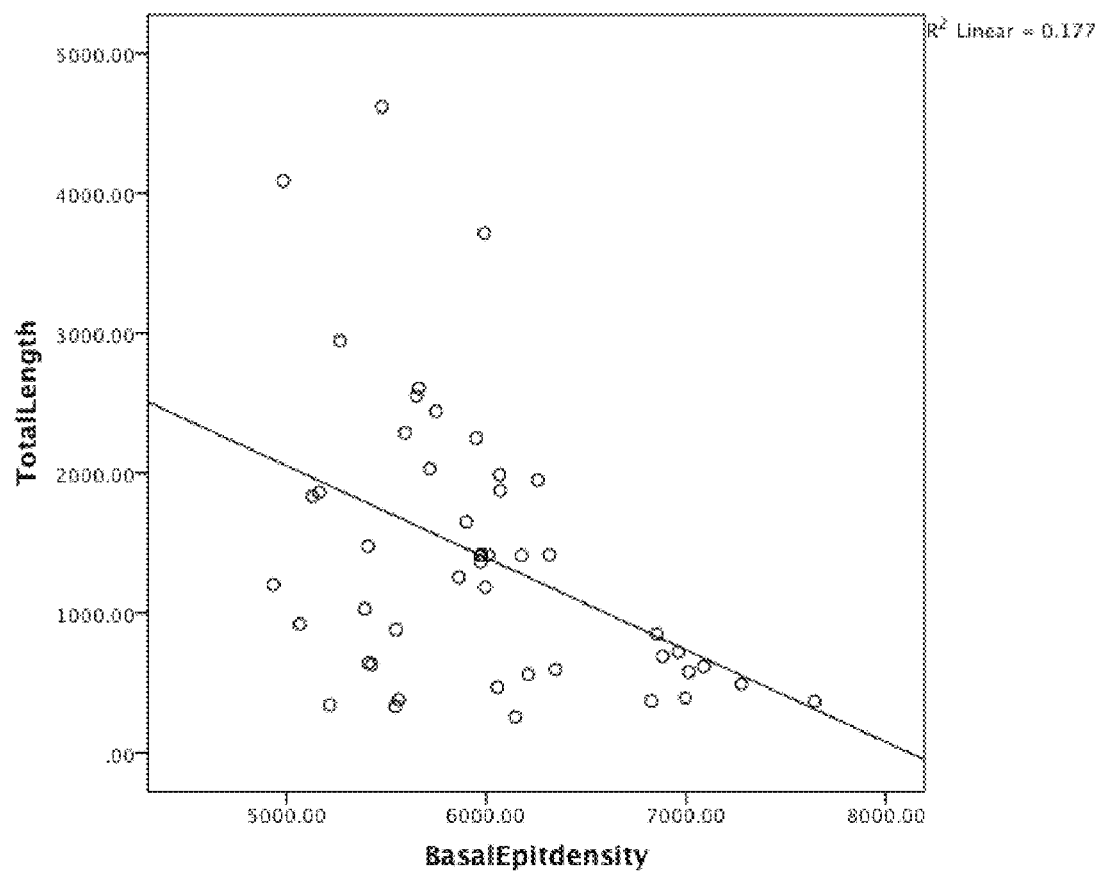
FIG. 36 is a linear regression analysis of the relationship between the total corneal nerve length and the corneal basal epithelial cell density.

There was an inverse correlation between the cell size of the superficial corneal epithelium and some of the corneal nerve parameters (FIGS. 31-34 and 36), and a positive correlation between the number of nerve branches and the superficial epithelial cell density (FIG. 35). Superficial epithelial cell size was significantly correlated to total nerve length (R=−0.71, p<0.0001), total number of nerves (R=−0.68, p<0.0001), main nerve trunks (R=−0.57, p<0.0001) and nerve branches (R=−0.74, p<0.0001). The density of the basal epithelial was also inversely correlated to total nerve length (R=−0.38, p=0.008) (FIG. 36).

Figure 37:
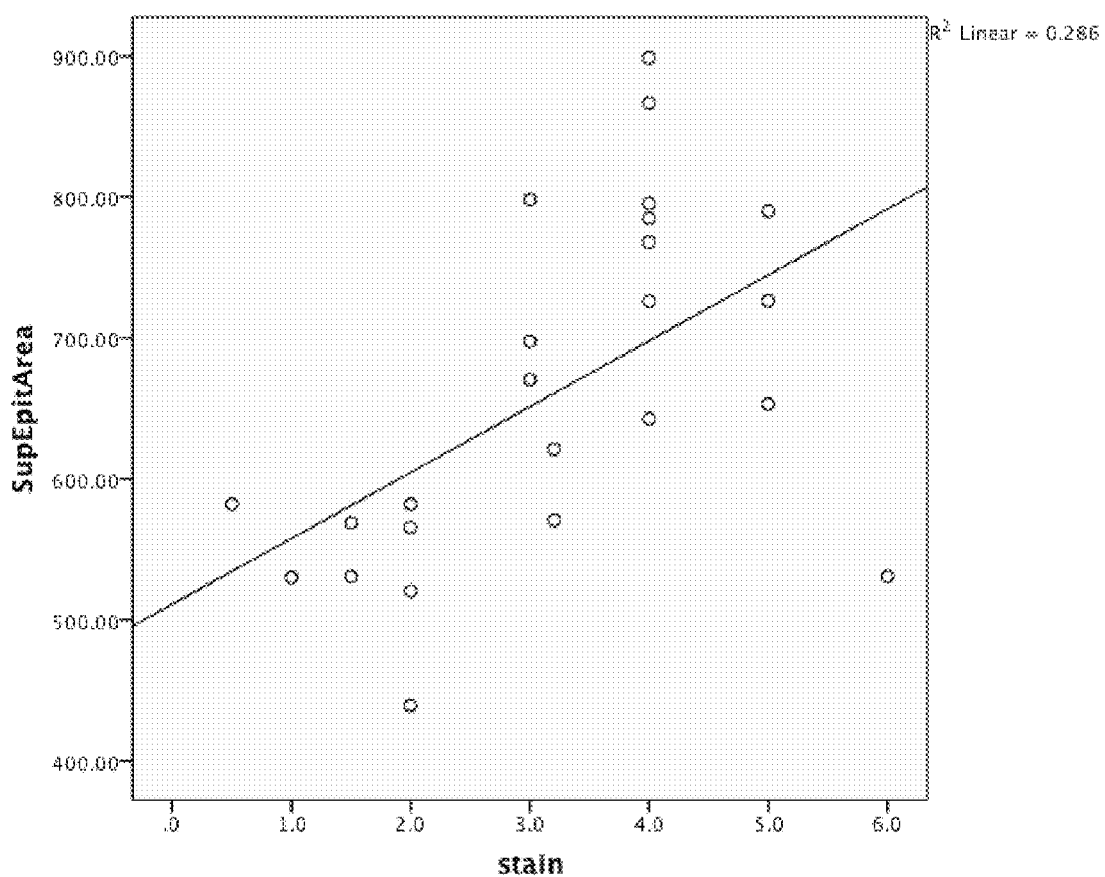
FIG. 37 is a linear regression analysis of the relationship between the corneal subbasal epithelial cell area and fluorescein staining score.
Figure 38:
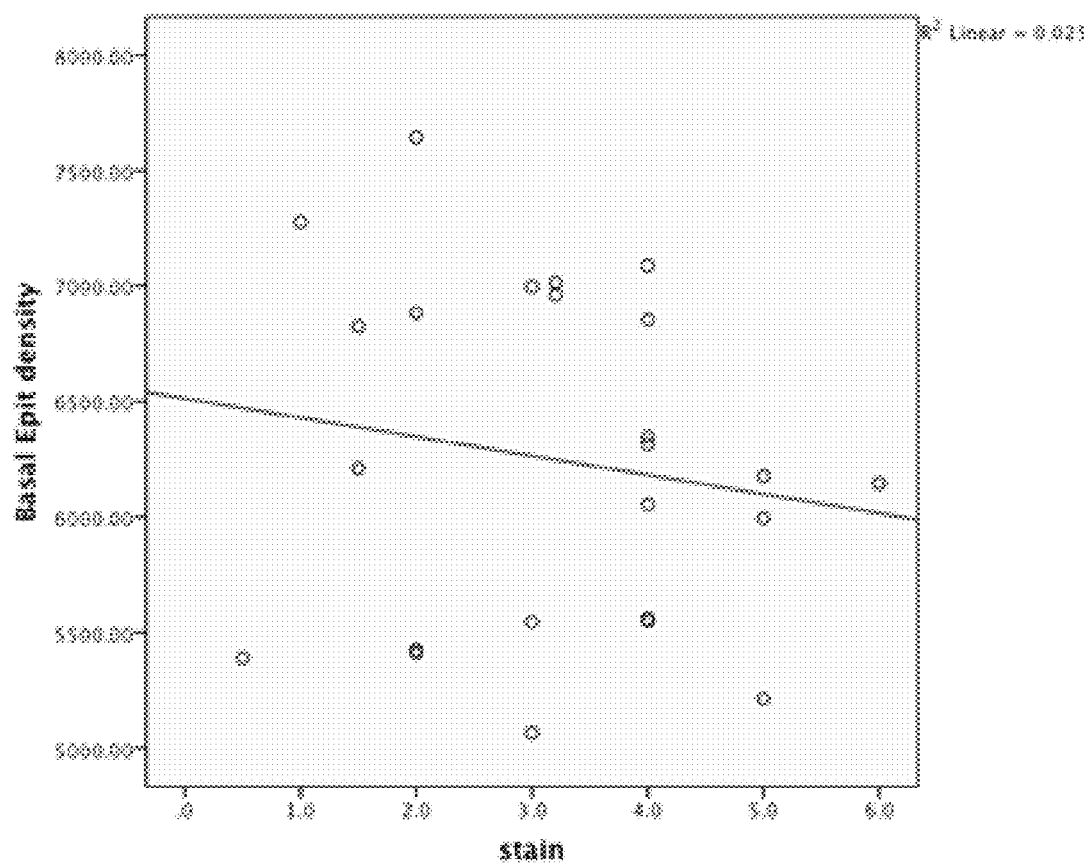
FIG. 38 is a linear regression analysis of the relationship between the corneal basal epithelial cell density and fluorescein staining score.
Figure 39:
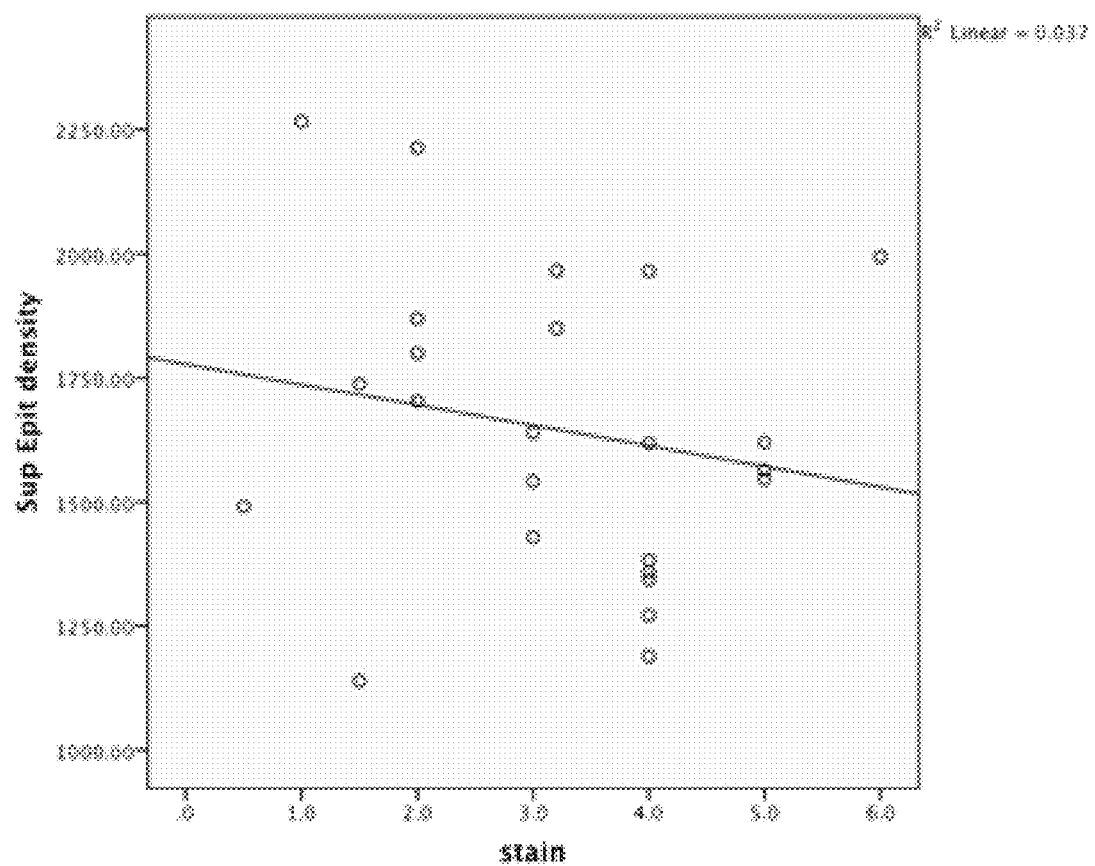
FIG. 39 is a linear regression analysis of the relationship between the corneal superficial epithelial cell density and fluorescein staining score.

In patients with DES, increased corneal fluorescein staining score correlated with an increase in superficial epithelial cell size (R=0.54, p=0.007) (FIG. 37), while increased corneal fluorescein staining score showed an inverse correlation with basal epithelial cell density (FIG. 38) and superficial epithelial cell density (FIG. 39). A correlation was not observed between TBUT and Schirmer's test with the in vivo confocal microscopy findings. These data indicate a number of other optical physical parameters that can also be used to diagnose a subject as having dry eye syndrome.

Figure 40:
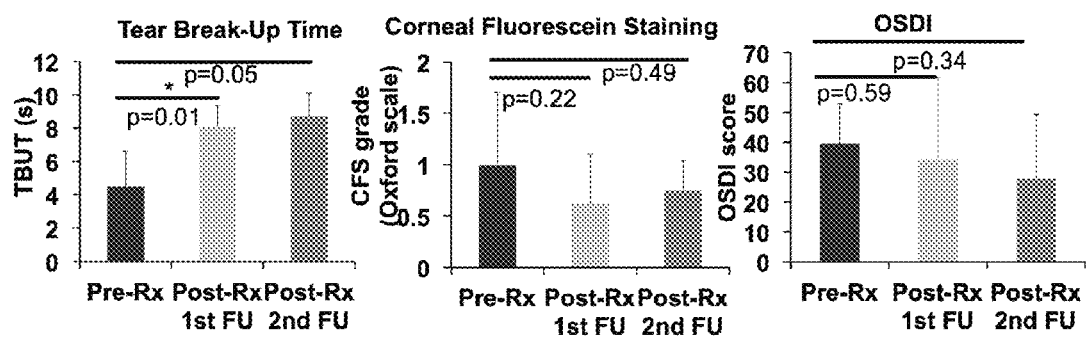
FIG. 40 is a set of three graphs showing the mean TBUT, mean corneal fluorescein staining score, or the mean Ocular Surface Disease Index (OSDI) score determined for subjects having dry eye syndrome at the following time points: before anti-inflammatory treatment (Pre-Rx), at a first follow-up visit following initiation of anti-inflammatory treatment (2.3±0.9 months after initiation of treatment), and at a second follow-up visit following initiation of anti-inflammatory treatment (4.8±1.8 months following initiation of anti-inflammatory treatment).
Figure 41:
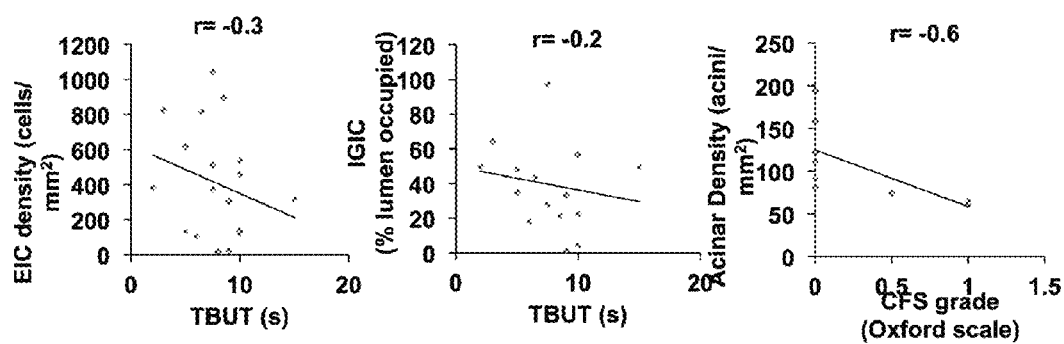
FIG. 41 is set of three linear regression analyses, from left to right, of the relationship between corneal epithelium immune cell density (cells/mm$^2$) and TBUT, the relationship between intraglandular immune cells (% lumen occupied) and TBUT, and the relationship between acinar density (acini/mm$^2$) and corneal fluorescein staining score (Oxford scale) in subjects having dry eye syndrome.
Figure 43:
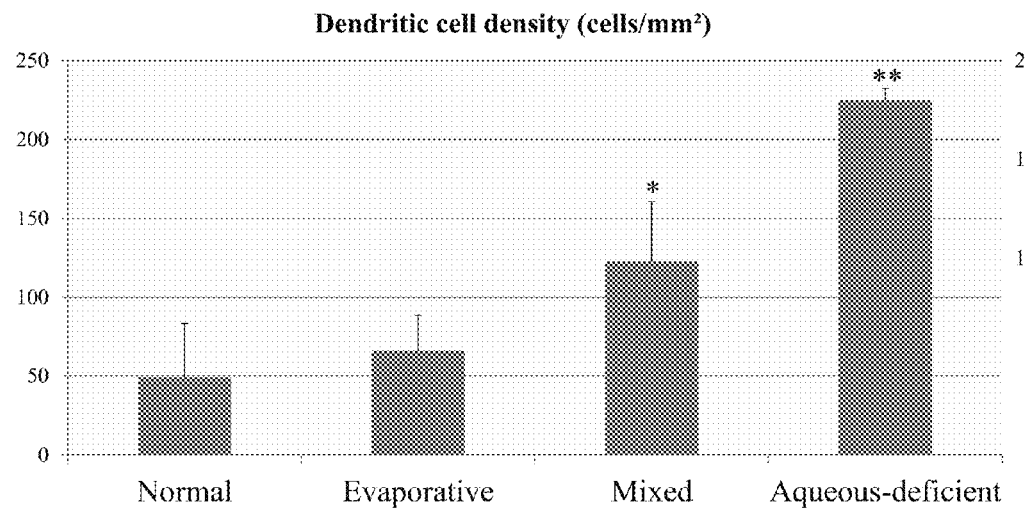
FIG. 43 is a graph of the mean dendritic cell corneal density (cells/mm$^2$) for eyes from normal subjects (Normal), eyes from subjects having evaporative dry eye syndrome (Evaporative), eyes from subjects having mixed mechanism dry eye syndrome (Mixed), and eyes from subjects having aqueous-deficient dry eye syndrome (Aqueous-deficient). *, $p<0.05$; **, $p<0.01$.
Figure 44:
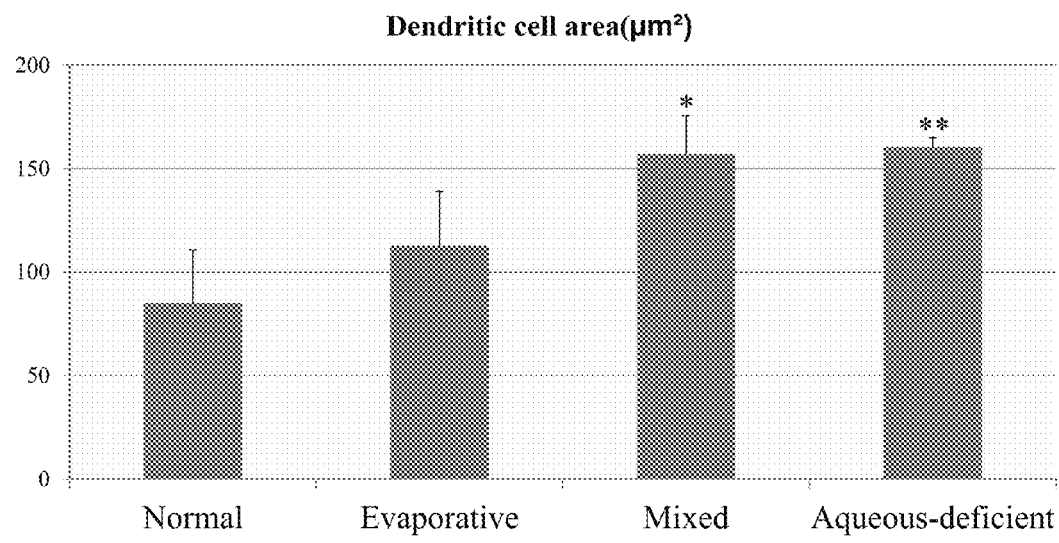
FIG. 44 is a graph of the mean dendritic cell area (μm) in the corneas of eyes from normal subjects (Normal), eyes from subjects having evaporative dry eye syndrome (Evaporative), eyes from subjects having mixed mechanism dry eye syndrome (Mixed), and eyes from subjects having aqueous-deficient dry eye syndrome (Aqueous-deficient). *, $p<0.05$; **, $p<0.01$.
Figure 45:
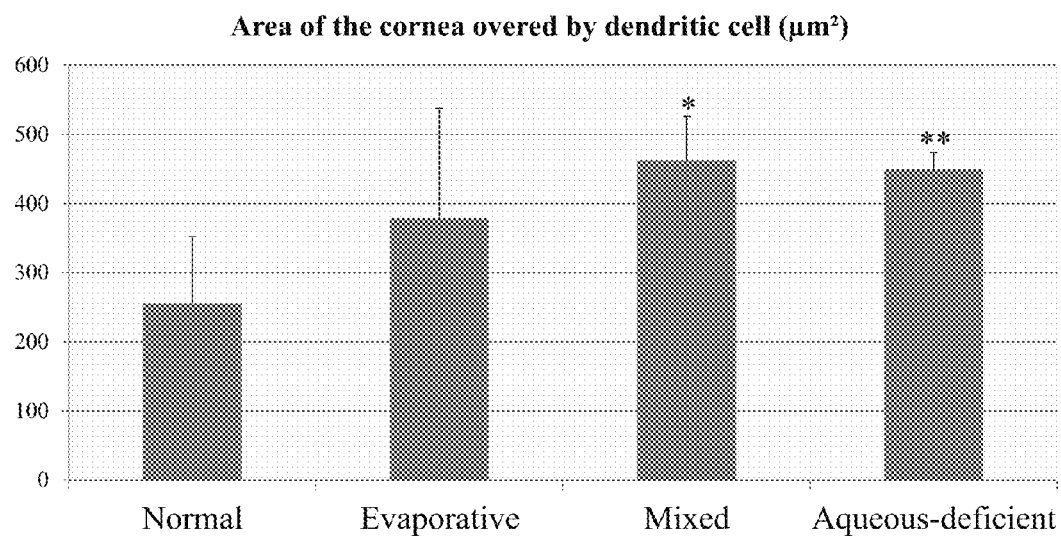
FIG. 45 is a graph of the mean area of the cornea covered by dendritic cells (μm$^2$) for eyes from normal subjects (Normal), eyes from subjects having evaporative dry eye syndrome (Evaporative), eyes from subjects having mixed mechanism dry eye syndrome (Mixed), and eyes from subjects having aqueous-deficient dry eye syndrome (Aqueous-deficient). *, $p<0.05$; **, $p<0.01$.
Figure 46:
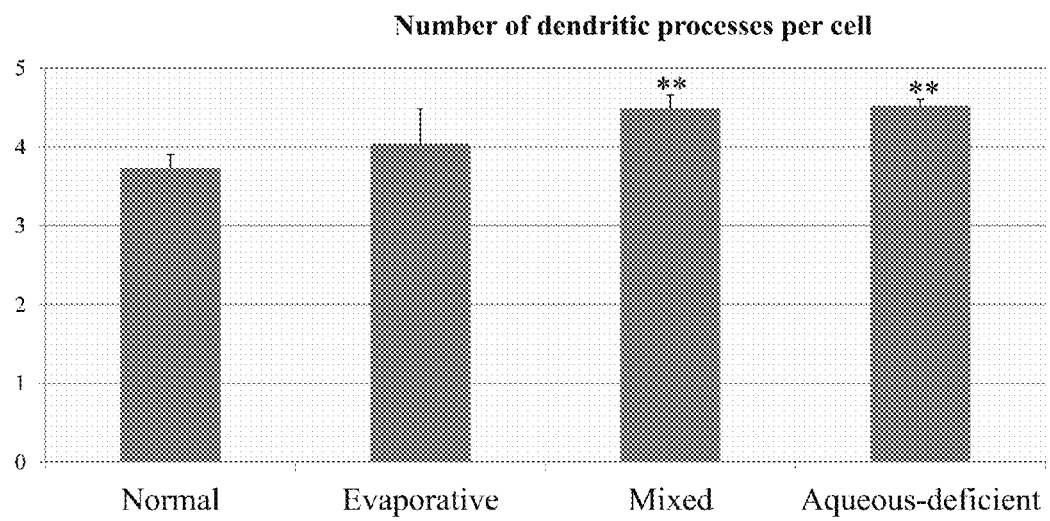
FIG. 46 is a graph of the mean number of dendritic processes per cell in the corneas of eyes from normal subjects (Normal), eyes from subjects having evaporative dry eye syndrome (Evaporative), eyes from subjects having mixed mechanism dry eye syndrome (Mixed), and eyes from subjects having aqueous-deficient dry eye syndrome (Aqueous-deficient). *, $p<0.05$; **, $p<0.01$.

The TBUT, corneal fluorescein staining score, and Ocular Surface Disease Index (OSDI) Questionnaire Score was determined for the subjects having dry eye syndrome before anti-inflammatory treatment (Pre-Rx), at a first follow-up visit following initiation of anti-inflammatory treatment (2.3±0.9 months after initiation of treatment), and at a second follow-up visit following initiation of anti-inflammatory treatment (4.8±1.8 months following initiation of anti-inflammatory treatment) (FIG. 40). Pearson correlation was performed to assess the correlations between the immune cell parameters and the acinar density and the clinical tests performed to evaluate dry eye syndrome, such as TBUT and corneal fluorescein staining. The resulting data show a negative correlation between corneal epithelial immune cell density and TBUT, a negative correlation between intraglandular immune cell concentration (% lumen occupied) and TBUT, and a negative correlation between acinar density and corneal fluorescein staining (FIG. 41). These data further indicate that corneal epithelial immune cell density, intraglandular immune cell concentration, and acinar density can be used to assess the efficacy of treatment of dry eye disease in a subject.

Example 6. Immune Cell Alternations in the Cornea and the Effect of Anti-Inflammatory Treatment on Different Subtypes of Dry Eye Syndrome These experiments were performed to determine if the alternations in corneal immune cells occur in different subtypes of dry eye syndrome, and if subjects having these different subtypes of dry eye syndrome are responsive to anti-inflammatory treatment.

Materials and Methods

This was a retrospective, case-control study of sixty-six eyes of patients having dry eye syndrome, and 28 normal eyes. The exclusion criteria for both the case and control groups included diabetes mellitus, refractive surgery, and corneal infection. Based on the dry eye subtype, the patients were divided into three groups: aqueous-deficient, evaporative, and mixed mechanism. Laser in vivo confocal microscopy (as described herein) using a HRT 3 and Cornea Rostock Module was performed on the central cornea of patients with dry eye syndrome and controls (using the methods described herein). Three representative images (n=3) from each eye were analyzed in a blinded fashion for: dendritic cell density defined as hyperreflective dendriform cells, dendritic cell size defined as the average area of each dendritiform cell, surface of the cornea covered by dendritic cells, and the number of dendritic processes per cell. Exemplary in vivo confocal microscopic images showing the central corneal of an eye from a normal subject, an eye from a subject having evaporative dry eye syndrome, an eye from a subject having mixed mechanism dry eye syndrome, and an eye from a subject having aqueous-deficient dry eye syndrome are shown in FIGS. 42A-D.

The resulting data show that patients with aqueous-deficient dry eye syndrome (density: p=0.001; cell area: p=0.0007; covered area; p=0.009; number of dendrites: p=0.0001) and mixed dry eye syndrome patients (density: p=0.03; cell area: p=0.01; covered area: p=0.04; number of dendrites: p=0.0003), but not evaporative dry eye syndrome patients (density: p=0.48; cell area: 0.31; area covered: p=0.45; number of dendrites: p=0.50), had significant increases for all four parameters as compared to controls (FIGS. 43-46).

Figure 47:
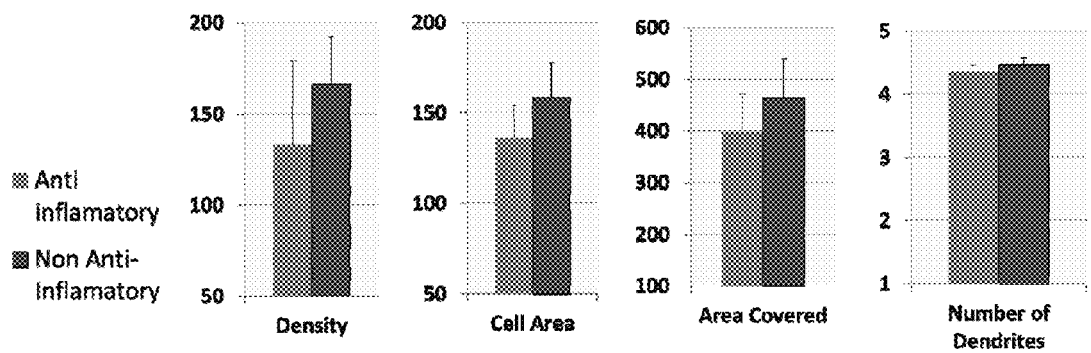
FIG. 47 is a set of four graphs showing the mean immune cell density (cells/mm$^2$), mean immune cell area (μm$^2$), mean immune cell area covered (μm$^2$), and mean number of dendrites (dendrites/cell) of immune cells present in the cornea of subjects having dry eye syndrome that are either receiving anti-inflammatory treatment (Anti-inflammatory) or not receiving an anti-inflammatory treatment (Non Anti-inflammatory).

The cornea immune cell density (cells/mm$^2$) and area (μm$^2$) was determined in the eyes of the subjects having dry eye syndrome receiving or not receiving anti-inflammatory treatment. The data show that dry eye syndrome patients on anti-inflammatory therapy (AIT) had a 20% lower dendritic cell density and a 15% decrease in the dendritic cell size and area of the cornea covered by dendritic cells compared to dry eye syndrome patients not receiving anti-inflammatory therapy (AIT) (FIG. 47). In sum, these data indicate that in vivo confocal microscopy enables the detection of significant dry eye syndrome-induced changes in immune cells in the cornea in subjects having different subtypes of dry eye syndrome, and show that dendritic cell density and morphology can serve as a parameter to assess the severity of dry eye syndrome and the efficacy of treatment of dry eye syndrome.

Example 7. Use of Confocal Microscopy to Determine Efficacy of Autologous Serum Treatment in Subjects Having Dry Eye Syndrome This set of experiments was performed to determine whether in vivo confocal microscopy can be used to determine the efficacy of treatment of dry eye syndrome in subjects following treatment with autologous serum. Specifically, the study was designed to evaluate the effect of autologous serum eye drops on the corneal subbasal nerve plexus for the treatment of severe dry eye syndrome.

Central corneal images were collected using in vivo confocal microscopy as described herein (using an scanning laser in vivo confocal microscope with the Heidelberg Retina Tomograph 3 with the Rostock Cornea Module (Heidelberg Engineering GmbH) in each subject at baseline and at each follow-up visit. The autologous serum was prepared by obtaining a venous peripheral blood sample from the subject to be treated, and centrifuging the sample for 10 minutes at 3000 RPM. The resulting supernatant serum was removed and diluted to a concentration of 20% serum in balanced saline solution. Five-mL aliquots of the autologous serum solution were placed into sterile dropper bottles and stored until use at −2° C. Each bottle was used for 1 week, with 1 drop administered to each eye 6 to 8 times a day, and stored during weekly use at 6° C.

One eye from each treated subject was randomly selected and three representative images of the central corneal nerve plexus were analyzed starting from baseline to the last follow-up visit. In each obtained image, the number of nerves, the length of the nerves, number of main nerve trunks, and the number of nerve branches were determined. These parameters were analyzed by two masked observers using the Image J software (NIH). The results were subjected to statistical analysis using the Stata Software package 11.2 (T-test, multivariate and logistic regression analysis). A total of 57 patients with severe dry eye syndrome, and unresponsive to maximal conventional therapy were included in this study, and were compared to a group of normal controls. The demographics of the dry eye syndrome patients and the healthy (normal) control group are shown in Tables 3 and 4 below.

TABLE 4

| Demographics of the Healthy (Normal) Control Group | |
|---|---|
| Number | 25 |
| Age (years) | 33.1 ± 7.6 |
| Range (years) | 22-60 |
| Sex (M:F)% | 10(50%):10(50%) |

Figure 48:
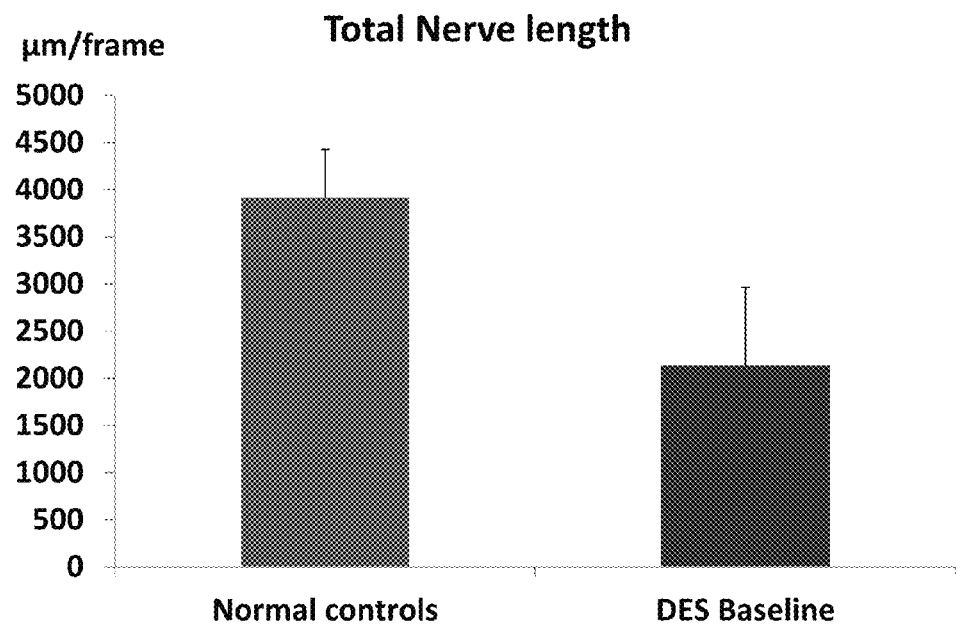
FIG. 48 is a graph of the mean total nerve length (μm/frame) detected in the cornea of normal control patients and patients having dry eye syndrome at baseline (prior to treatment with autologous serum) (*, $p<0.001$).
Figure 49:
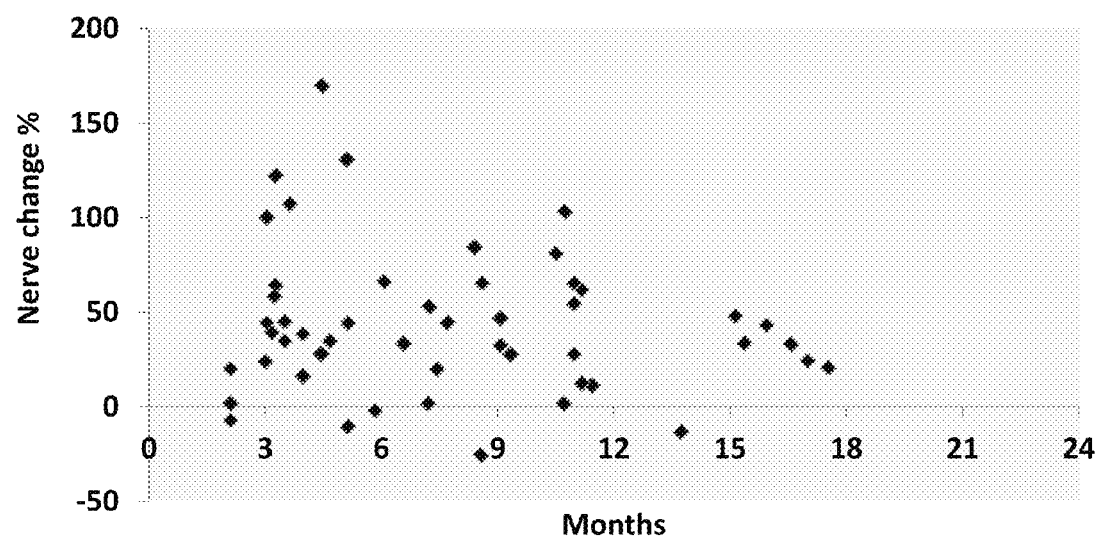
FIG. 49 is a graph of the mean percent change in corneal nerves over time in patients having dry eye syndrome following the initiation of treatment with autologous serum.
Figure 50:
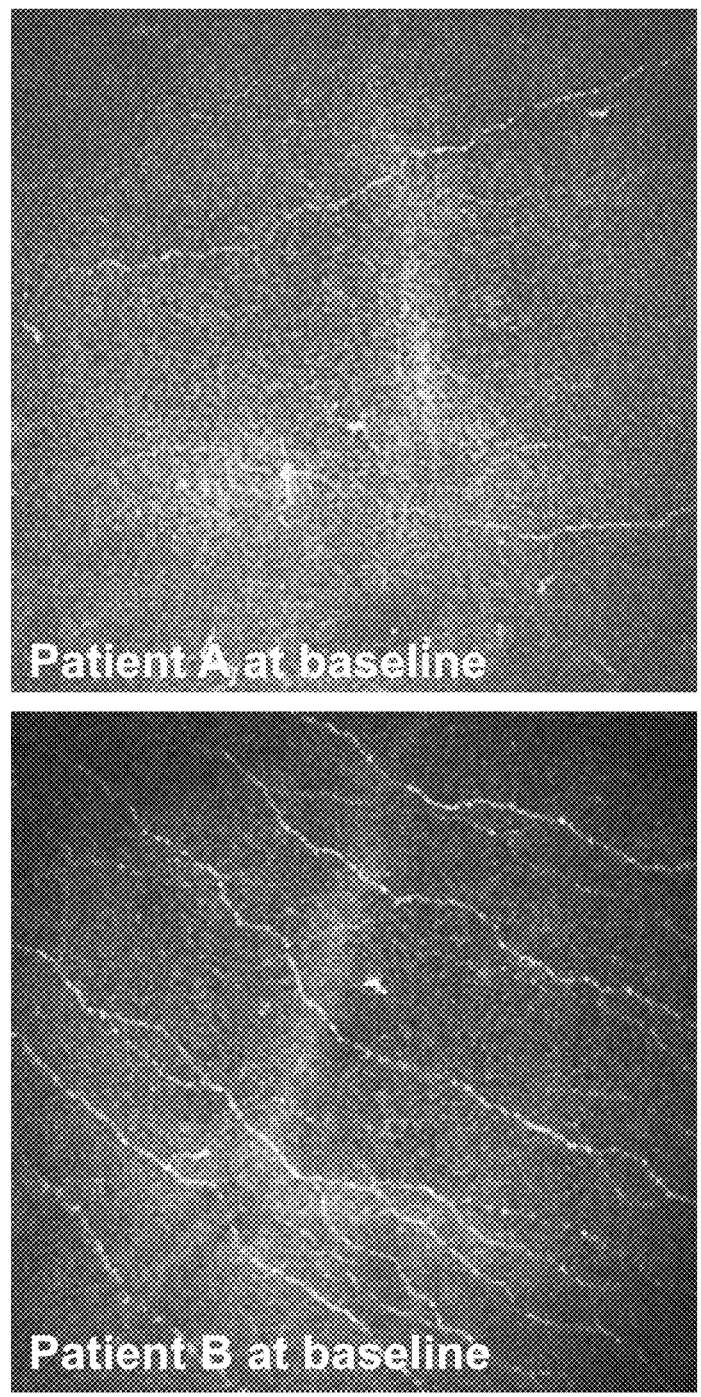
FIG. 50 is a set of two in vivo confocal microscopic images from two different subjects having dry eye syndrome at baseline (prior to treatment with autologous serum).

Prior to treatment, the corneal subbasal nerve plexus (as assessed by determining the total nerve length) was significantly decreased in dry eye syndrome patients as compared to normal controls (FIG. 48; *, p<0.001). An increase in the number of corneal nerves was detected as early as 3 months after the initiation of treatment with autologous serum as compared to the number of corneal nerves detected in the same patients prior to treatment with autologous serum (FIG. 49). It was also observed that the nerve plexus varied among the dry eye patients at baseline (prior to treatment with autologous serum) (FIG. 50). After

TABLE 5

Demographics of Dry Eye Syndrome Patients using Autologous Serum Drops

Figure 51:
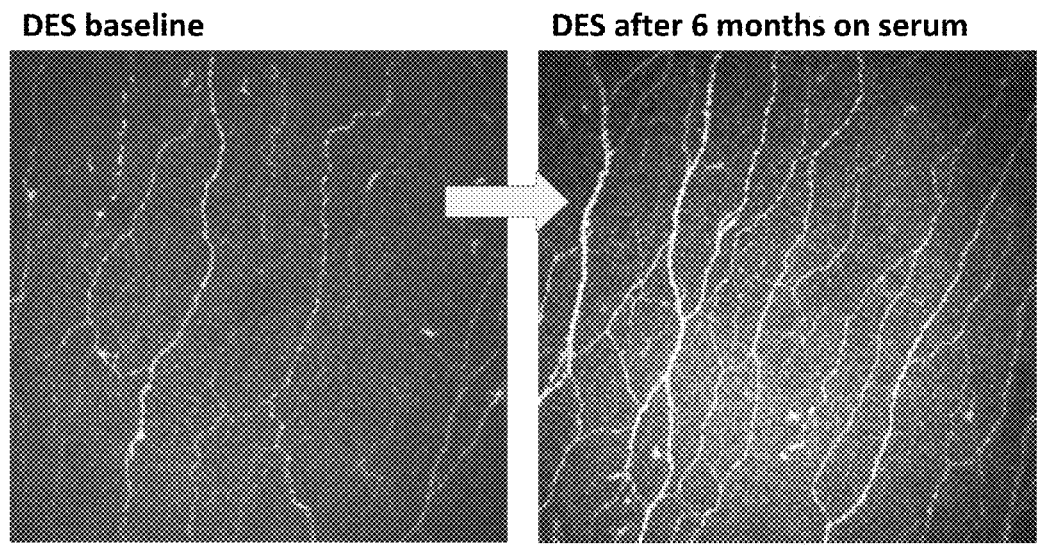
FIG. 51 is a set of two in vivo confocal microscopic images: one showing the cornea of a subject having dry eye syndrome at baseline (prior to treatment with autologous serum) (left), and one showing the cornea of the same subject following 6 months of treatment with autologous serum (right).
Figure 52:
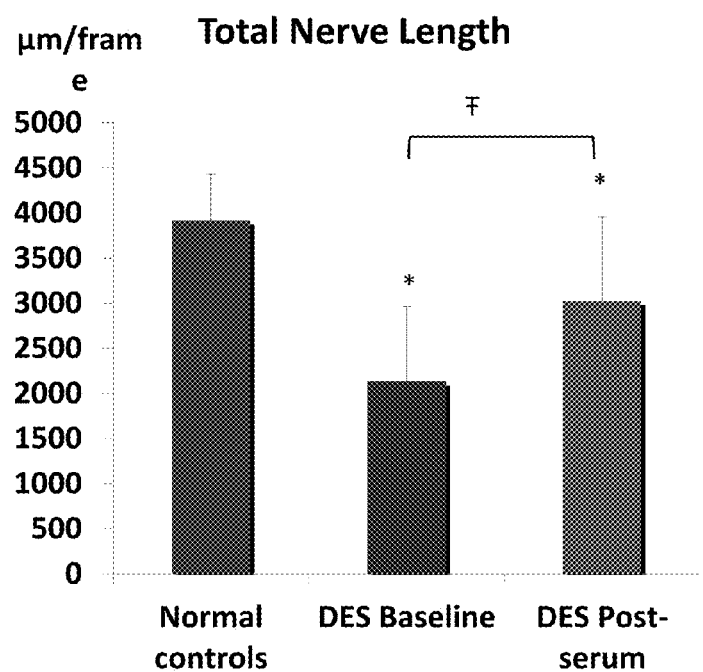
FIG. 52 is a graph showing the mean total nerve length (μm/frame) in the corneas of normal control subjects (Normal controls), corneas of patients having dry eye syndrome at baseline (prior to treatment with autologous serum) (DES Baseline), and corneas of patients having dry eye syndrome after treatment with autologous serum (DES Post-serum) (▼, $p<0.001$; *, $p<0.001$).
Figure 53:
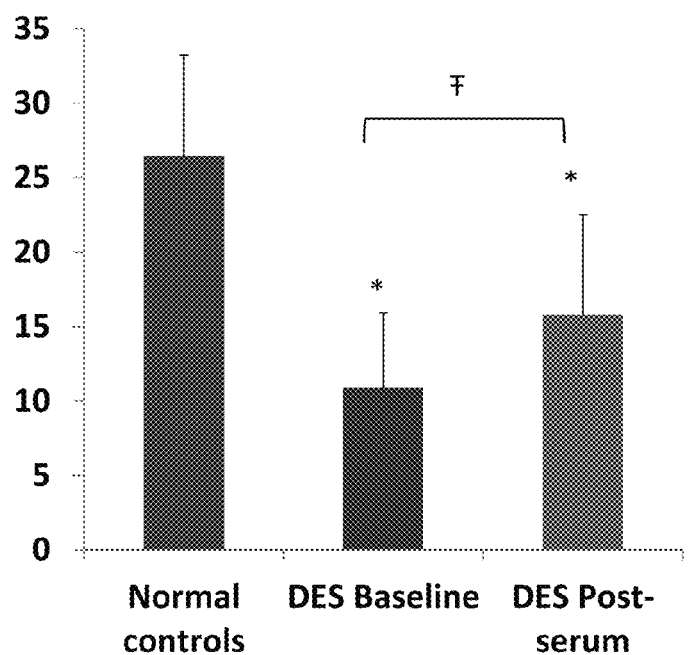
FIG. 53 is a graph showing the mean total nerve number in the corneas of normal control subjects (Normal controls), corneas of patients having dry eye syndrome at baseline (prior to treatment with autologous serum) (DES Baseline), and corneas of patients having dry eye syndrome after treatment with autologous serum (DES Post-serum) (▼, $p<0.001$; *, $p<0.001$).
Figure 54:
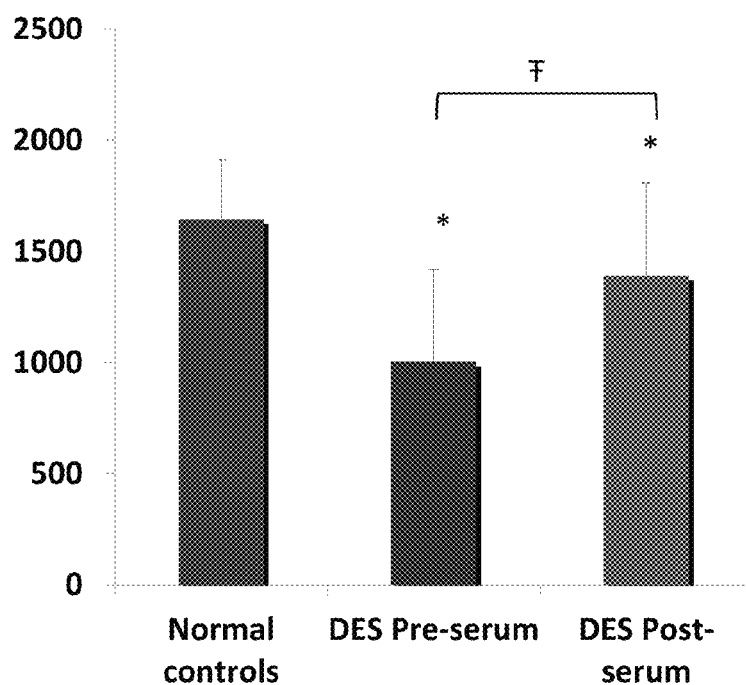
FIG. 54 is a graph showing the mean main nerve trunk length (μm/frame) in the corneas of normal control subjects (Normal controls), corneas of patients having dry eye syndrome at baseline (prior to treatment with autologous serum) (DES Baseline), and corneas of patients having dry eye syndrome after treatment with autologous serum (DES Post-serum) (✝, p<0.001; *, p<0.001).
Figure 55:
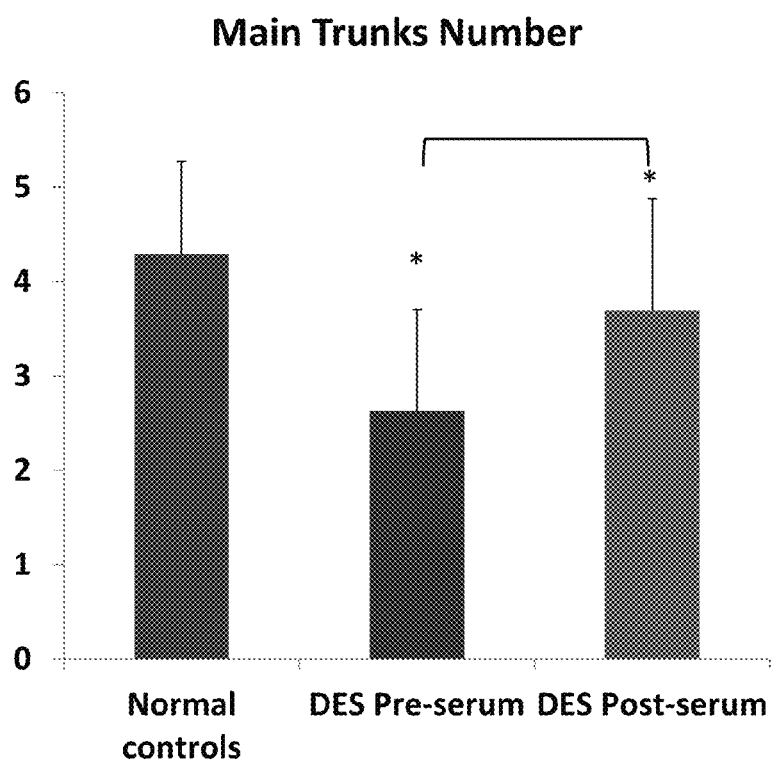
FIG. 55 is a graph showing the mean main nerve trunk number in the corneas of normal control subjects (Normal controls), corneas of patients having dry eye syndrome at baseline (prior to treatment with autologous serum) (DES Baseline), and corneas of patients having dry eye syndrome after treatment with autologous serum (DES Post-serum) (✝, p<0.001; *, p<0.001).
Figure 56:
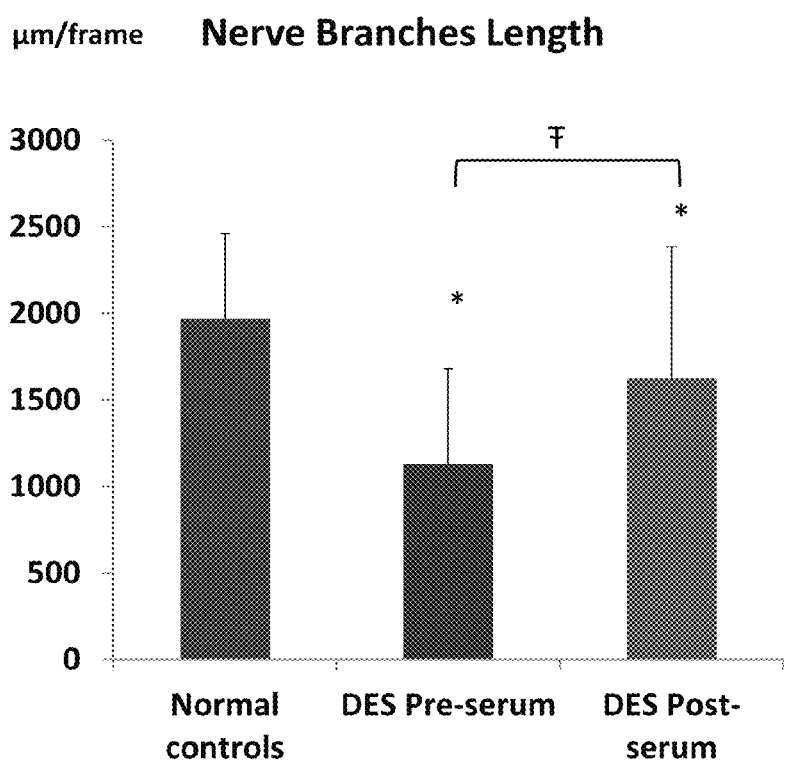
FIG. 56 is a graph of the mean nerve branch length in the corneas of normal control subjects (Normal controls), corneas of patients having dry eye syndrome at baseline (prior to treatment with autologous serum) (DES Baseline), and corneas of patients having dry eye syndrome after treatment with autologous serum (DES Post-serum) (✝, p<0.001; *, p<0.001).
Figure 57:
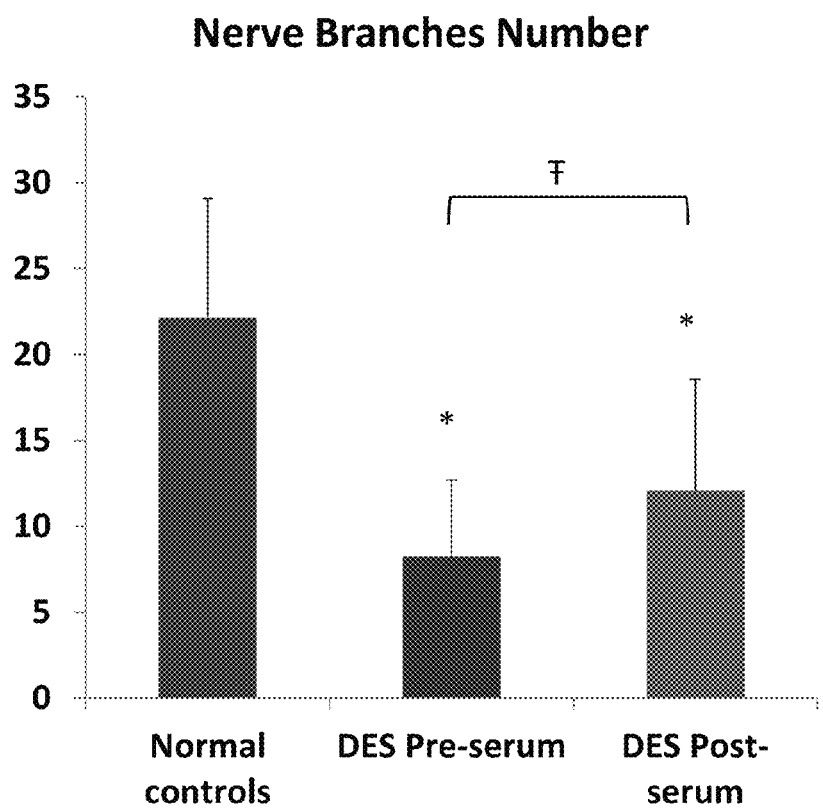
FIG. 57 is a graph of the mean nerve branch number in the corneas of normal control subjects (Normal controls), corneas of patients having dry eye syndrome at baseline (prior to treatment with autologous serum) (DES Baseline), and corneas of patients having dry eye syndrome after treatment with autologous serum (DES Post-serum) (✝, p<0.001; *, p<0.001).
Figure 58:
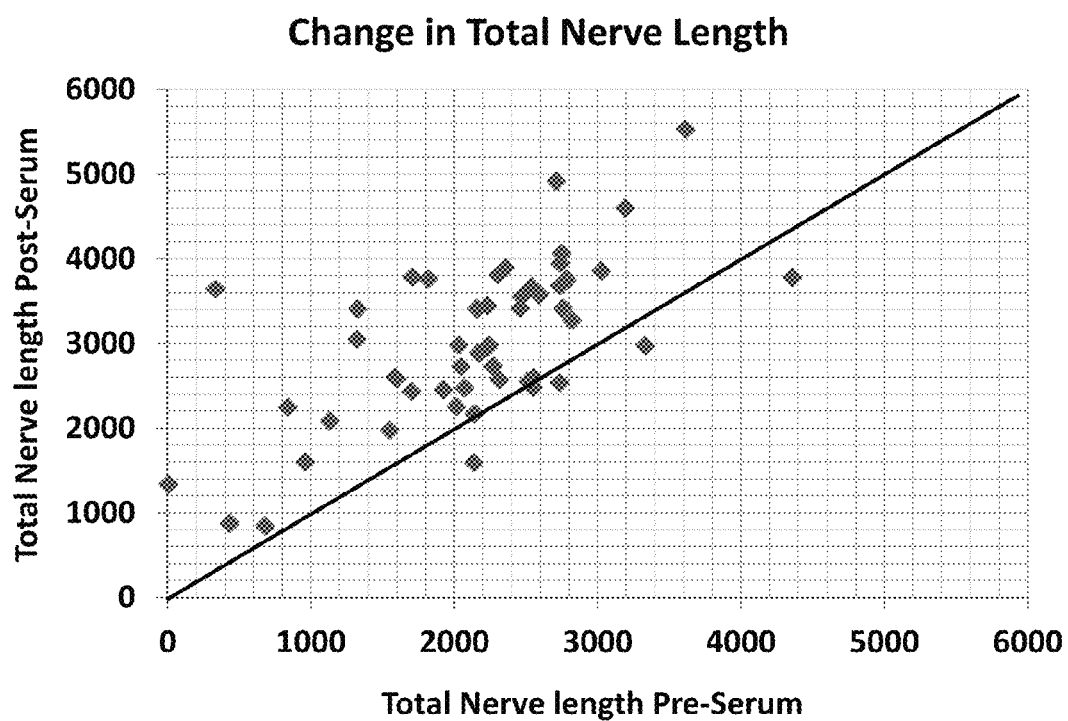
FIG. 58 is a linear regression comparing the total nerve length in patients having dry eye syndrome after treatment with autologous serum (Post-serum) to the total nerve length in the same set of patients at baseline (prior to treatment with autologous serum; Pre-Serum).
Figure 59:
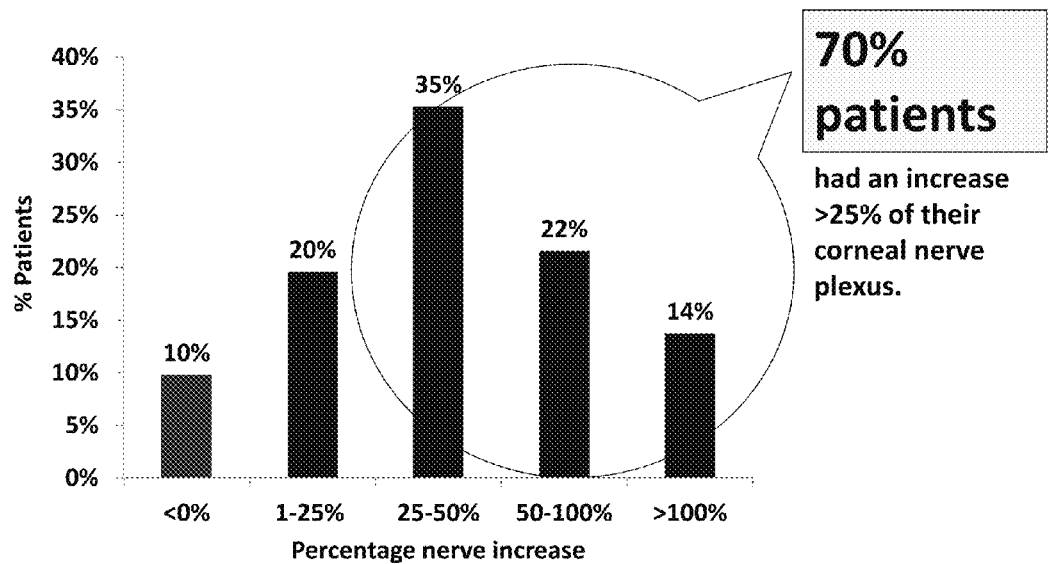
FIG. 59 is a graph showing the percentage of patients having dry eye syndrome that were treated with autologous serum that achieved a specific percentage of nerve increase following treatment with autologous serum (as compared to the baseline value for each patient).
Figure 60:
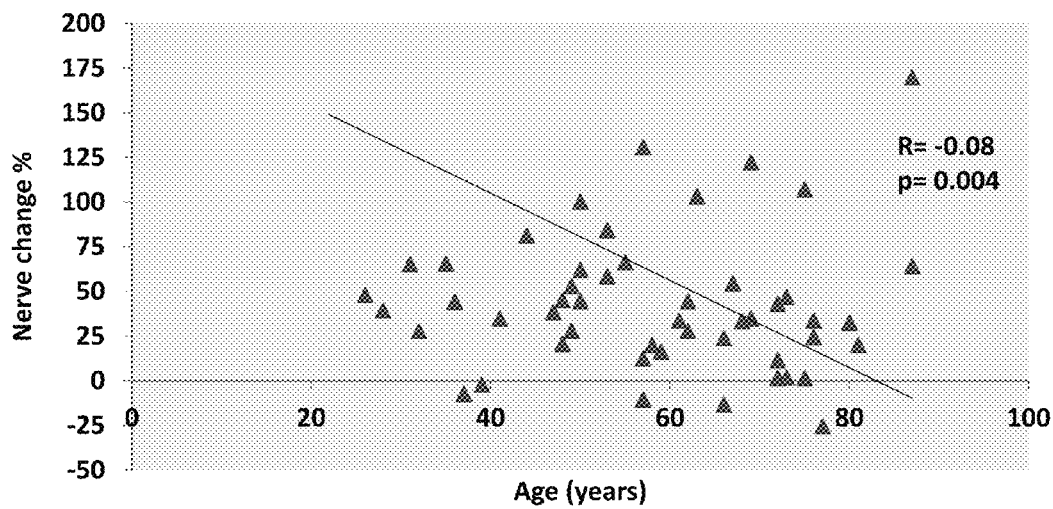
FIG. 60 is a linear regression comparing the percent nerve change achieved in each patient having dry eye syndrome following treatment with autologous serum compared to the age of each subject.
Figure 61:
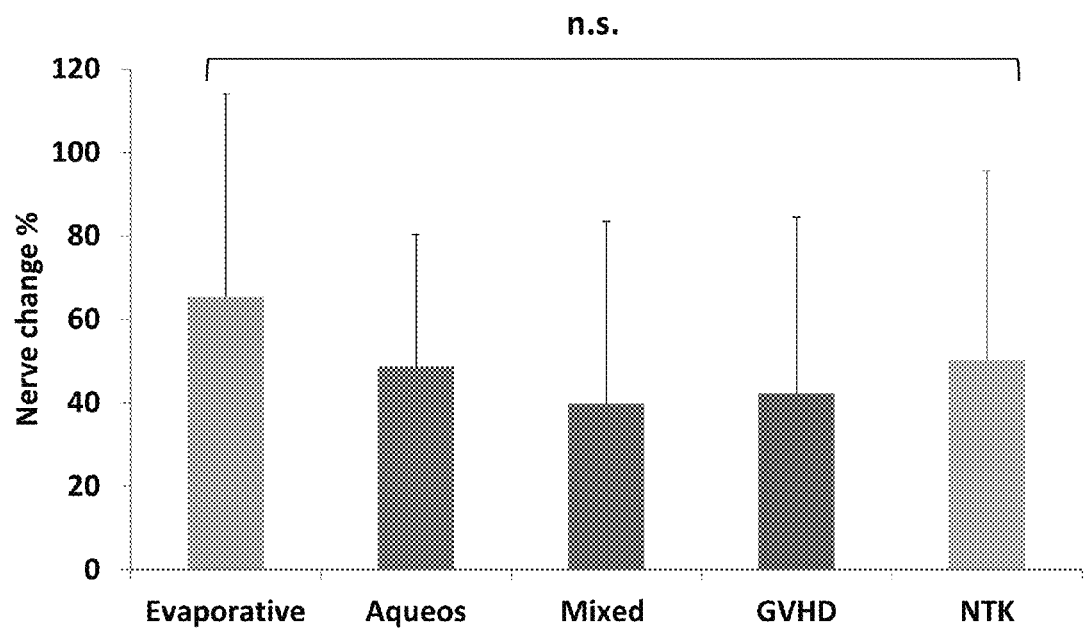
FIG. 61 is a graph of the mean percent nerve change observed following treatment with autologous serum in subjects having evaporative dry eye syndrome (Evaporative), aqueous dry eye syndrome (Aqueous), mixed dry eye syndrome (Mixed), graft-versus-host disease dry eye syndrome (GCHD), and neurotrophic keratopathy dry eye syndrome (NTK).

| | |
|---|---|
| Age (years) | 57.7 ± 2.3 |
| Range (years) | 22-87 |
| Sex (M:F)% | 11(19%):46(81%) |
| Evaporative DES | 8 (14%) |
| Aqueous Deficient DES | 5 (9%) |
| Mixed Mechanism DES | 26 (45%) |
| Neurotrophic keratopathy | 5 (9%) |
| GVHD | 13 (22%) |
| Follow up period (months) | 8.0 ± 0.7 |
| Range (months) | 2.1-21.7 | treatment with autologous serum, there was a significant increase in the nerve plexus in patients having dry eye syndrome (FIG. 51). The total nerve length and total nerve number in the corneas of subjects having dry eye syndrome were increased after the use of autologous serum as compared to the baseline values (prior to autologous serum treatment) in these subjects (FIGS. 52 and 53; ✝, p<0.001). The main nerve trunk length and the main nerve trunk number also increased significantly in the corneas of subjects having dry eye syndrome after treatment with the autologous serum as compared to the baseline values (prior to autologous serum treatment) in these subjects (FIGS. 54 and 55; ✝, p<0.001). The nerve branch length and number also increased significantly in the corneas of subjects having dry eye syndrome after treatment with the autologous serum as compared to the baseline values (prior to autologous serum treatment) in these subjects (FIGS. 56 and 57; ✝, p<0.001; *, p<0.001). The data further show that 90% of the patients having dry eye syndrome demonstrated nerve regrowth following treatment with autologous serum (FIG. 58). Overall, the patients having dry eye syndrome that were treated with autologous serum had a mean increase of 65% of the cornea nerve plexus (FIG. 59). It was also observed that age had a significant negative correlation with the corneal nerve regrowth in patients having dry eye syndrome after treatment with autologous serum (FIG. 60). Nerve regeneration was observed in patients having dry eye syndrome following treatment with autologous serum, regardless of the underlying cause of dry eye syndrome (FIG. 61).

Figure 62:
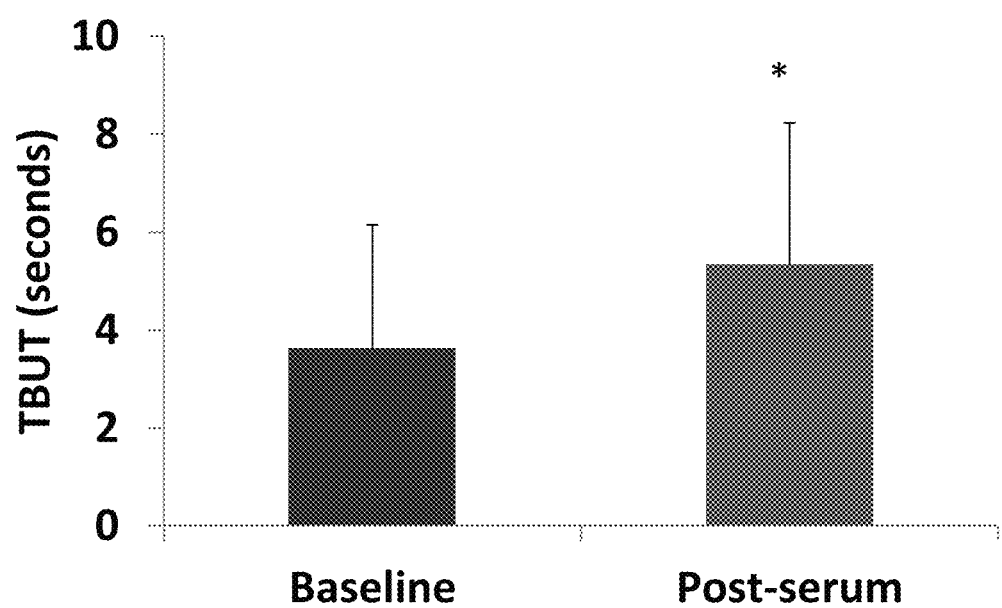
FIG. 62 is a graph of the mean TBUT score of patients having dry eye syndrome at baseline (prior to treatment with autologous serum) and following treatment with autologous serum (Post-serum).
Figure 63:
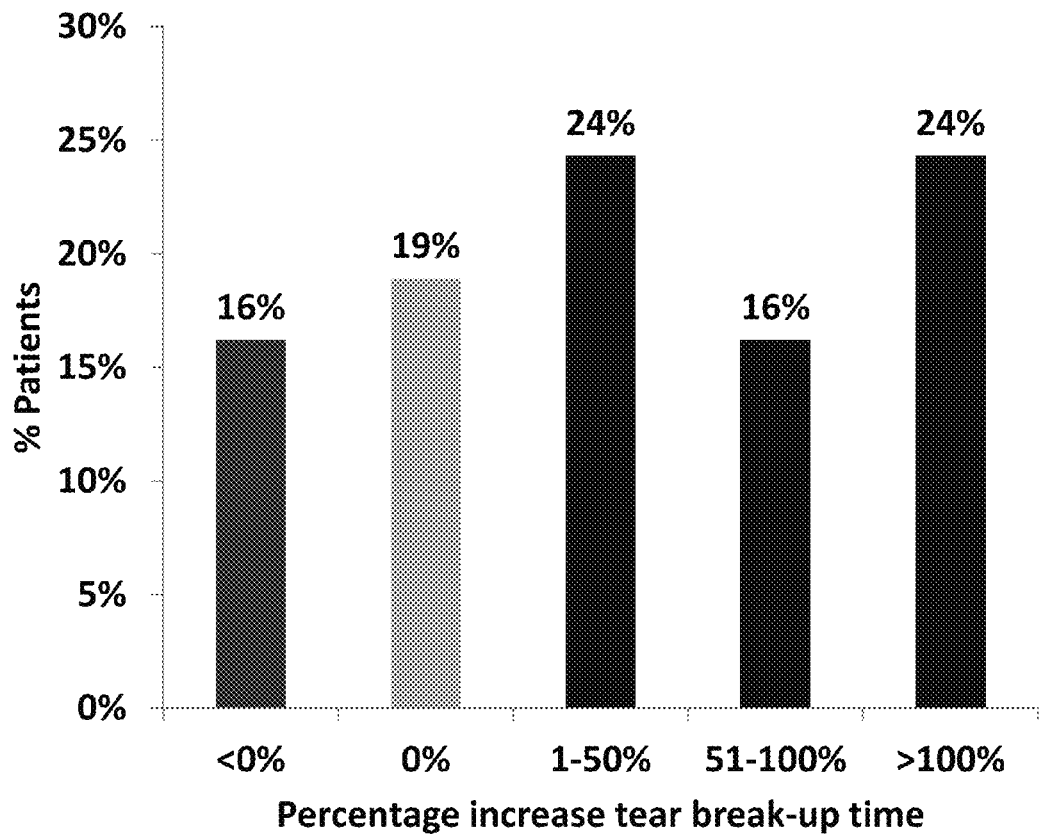
FIG. 63 is a graph of the percentage of patients having dry eye syndrome that received treatment with autologous serum that show a specific percent increase in TBUT.
Figure 64:
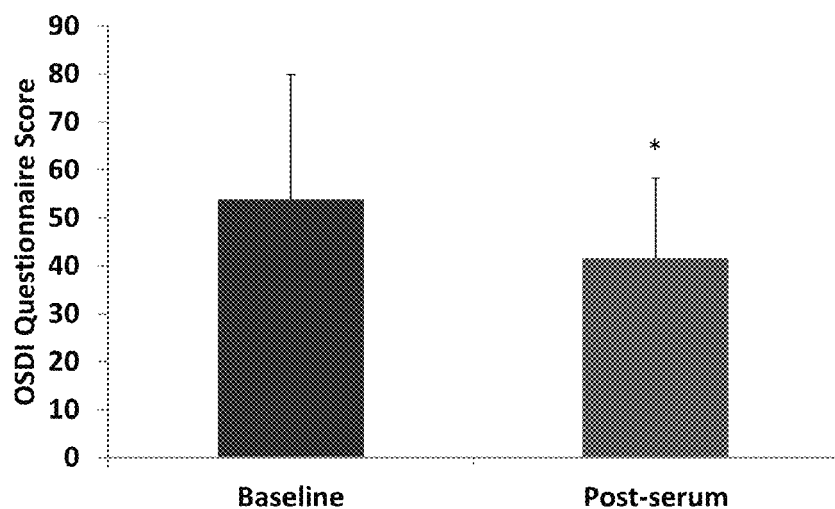
FIG. 64 is a graph of the mean OSDI Questionnaire Score for subjects having dry eye syndrome at baseline (before treatment with autologous serum; Baseline) and after treatment with autologous serum (Post-serum).
Figure 65:
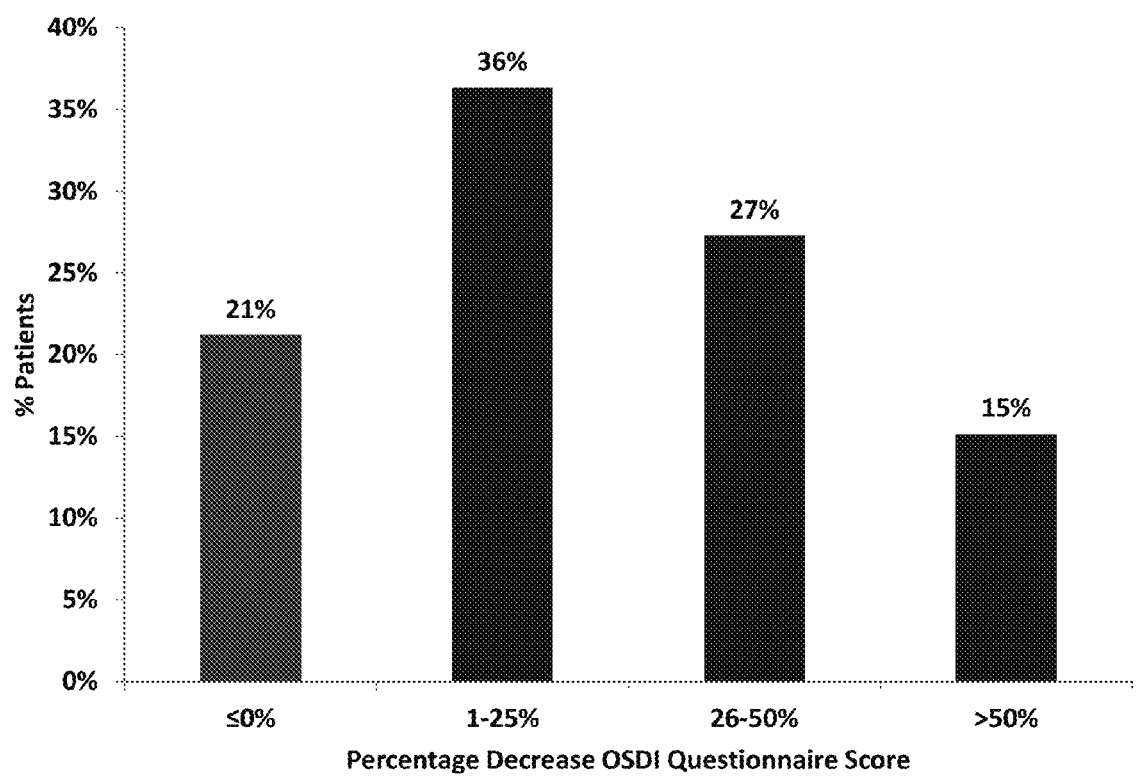
FIG. 65 is a graph of the percentage of patients having dry eye syndrome that were treated with autologous serum that show a specific percentage decrease in OSDI Questionnaire Score (as compared to the OSDI Questionnaire Score of each subject prior to treatment with autologous serum).

The patients having dry eye syndrome that were treated with autologous serum showed a significantly improvement in TBUT as compared to the baseline values (prior to autologous serum treatment) in these subjects (FIG. 62; *, p<0.003). Overall, patients having dry eye syndrome that were treated with autologous serum had a mean increase of 64% in TBUT (FIG. 63). In addition, patients having dry eye syndrome that were treated with autologous serum showed a significant decrease in OSDI Questionnaire Score as compared to the baseline values (prior to autologous serum treatment) in these subjects (FIG. 64). Overall, 79% of the patients having dry eye syndrome that were treated with autologous serum had a decrease in their OSDI score, with a mean overall decrease in OSDI score of 12% (FIG. 65).

In sum, these data show that autologous serum is an effective treatment as coadjuvant therapy in severe dry eye syndrome. In addition, these data demonstrate that changes in the corneal epithelium (as detected using in vivo confocal microscopy) can be detected as used to assess the efficacy of treatment of dry eye syndrome in a subject.

Example 8. Cellular Changes in the Cornea and Conjunctiva in Allergy and Non-Allergic Ocular Inflammatory Diseases These experiments were performed to determine whether changes in the cornea and conjunctiva occur in ocular allergy and non-allergic ocular inflammatory diseases.

In these experiments, the conjunctiva, and central and peripheral cornea of six patients (8 eyes) with ocular allergy (OA), 9 patients (10 eyes) with non-allergic ocular inflammatory diseases (OID), and six control (healthy) subjects (8 eyes) were imaged using scanning laser in vivo confocal microscopy (HRT3/RCM set-up and performed as described herein) with 2 sequences per area. The images were quantified for dendritiform cell (DC) density, superficial epithelial (SE) cell reflectivity, and superficial epithelial cell border reflectivity. Conjunctival blood vessels were assessed for the presence and adhesion of immune cells to vessel wall (cells/100 μm).

The mean age of the subjects having ocular allergy was 25.5±7.7 years, the mean age of the subjects having an ocular inflammatory disease was 54±10.5 years, and the mean age of the control subjects was 30.6±6.4 years. The OID group consisted of patients having infectious keratitis, foreign body infiltration, chlamydial conjunctivitis, graft versus host disease, Steven Johnson's syndrome, and marginal keratitis. All allergy patients in these experiments suffered from seasonal or perennial allergies, with 2 out of the 8 eyes presenting with acute allergic conjunctivitis.

Figure 66:
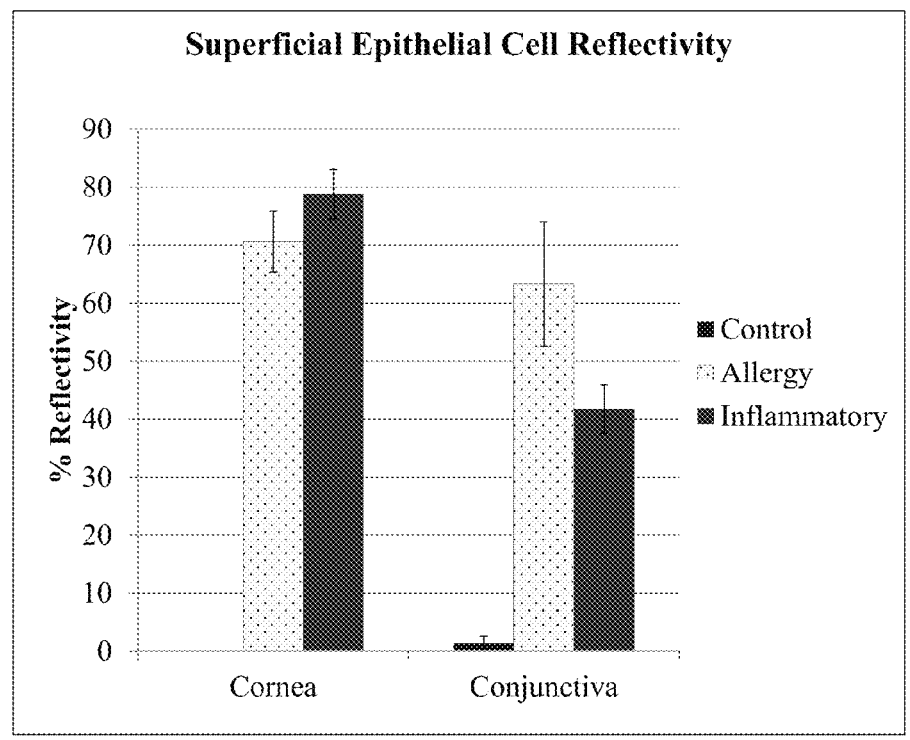
FIG. 66 is a graph showing the mean percentage of superficial epithelial cells that are reflective in the cornea and the conjunctiva of control subjects, subjects having ocular allergy (OA), and subjects having non-allergic ocular inflammatory diseases (OID) (*, p<0.0001).
Figure 67:
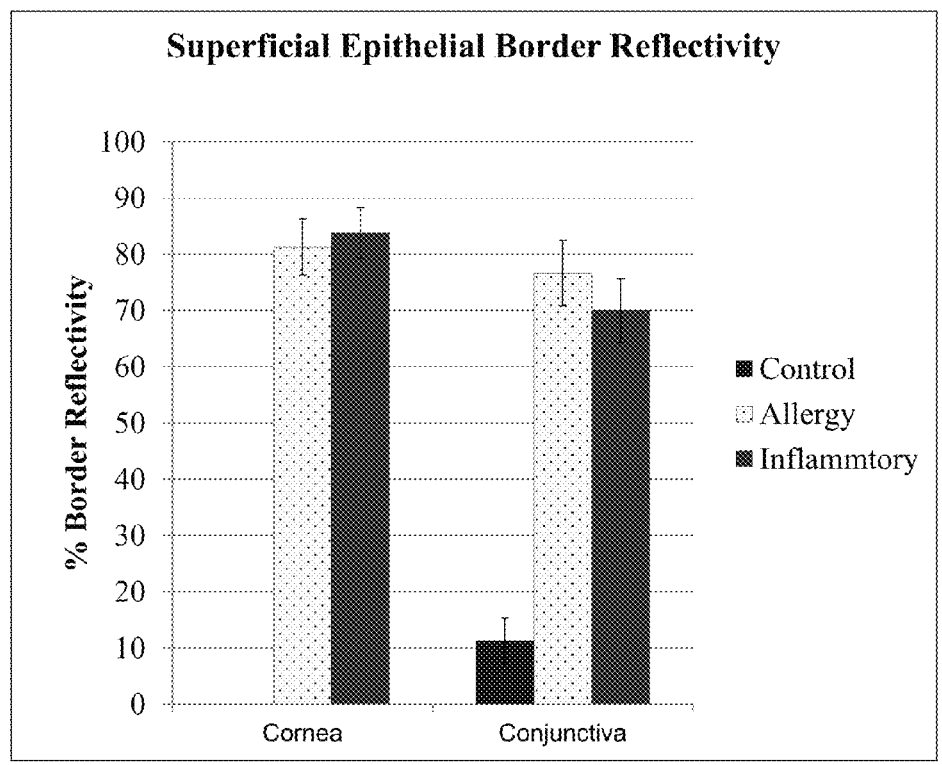
FIG. 67 is a graph showing the mean percentage of superficial epithelial cells that show border reflectivity in the cornea and conjunctiva of control subjects, subjects having OA, and subjects having OID (*, p<0.0001).
Figure 68:
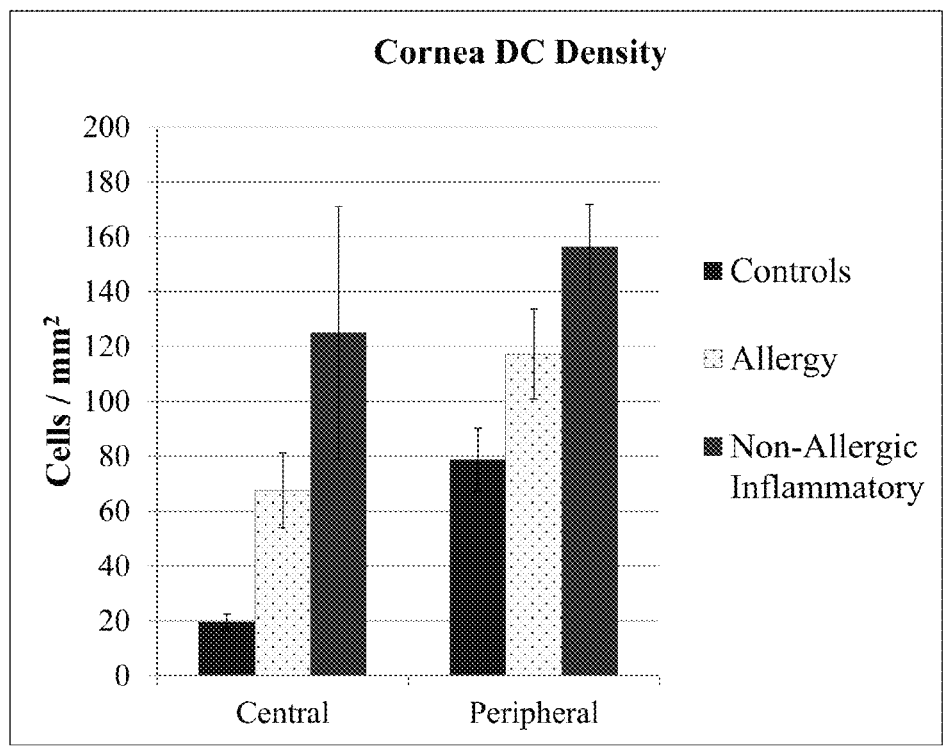
FIG. 68 is a graph showing the mean dendritic cell density in the cornea and conjunctiva of control subjects, subjects having OA, and subjects having OID (*, p>0.05).
Figure 69:
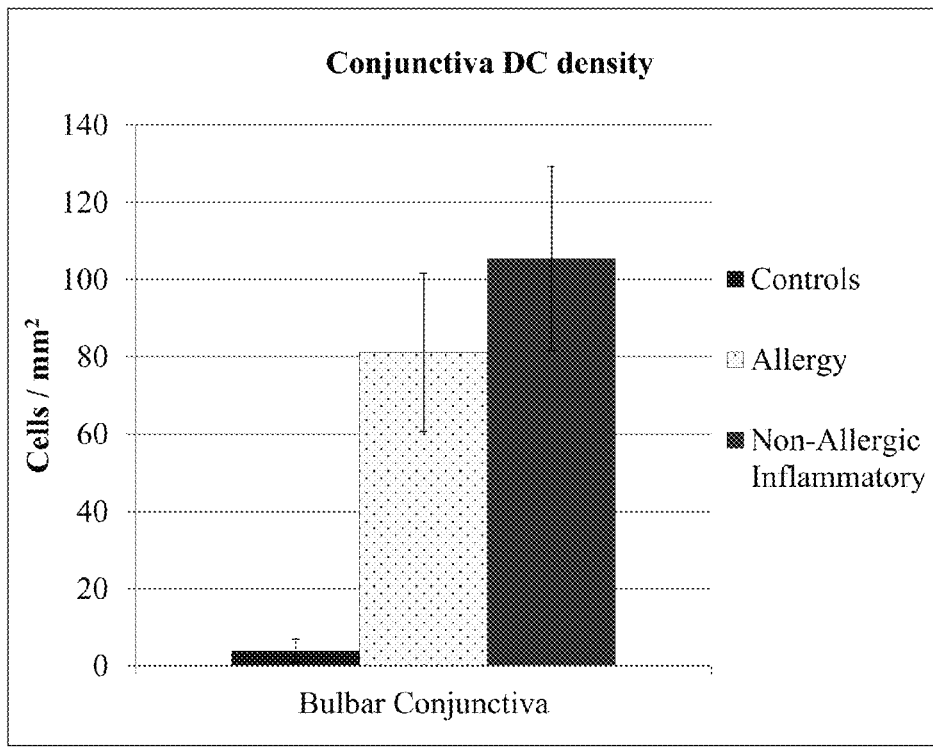
FIG. 69 is a graph showing the mean dendritic cell density in the conjunctiva of control subjects, subjects having OA, and subjects having OID (*, p<0.001).

Table 6 shows the cornea superficial epithelial cell reflectivity and corneal dendriform cell density in ocular allergy, non-allergic ocular inflammatory, and control groups. As can be seen in the table below, patients with OA and OID demonstrated increased superficial epithelial cell hyperreflectivity in the cornea (71%±6.9 and 78%±4.3, respectively; mean±SEM), as compared to controls (0% and 3.5%±1,3; p<0.0001). The superficial epithelial cell border reflectivity in the area of tight junctions was increased in the cornea for OA and OID (83%±5.0 and 84%±4.5; mean±SEM) and conjunctiva (77%±5.8 and 70%±5.7), as compared to controls (0% cornea; 11%±4.0 conjunctiva; p<0.0001). Central corneal dendritic cell density was increased for OA subjects (3.5×; 67.5±13.7; fold increase; mean±SEM) and for OID subjects (6.4×; 125±46), as compared to control subjects (19.5±3; p=0.11). While central corneal dendritic cell density was lower in subjects with acute OA (46.8±21.9 cells/mm$^2$; mean±SEM) versus subjects with acute OID (256.25±175), subjects with chronic OA (75.0±16.7) had higher dendritic cell density compared to subjects with chronic IOD and normal subjects (p=0.04). In the peripheral cornea, a 35% and 90% increase in dendritic cell density was observed in subjects with acute OA and chronic OA, respectively, as compared to controls (p>0.05). Data showing the mean percentage of reflective superficial epithelial cells in the cornea and conjunctiva for controls subjects, subjects having OA, and subjects having OID are shown in FIG. 66. Data showing the mean percentage of superficial epithelial cells in the cornea and conjunctiva showing border reflectivity for control subjects, subjects having OA, and subjects having OID are shown in FIG. 67. Data showing the mean dendritic cell density in the corneas and conjunctiva of control subjects, subjects having OA, and subjects having OID are shown in FIG. 68. Data showing the mean dendritic cell density in the corneas and conjunctiva of controls subjects, subjects having OA, and subjects having OID are shown in FIG. 69.

Figure 70:
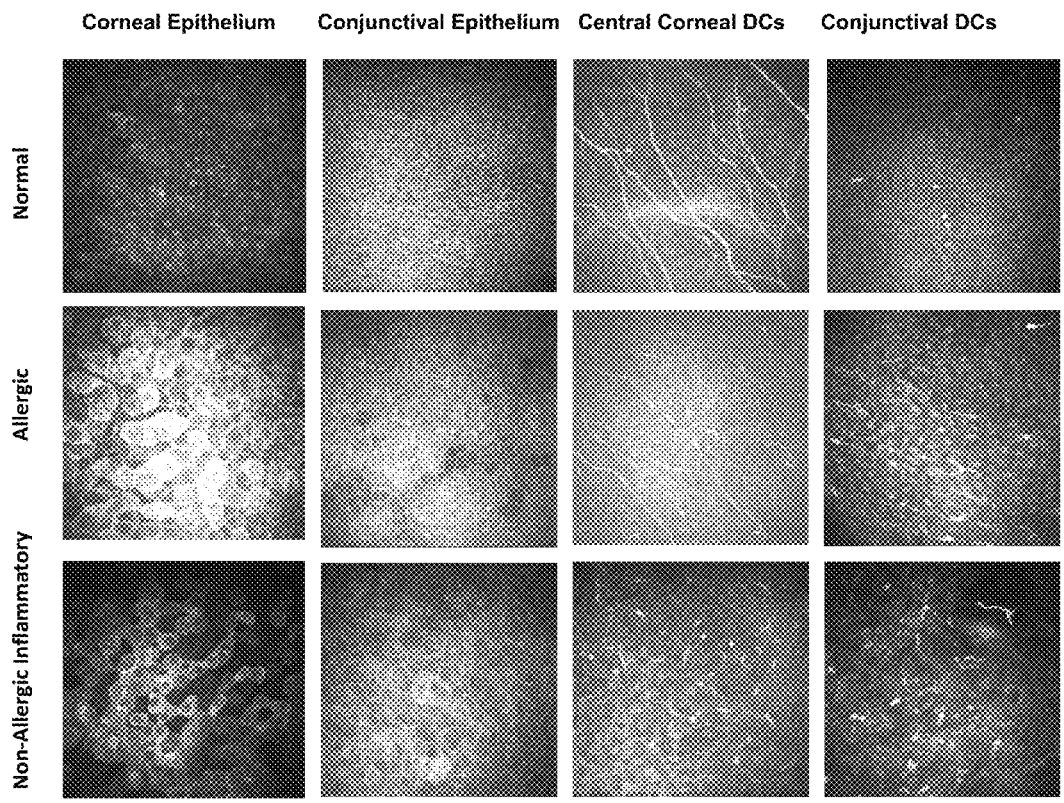
FIG. 70 is a set of twelve exemplary in vivo confocal microscopy images showing the corneal epithelium, conjunctival epithelium, central corneal dendritic cells, and conjunctival dendritical cells in control subjects (Normal), subjects having OA (Allergic), and subjects having OID (Non-Allergic Inflammatory).

Table 7 shows the cojunctival superficial epithelial cell reflectivity and conjunctival dendriform cell density in ocular allergy, non-allergic ocular inflammatory, and control groups. Conjunctival dendritic cell density was significantly increased in both subjects having OA (131.2±100; mean±SEM) and subjects having OID (234.4±206), as compared to controls (17.5±16.2; p=0.001). Exemplary in vivo confocal microscopic images of the cornea and the conjunctiva for subjects having OA or OIA are shown in FIG. 70.

TABLE 6

Cornea Superficial Epithelial Cell Reflectivity and Corneal Dendritiform Cell Density

| CORNEA | SE Reflectivity | SE Border Reflectivity | Central DC | Peripheral DC |
|---|---|---|---|---|
| Normal Controls | 0 | 0 | 19.5 ± 3.0 | 78.7 ± 11.5 |
| Ocular Allergy | 70.6 ± 6.9* | 83.1 ± 5.0* | 67.5 ± 13.7 | 117.2 ± 16.4 |
| Ocular Inflammatory Disease | 78.8 ± 4.3* | 83.8 ± 4.5* | 125.0 ± 46.0 | 156.2 ± 15.6 |

*p < 0.0001 (ANOVA between OA, IOD and controls; Mean ± SEM)

TABLE 7

Conjunctival Superficial Epithelial Cell Reflectivity and Conjunctival Dendritiform Cell Density

| CORNEA | SE Reflectivity | SE Border Reflectivity | Central DC | Peripheral DC |
|---|---|---|---|---|
| Normal Controls | 0 | 0 | 19.5 ± 3.0 | 78.7 ± 11.5 |
| Ocular Allergy | 70.6 ± 6.9* | 83.1 ± 5.0* | 67.5 ± 13.7 | 117.2 ± 16.4 |
| Ocular Inflammatory Disease | 78.8 ± 4.3* | 83.8 ± 4.5* | 125.0 ± 46.0 | 156.2 ± 15.6 |

*ANOVA between OA, OID eyes and controls (*p = 0.0001; **p = 0.001; mean ± SEM)

Figure 71:
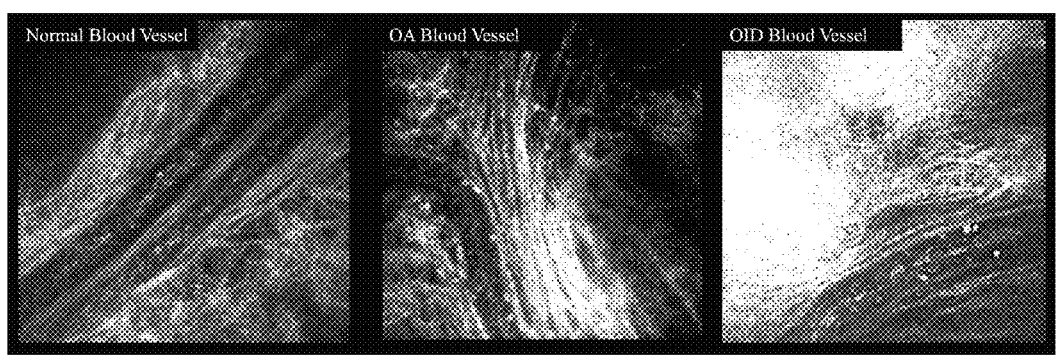
FIG. 71 is a set of three exemplary in vivo confocal microscopic images showing the conjunctival blood vessels in a control subject, a subject having OA, and a subject having an OID.

Conjunctival vessels demonstrated increased immune cell adhesion in subjects having OA (5.5±0.7 cells/100 μm vessel length; mean±SEM) and in subjects having OID (5.7±1.7), as compared to control subjects (0.13±0.35; p<0.0001) (FIG. 71).

In sum, the data show that profound immune and inflammatory changes occur in ocular allergic and non-allergic ocular inflammatory diseases, and superficial epithelial cell changes in the corneal and conjunctival epithelium of patients with both OA and OID. These data indicate that in vivo confocal microscopy can be used to stratify patients and assess a subject's responsiveness to treatment.

Example 9. Corneal Analysis of Subjects Having Limbal Stem Cell Insufficiency

An additional set of experiments were performed to determine if the corneal changes described herein also occur in patients having limbal stem cell insufficiency (LSCI). LSCI is a condition in which inflammation from injury or disease causes significant ocular morbidity.

In these experiments, the clinical charts and images of three patients diagnosed with LSCI were retrospectively reviewed. Each subject underwent a complete exam and in vivo confocal microscopy (using HRT3/RCM, as described herein) of the central cornea and the superior limbus at each visit. The patients were followed monthly until resolution. The patients were treated with topical steroid drops based on in vivo confocal microscopy findings that indicate the presence of inflammation. Three representative images from the central cornea and the superior limbus were selected for the analysis of each parameter, and compared with images obtained from previously tested normal (healthy) subjects. The images were quantified for dendritiform immune cell density (DC) and total counts of nerves and branches with respective density with ImageJ/Neuron J software.

The first patient (Patient 1) was a 13 year old female who had been wearing contact lenses for 2 years. Patient 1 had a visual acuity of 20/25 OD and 20/40 OS at presentation. After treatment with rimexolone 1% QID initially, and then taper for 5 months, Patient 1's visual acuity returned to 20/20 OU.

The second patient (Patient 2) was a 31 year old female who had been wearing contact lenses for 15 years. Patient 2 had a visual acuity of 20/20 OD and 20/60 OS at presentation. After treatment with loteprednol 0.5% QID initially, and then taper for 11 months, Patient 2's visual acuity returned to 20/20 OU.

The third patient (Patient 3) was a 39 year old female who had been wearing contact lenses for 15 years. Patient 3 had a visual acuity of 20/30 OD and 20/20 OS at presentation. After treatment with loteprednol 0.5% QID initially, and then taper for 4 months, Patient 3's visual acuity returned to 20/20 OU.

In the examined LSCI subjects, the average length of contact lens wear was 10.7 years. The subjects were followed for 4-11 months (average of 6.7 months). The average visual acuity for the subjects was 20/30 (range of 20/20 to 20/60) at presentation.

Figure 72:
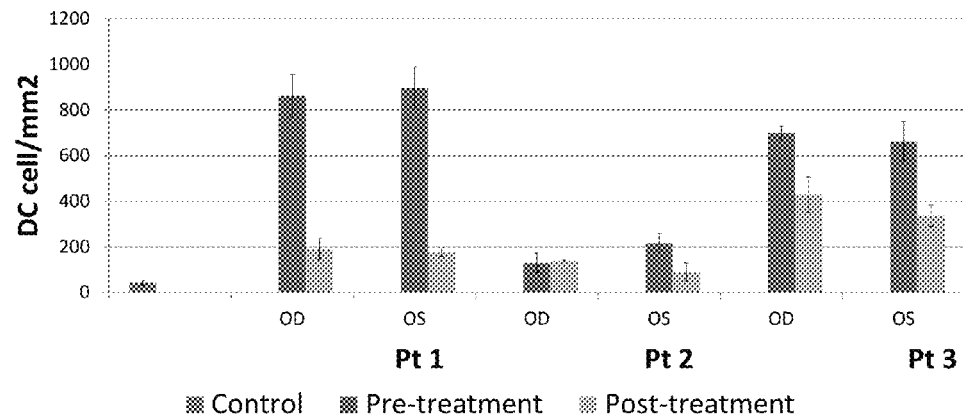
FIG. 72 is graph of the mean dendritic cell density in the central cornea of each eye in three limbal stem cell insufficiency patients before treatment and after treatment, and in the central corneas of control patients.
Figure 73:
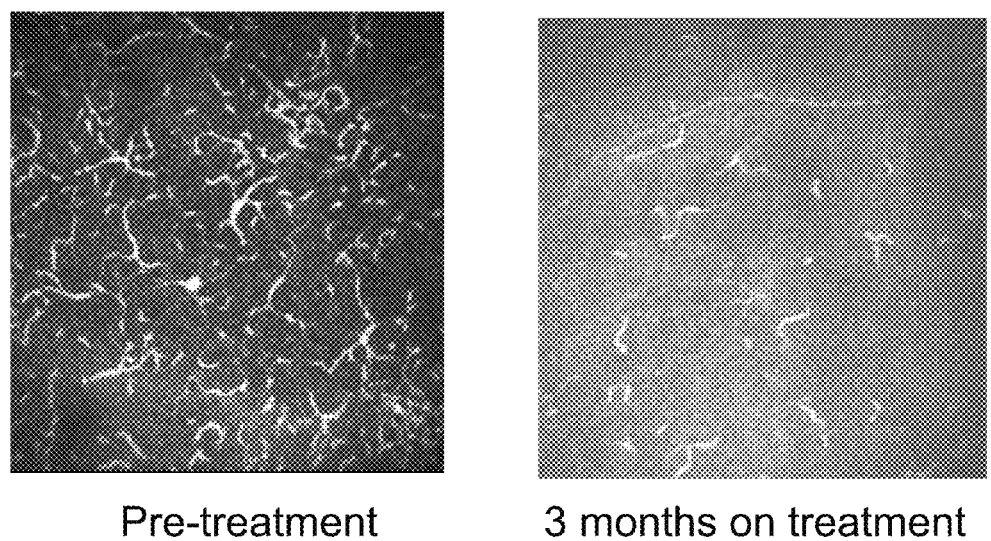
FIG. 73 is an in vivo confocal microscopic image showing the central cornea of a subject having limbal stem cell insufficiency before treatment (pre-treatment) (left) and an in vivo confocal microscopic image showing the central cornea of the same subject after 3-months of treatment (3 months on treatment) (right).

In vivo confocal microscopy demonstrated that the LSCI subjects had a mean central cornea dendritic cell density of 577.4±323.8 cells/mm$^2$ at presentation, which was significantly higher than normal subjects (42.5±40.5, p<0.05) (FIG. 72). In view of the increased presence of dendritic cells in the central cornea (increased dendritic cell density in the cornea as compared to normal healthy controls), these subjects were identified as having corneal inflammation and were administered loteprednol etabonate (0.5% taper; 2 patients; 4 eyes) or rimexolone (1% taper; 1 patient; 2 eyes) for three months. Following three months of treatment, the average dendritic cell density in the cornea of the LSCI subjects significantly decreased to 234.6±233.7 cells/mm$^2$ compared to the dendritic cell density in these subjects on presentation (p=0.001) (FIG. 73). The average density of dendritic cells in the superior limbus after treatment was 238.2±158.4 cells/mm$^2$.

Figure 74:
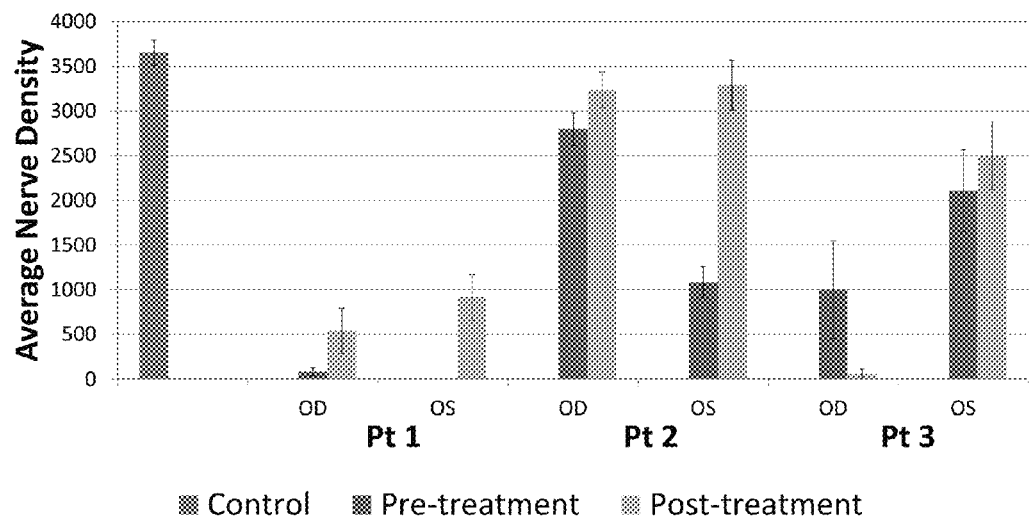
FIG. 74 is a graph of the mean nerve density in the central cornea of each eye in three limbal stem cell insufficiency patients before treatment and after treatment, and in the corneas of control patients.
Figure 75:
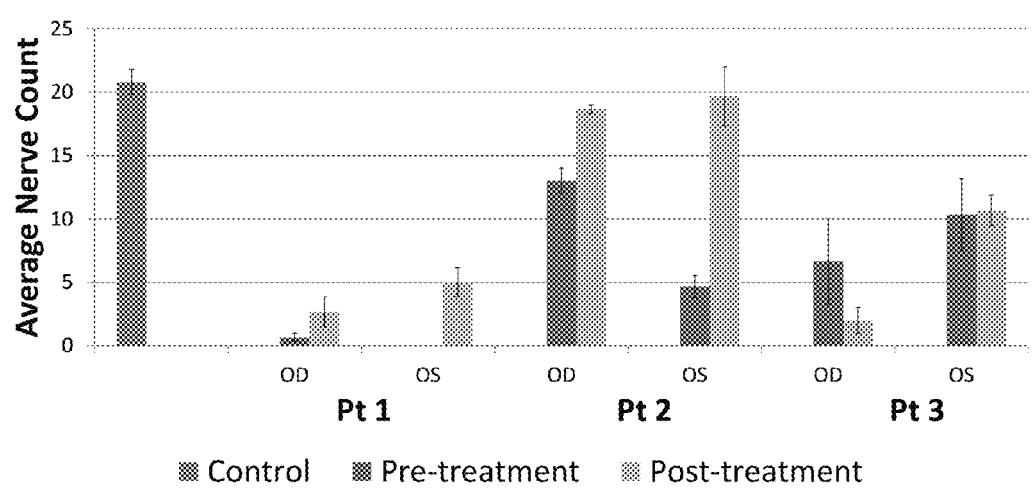
FIG. 75 is a graph of the of the mean nerve count in the central cornea of each eye in three limbal stem cell insufficiency patients before treatment and after treatment, and in the corneas of control patients.
Figure 76:
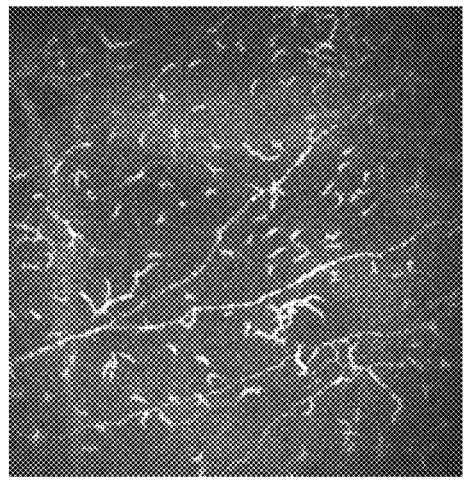
FIG. 76 is an in vivo confocal microscopic image of the cornea of a subject having limbal stem cell insufficiency before treatment (left) and an image of the cornea of the same subject after treatment (right).
Figure 76:
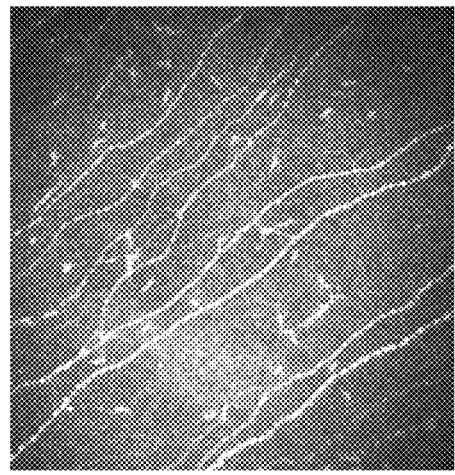

Subjects having LSCI were also determined to have a decrease in corneal nerve count and density at presentation as compared to healthy controls (FIGS. 74 and 75). After treatment, there was a significant increase in the total number of nerves and branches in the cornea, as well as a significant increase in nerve branch density as compared to the corresponding values determined at presentation (FIG. 74). Representative images of a LSCI subject's cornea before and after treatment are shown in FIG. 76.

Figure 77:
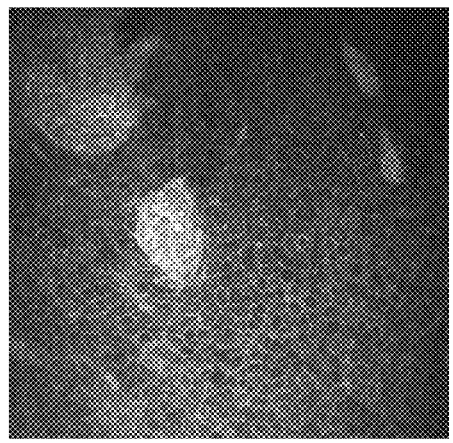
FIG. 77 is a set of two in vivo confocal microscopic images showing the conjunctivalization in the cornea of a subject having limbal stem cell insufficiency at presentation (left) and after 4-months of treatment (right).
Figure 77:
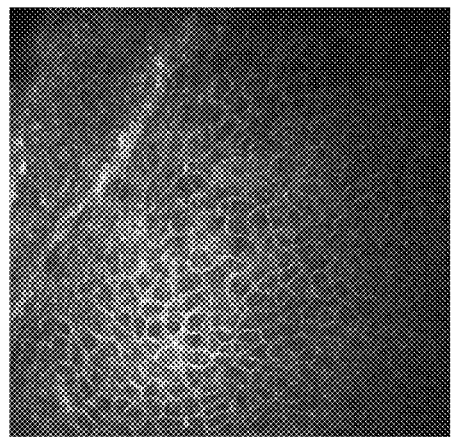

The corneal epithelium in each patient qualitatively showed a higher rate of conjunctivalization by in vivo confocal microscopy, which subsequently decreased with treatment (FIG. 77). The in vivo confocal microscopic changes observed corresponded to an improvement of mean visual acuity of 20/20 and a decrease in corneal staining.

These data indicate that LSCI can be diagnosed or the severity of LSCI in a subject can be diagnosed using the in vivo confocal microscopy methods described herein. In addition, the in vivo confocal microscopy methods described herein can be used to determine the efficacy of treatment of LSCI in a subject.

Example 10. Dendritic Cell Density in Corneas of Healthy Subjects

These experiments were performed to determine the control values for dendritic cell density in the central and peripheral quandrants of corneas of healthy control subjects using a laser-scanning in vivo confocal microscope (Heidelberg Retina Tomograph (HRT3) used in conjunction with the Rostock Cornea Module (RCM), and equipped with 670 nm diode laser).

Sixty-five healthy (control) subjects were enrolled in this study. Slit-lamp examination was performed to confirm lack of ocular findings in the enrolled subjects. Laser in vivo confocal microscopy (using HRT3/RCM as described herein) was used to gather images of the center and four quadrants of the cornea. The demographics of the subjects enrolled in this study are shown in Table 8. Two scan sequences were recorded for each area.

TABLE 8

Demographics of Normal (Healthy) Subjects in Study

| Normal Subjects | Age (years) mean ± SD | Sex (M:F) |
| --- | --- | --- |
| 65 | 30.9 ± 10.4 | 31:34 |

Figure 78:
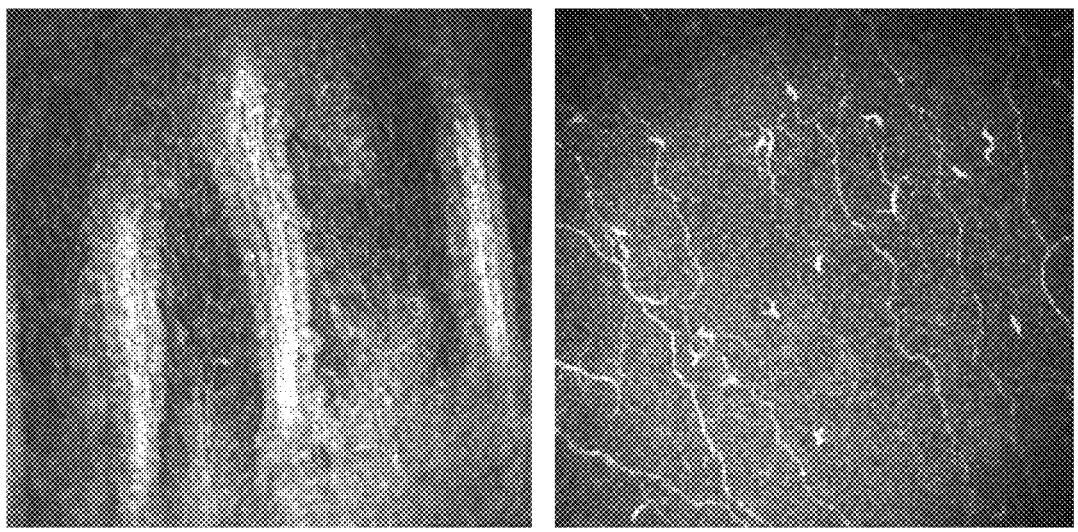
FIG. 78 is an in vivo confocal microscopic image of the limbal area of a healthy (control) subject (left) and an in vivo confocal microscopic image of the peripheral cornea of a healthy subject (right).
Figure 79:
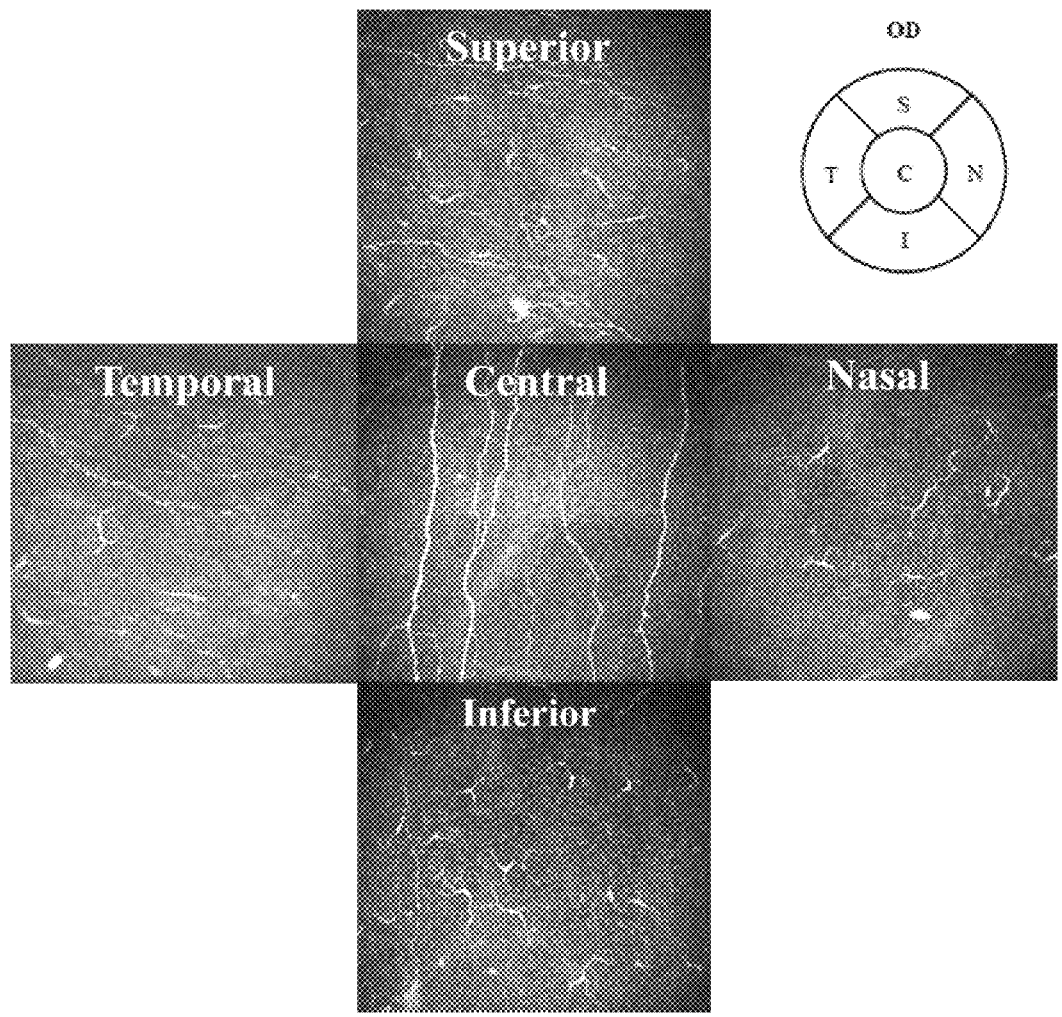
FIG. 79 is set of exemplary in vivo confocal microscopic images showing the central cornea and the peripheral quadrants of the cornea (superior, temporal, inferior, and nasal quandrants) in a healthy (control) subject.
Figure 80:
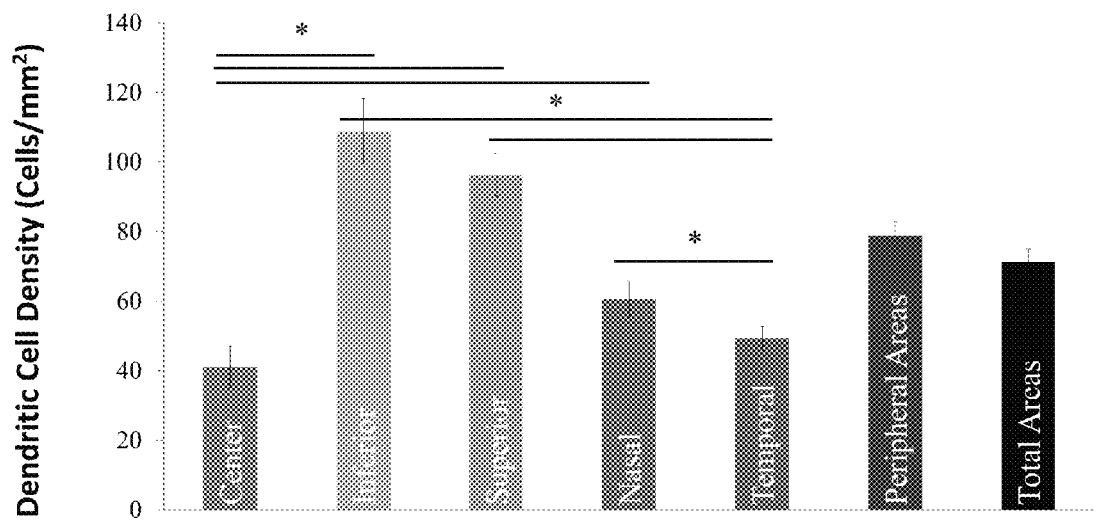
FIG. 80 is a graph showing the mean dendritic cell density in the center cornea, inferior quadrant of the cornea, the superior quadrant of the cornea, the nasal quadrant of the cornea, the temporal quadrant of the cornea, the peripheral areas of the cornea, and the total areas of the cornea of healthy (control) subjects. *, ANOVA with Bonferroni correction (p<0.0001) for peripheral areas versus central cornea.
Figure 81:
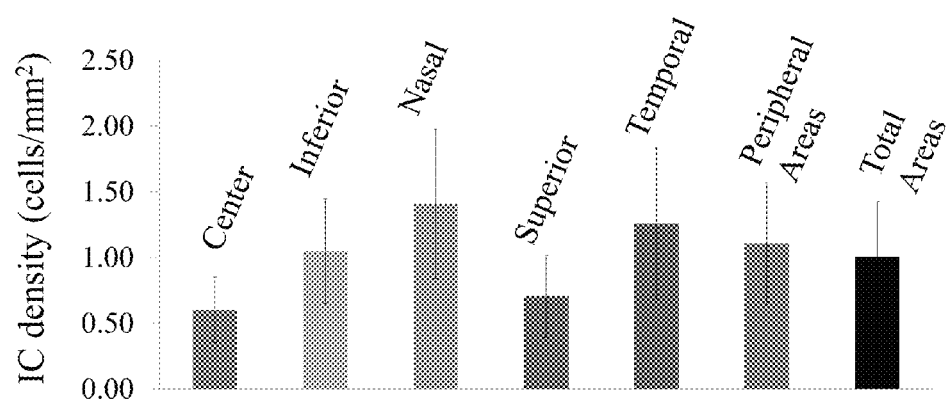
FIG. 81 is a graph showing the mean immune cell density by area in the center cornea, inferior quadrant of the cornea, the superior quadrant of the cornea, the nasal quadrant of the cornea, the temporal quadrant of the cornea, the peripheral areas of the cornea, and the total areas of the cornea of healthy (control) subjects. No statistical difference was detected when comparing all areas.

Exemplary in vivo confocal microscopic images showing the visualization of the limbus quadrant of the cornea and the peripheral cornea are shown in FIG. 78. Additional exemplary in vivo confocal microscopic images of each quadrant of the cornea examined are shown in FIG. 79. A graph showing the density of dendritic cells in each area of the cornea in control healthy subjects is shown in FIG. 80. A graph of the immune cell density in each area of the cornea in control healthy subjects is shown in FIG. 81. These data reveal the presence of dendritic cells in the central and peripheral cornea in all healthy subjects. The dendritic cell density for the central cornea in healthy subjects was 41.01±5.96 cells/mm$^2$ (mean±SEM). The densities of dendritic cells in healthy subjects in the superior, inferior, and nasal quandrants were higher than the density of dendritic cells found in the central cornea (mean±SEM; p<0.0001). The superior (96.31±6.10 cells/mm$^2$) and inferior (108.82±9.33) quadrants demonstrate the highest dendritic cell density as compared to the nasal (60.63±5.15 cells/mm$^2$) and temporal (49.26±3.49 cells/mm$^2$) quandrants in the cornea of healthy subjects. There was a significant statistical difference between the dendritic cell density in the temporal quadrant and the other peripheral areas in the healthy subjects (p<0.0001). The immune cell density was extremely low overall in the corneas of healthy subjects, with the highest density of immune cells present in the nasal quadrant (1.2±3.8 cells/mm$^2$) and lowest density in the central cornea (0.7±2.0 cells/mm$^2$), although no statistical difference was detected when comparing the five examined areas of the cornea. Excellent interobserver variability was observed between observers for all the areas combined.

These values and ranges determined in healthy subjects can be non-limiting references values in any of the methods described herein.

Example 11. Additional Study of Dendritic Cells in Corneas of Healthy Subjects

An additional study was performed in 85 normal (healthy subjects) (85 total eyes) to determine the control values for dendritic cells in the central and peripheral quandrants (inferior, nasal, superior, and temporal peripheral quadrants) of corneas of healthy control subjects using a laser-scanning in vivo confocal microscope (Heidelberg Retina Tomograph (HRT3) used in conjunction with the Rostock Cornea Module (RCM), and equipped with 670 nm diode laser) as described herein. Slit-lamp examination was performed to confirm lack of ocular disease in each subject. The images were assessed for dendritic cell morphology and density by two masked observers. Morphology was assessed by number of dendrites per cell, area of dendritic cells, and dendritic cell field. Statistical analysis was performed with ANOVA/Bonferroni to compare the differences between areas and the intraclass coefficient was used to assess interobserver reproducibility.

The mean age of healthy subjects in this study was 31.4 years (range of 20 to 69). The images revealed the presence of central (35.6±4.3 cells/mm$^2$) and peripheral (74.1±4.5 cells/mm$^2$) corneal dendritic cells in all areas of all subjects. The number of dendrites, area of dendritic cells, and dendritic cell field in the central cornea were 2.4±0.04 dendrites/cell, 71.6±4.3 μm$^2$, and 304.2±19.2 μm$^2$, respectively. The number of dendrites (3.2±0.07 dendrites/cell, inferior; 2.9±0.03 dendrites/cell, nasal; 3.0±0.03 dendrites/cell, superior; and 2.9±0.03 dendrites/cell, temporal), area of dendritic cells (134.6±3.5 μm$^2$, inferior; 115.3±3.4 μm$^2$, nasal; 117.0±3.5 μm$^2$, superior; and 121.2±3.9 μm$^2$, temporal), and dendritic cell field area (684.4±19.1 μm$^2$, inferior; 586.2±19.7 μm$^2$, nasal; 587.7±17.4 μm$^2$, superior; and 601±18.6 μm$^2$, temporal), were found to be significantly larger in all 4 peripheral quadrants (p<0.001). Good interobserver reproducibility coefficient was found for dendritic cell area (0.83; 0.77-0.91 95% CI), number of dendrites per cell (0.97; 0.95-0.99), and dendritic cell coverage area (0.94; 0.85-0.98). These values and ranges determined in healthy subjects can be non-limiting reference values or ranges in any of the methods described herein.

Example 12. Study of Nerves in Corneas of Healthy Subjects

These experiments were performed to determine the subbasal corneal nerve density in the central cornea and four peripheral quadrants of the cornea of healthy (control) subjects using a laser-scanning in vivo confocal microscope (Heidelberg Retina Tomograph (HRT3) used in conjunction with the Rostock Cornea Module (RCM), and equipped with 670 nm diode laser) as described herein. A total of 37 healthy (control) subjects were used in these studies. Slit-lamp examination was performed to confirm lack of ocular disease in each subject. Three representative images were chosen for each corneal area and quantified using NeuronJ, a plugin for ImageJ software (NIH). Two masked observers measured the number and density of total nerves, main trunks, and branches for each image. Statistical analysis was performed with ANOVA with Bonferroni correction to compare the differences between the 5 cornea areas. A linear regression model was applied to assess the changes for gender and age.

The average age of the healthy (normal) subjects participating in these studies was 30 years, ranging from 19 to 69 years. The central cornea in the healthy (control) subjects had a significantly higher number and density of total nerves (16.2 nerves/frame, [14.8-17.6] 95% CI; and 20067.7 μm/mm$^2$, [18776.6-21358.8] 95% CI, respectively), main trunks (3.3, [2.9-3.6] 95% CI), and branches (12.8, [11.4-14.2] 95% CI) in comparison to all peripheral areas (p<0.001). All peripheral areas in the healthy subjects demonstrated similar distribution of the subbasal nerve plexus for all parameters (p>0.05), including the number and density of total nerves in the superior (9.2, [7.8-10.6] 95% CI; and 11638.1, [9834.7-13441.5] 95% CI, respectively), inferior (9.2, [7.5-11.0] 95% CI, and 11169.3, [9080.2-13258.4] 95% CI, respectively), temporal (8.9, [7.5-10.3] 95% CI, and 9535.3, [8452.7-10617.9] 95% CI, respectively), and nasal (7.8, [6.2-9.4] 95% CI, and 9621.0, [7832.3-11409.8] 95% CI, respectively) quadrants. An inverse correlation to age (p=0.017), but not for gender (p=0.781) was shown for all nerve parameters. These values and ranges determined in healthy subjects can be non-limiting references values or ranges in any of the methods described herein.

Example 13. Additional Study of Nerves in Corneas of Healthy Subjects

Further experiments were performed to determine the subbasal corneal nerve density in the central cornea and four peripheral quadrants of the cornea of healthy (control) subjects using a laser-scanning in vivo confocal microscope (Heidelberg Retina Tomograph (HRT3) used in conjunction with the Rostock Cornea Module (RCM), and equipped with 670 nm diode laser) as described herein. A total of 85 healthy (control) subjects were used in these studies and a total of 85 eyes examined. Subjects were excluded from the study if they had previous ocular disease, previous ocular surgery, contact lens use, or systemic disease (e.g., diabetes). Three representative images were chosen for each corneal area and quantified using NeuronJ, a plugin for ImageJ software (NIH). Subbasal nerve count, nerve length, and nerve density, and main nerve trunks, nerve branches, and total nerve fibers were determined for each image. Statistical analysis was performed with ANOVA with Bonferroni correction to compare the differences between the 5 cornea areas. A Pearson R coefficient and multivariate linear regression analysis were used to address the correlation with age and gender. The differences were considered statistically different for p-value less than 0.05. Table 9 below shows the demographics for the subjects that participated in this study.

TABLE 9

Demographics of healthy (control) subjects in study

|  | Total | MEEI | UI |
|---|---|---|---|
| No. of patients (n) | 85 | 37 | 48 |
| Age (mean ± SD, yrs) | 31.4 ± 10.5 | 30.0 ± 11.5 | 32.6 ± 9.8 |
| Gender (male/female) | 35/50 | 17/20 | 18/30 |

Mean ± SEM

Table 10 below lists the mean±SEM total nerve number, main nerve trunk number, nerve branch numbers, total nerve length, main trunk nerve length, and branch nerve length for the central cornea and the four peripheral quadrants of the cornea (inferior quadrant, inferior quadrant, nasal quadrant, superior quadrant, and temporal quadrant).

Figure 82:
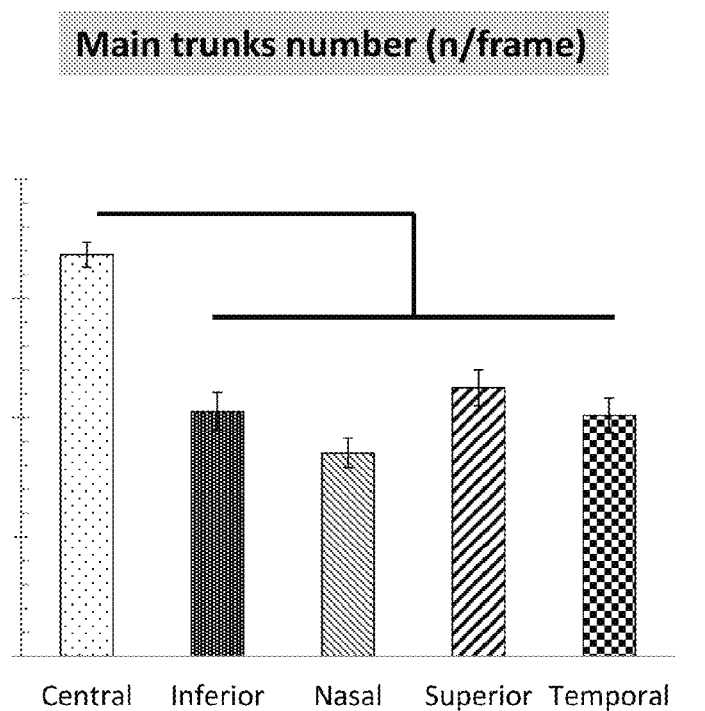
FIG. 82 is a graph of the mean main nerve trunk number (number/frame) in the central cornea and in each of the four peripheral cornea quadrants (inferior, nasal, superior, and temporal quadrants) in healthy (control) subjects. The data shown are the mean±SEM.
Figure 83:
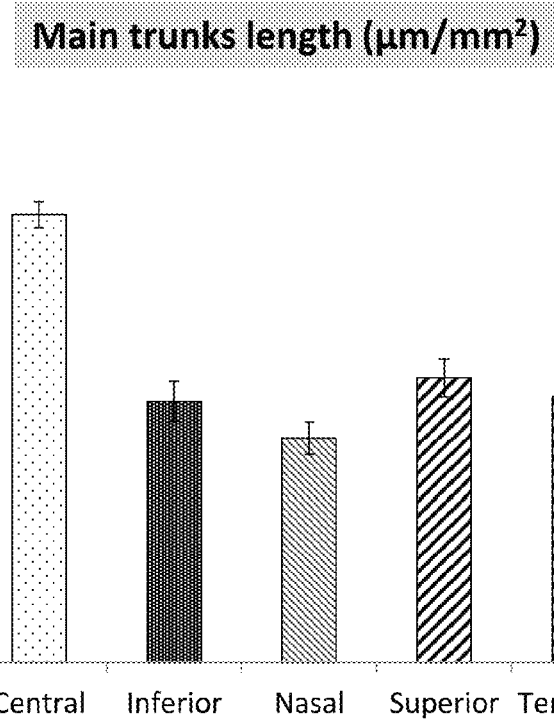
FIG. 83 is a graph of the mean main nerve trunk length ($\mu m/mm^2$) in the central cornea and in each of the four peripheral cornea quadrants (inferior, nasal, superior, and temporal quadrants) in healthy (control) subjects. The data shown are the mean±SEM.
Figure 84:
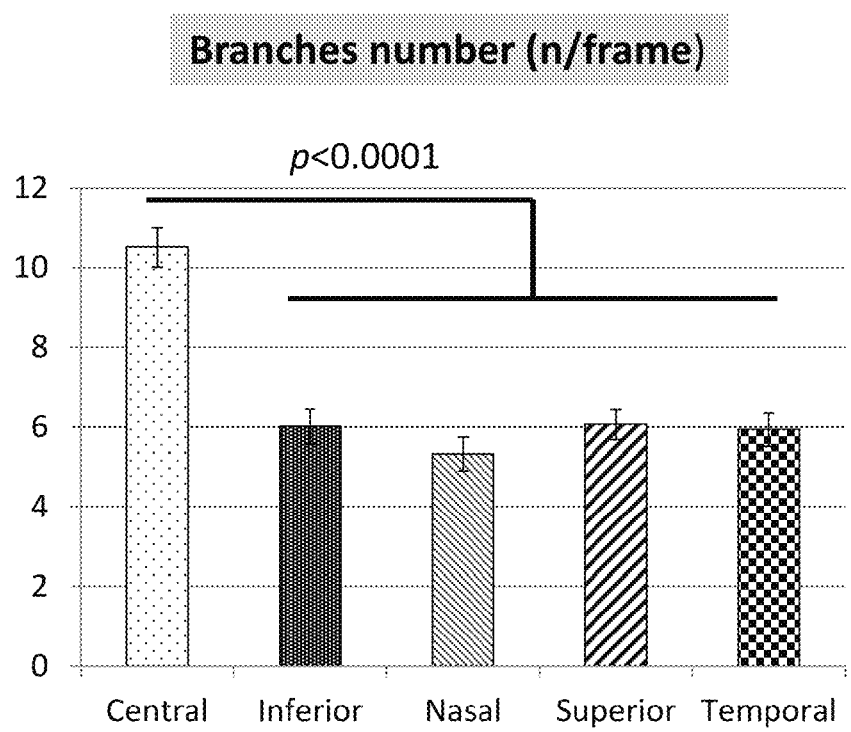
FIG. 84 is a graph of the mean nerve branch number (number/frame) in the central cornea and in each of the four peripheral cornea quadrants (inferior, nasal, superior, and temporal quadrants) in healthy (control) subjects. The data shown are the mean±SEM.
Figure 85:
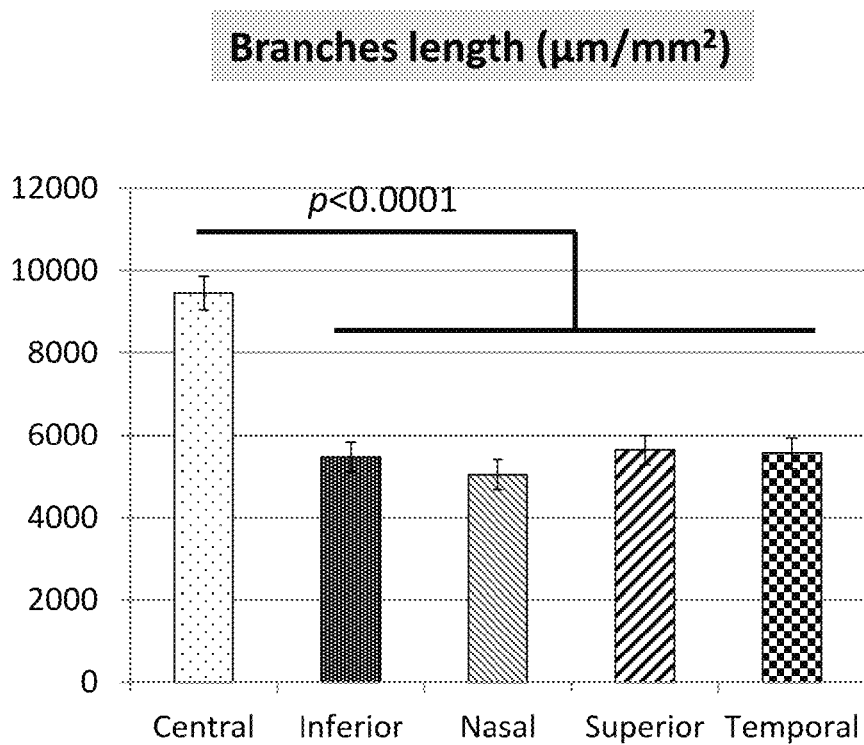
FIG. 85 is a graph of the mean nerve branch length ($\mu m/mm^2$) in the central cornea and in each of the four peripheral cornea quadrants (inferior, nasal, superior, and temporal quadrants) in healthy (control) subjects. The data shown are the mean±SEM.
Figure 86:
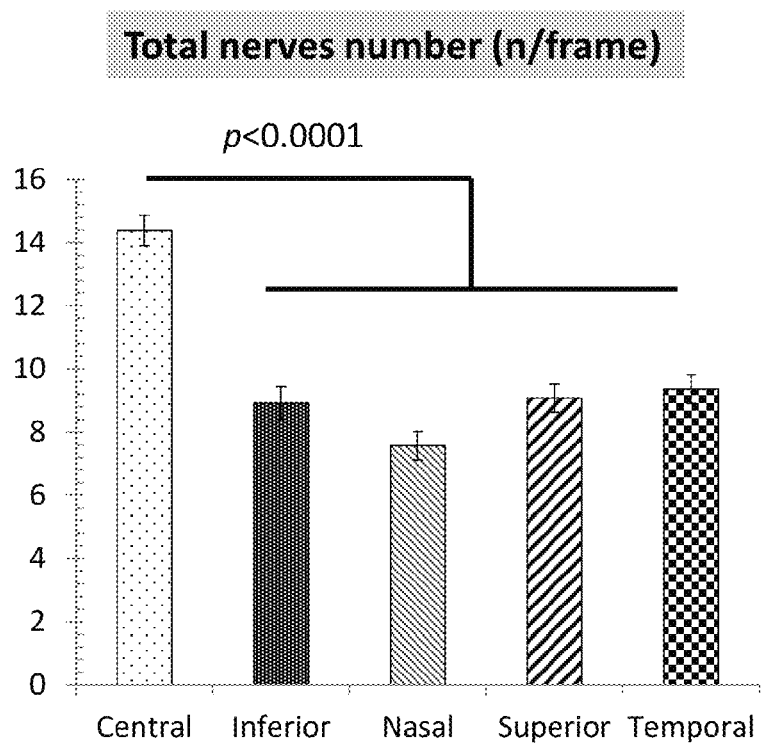
FIG. 86 is a graph of the mean total nerve number (number/frame) in the central cornea and in each of the four peripheral cornea quadrants (inferior, nasal, superior, and temporal quadrants) in healthy (control) subjects. The data shown are the mean±SEM.
Figure 87:
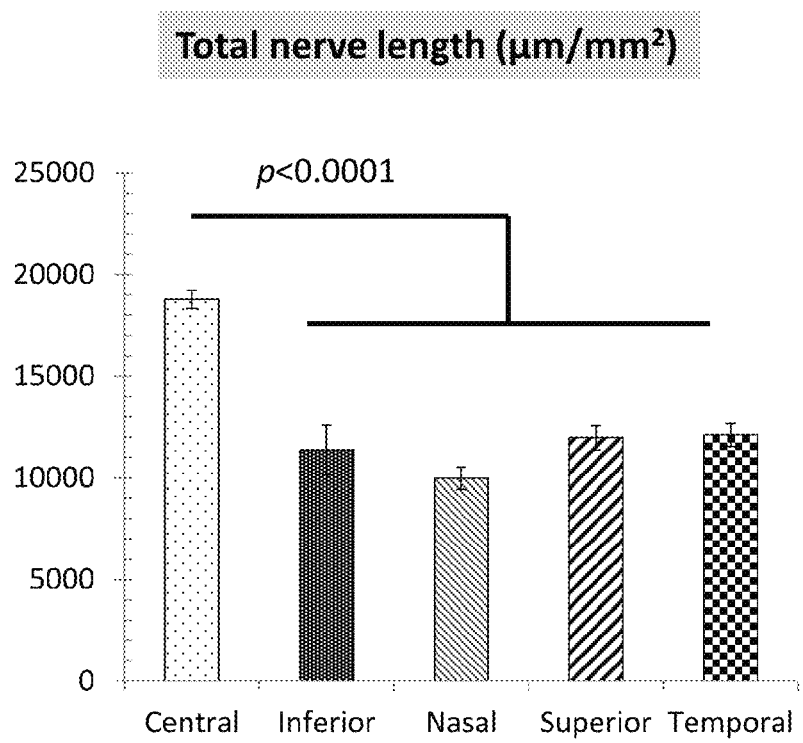
FIG. 87 is a graph of the mean total nerve length ($\mu m/mm^2$) in the central cornea and in each of the four peripheral cornea quadrants (inferior, nasal, superior, and temporal quadrants) in healthy (control) subjects. The data shown are the mean±SEM.

FIG. 82 is a graph showing the mean main nerve trunk number (number/frame) in the central cornea and in each of the four peripheral cornea quadrants (inferior, nasal, superior, and temporal quadrants) in healthy (control) subjects. FIG. 83 is a graph showing the mean main nerve trunk length (μm$^2$) in the central cornea and in each of the four peripheral cornea quadrants (inferior, nasal, superior, and temporal quadrants) in healthy (control) subjects. FIG. 84 is a graph showing the mean nerve branch number (number/frame) in the central cornea and in each of the four peripheral cornea quadrants (inferior, nasal, superior, and temporal quadrants) in healthy (control) subjects. FIG. 85 is a graph showing the mean nerve branch length (μm/mm2) in the central cornea and in each of the four peripheral cornea quadrants (inferior, nasal, superior, and temporal quadrants) in healthy (control) subjects. FIG. 86 is a graph showing the mean total nerve number (number/frame) in the central cornea and in each of the four peripheral cornea quadrants (inferior, nasal, superior, and temporal quadrants) in healthy (control) subjects. FIG. 87 is a graph showing the mean total nerve length (μm/mm2) in the central cornea and in each of the four peripheral cornea quadrants (inferior, nasal, superior, and temporal quadrants) in healthy (control) subjects. The nerve parameters revealed an inverse correlation with age (R=−0.20, p=0.017), but no correlation was found for gender and the nerve parameters (p=0.781).

TABLE 10

Nerve measurements in healthy (control) subjects

|  | Nerve fibers | | | | |
|---|---|---|---|---|---|
|  | Center | Inferior | Nasal | Superior | Temporal |
| Total nerve number (n/frame) | 14.4 ± 0.5 | 8.9 ± 0.5 | 7.6 ± 0.4 | 9.1 ± 0.4 | 9.4 ± 0.5 |
| Main trunk number (n/frame) | 3.4 ± 0.1 | 2.1 ± 0.2 | 1.7 ± 0.1 | 2.3 ± 0.1 | 2.0 ± 0.1 |
| Branch numbers (n/frame) | 10.5 ± 0.5 | 6.0 ± 0.4 | 5.3 ± 0.4 | 6.1 ± 0.4 | 5.9 ± 0.4 |
| Total nerve length (μm/mm$^2$) | 18784.0 ± 434.1 | 11375.0 ± 1233.8 | 9980.1 ± 544.4 | 11973.0 ± 600.8 | 12115.3 ± 575.6 |
| Main trunk nerve length (μm/mm$^2$) | 8853.9 ± 255.8 | 5165.2 ± 395.3 | 4437.2 ± 317.6 | 5627.7 ± 377.8 | 5258.0 ± 378.9 |
| Branch nerve length (μm/mm$^2$) | 9456.0 ± 407.2 | 5470.3 ± 370.4 | 5043.2 ± 363.3 | 5641.0 ± 361.1 | 5567.3 ± 379.2 |

Mean ± SEM

The present study determined a central cornea nerve density in healthy (control) subjects of 18,784±4002 (μm/mm$^2$) (mean±SD). Other previously calculated central cornea nerve densities (μm/mm$^2$; mean±SD) in healthy (control) subjects include: 25,929; 6968; 21,600±5980; 20,300±6500; and 19961.3±6552.9. The present study determined a mean subbasal nerve density in each of the four peripheral cornea quadrants (μm/mm$^2$; mean±SD) in healthy (control) subjects of: 11,375±5,994, inferior quadrant; 9,980±5,019, nasal quadrant; 11,973±5,539, superior; and 12,115±5,306, temporal quadrant. Other central and peripheral quadrant nerve densities (μm/mm$^2$; mean±SD) in control (healthy) subjects determined using Confoscan 2 (a slit-scanning confocal microscope) were: 14,731±6,056, central; 8,477±6,460, inferior; 7,850±4,947, nasal; 8,566±6,441, superior; and 12,556±6,909, temporal. These values and ranges determined in healthy subjects (any of the values or ranges described in this example) can be non-limiting references values or ranges in any of the methods described herein.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

The invention claimed is:

1. A method of treating a subject having dry eye syndrome, the method comprising:
using in vitro confocal microscopy to determine a number or average density of dendritic inflammatory cells present in the center of the cornea in an eye of the subject;
comparing the number or average density of dendritic inflammatory cells present in the center of the cornea in the eye of the subject to a corresponding reference value; and
selectively administering a topical steroid solution to an eye(s) of a subject having dry eye syndrome, determined to have an elevated number or density of dendritic immune cells present in the center of the cornea as compared to the reference level; or
selectively orally or topically administering two or more immunosuppressive agents to a subject having dry eye syndrome, determined to have no substantial change or a decreased number or density of dendritic immune cells present in the center of the cornea as compared to the reference level.

2. The method of claim 1, wherein the topical steroid solution comprises a steroid selected from the group consisting of: loteprednol etabonate, dexamethasone, hydrocortisone, prednisolone, prednisone, methylprednisolone, betamethasone, dexamethasone, triamcinolone, beclometasone, fludrocortisone, deoxycorticosterone, and aldosterone.

3. The method of claim 1, wherein the topical steroid solution contains loteprednol etabonate.

4. The method of claim 1, wherein the topical steroid solution is administered at least once a day.

5. The method of claim 1, wherein at least one of the at least two immunosuppressive agents is a steroid.

6. The method of claim 5, wherein the steroid is selected from the group consisting of: loteprednol etabonate, dexamethasone, hydrocortisone, prednisolone, prednisone, methylprednisolone, betamethasone, dexamethasone, triamcinolone, beclometasone, fludrocortisone, deoxycorticosterone, and aldosterone.

7. The method of claim 1, wherein at least one of the two immunosuppressive agents is selected from the group consisting of: pimecrolimus, tacrolimus, sirolimus, and cyclosporine.

8. The method of claim 1, wherein at least one of the at least two immunosuppressive agents is selected from the group consisting of: pimecrolimus, tacrolimus, sirolimus, and cyclosporine.

9. The method of claim 8, wherein the at least one immunosuppressive agent is cyclosporine.

10. The method of claim 1, wherein the at least two immunosuppressive agents are administered at least twice a week.

11. The method of claim 10, wherein the at least two immunosuppressive agents are administered at least once a day.

12. The method of claim 1, further comprising selecting a subject determined to have an elevated number or density of dendritic inflammatory cells present in the center of the cornea in the eye of the subject as compared to the corresponding reference value.

13. A method of treating a subject, the method comprising:
using in vitro confocal microscopy to determine a number or average density of dendritic inflammatory cells present in the peripheral cornea in an eye of the subject;
comparing the number or average density of dendritic inflammatory cells present in the peripheral cornea in the eye of the subject to a corresponding reference value; and
selectively topically or orally administering one or both of at least one anti-inflammatory steroid or at least one immunosuppressive agent to a subject determined to have an elevated number or elevated average density of dendritic inflammatory cells present in the peripheral cornea as compared to the corresponding reference value.

14. The method of claim 13, wherein the subject is diagnosed as having eye inflammation.

15. The method of claim 13, wherein the at least one anti-inflammatory steroid is selected from the group consisting of: hydrocortisone, cortisone, prednisone, prednisolone, methylprednisolone, dexamethasone, betamethasone, triamcinolone, beclometasone, fludrocortisone, deoxycorticosterone, and aldosterone.

16. The method of claim 13, wherein the at least one immunosuppressive agent is a calcineurin inhibitor.

17. The method of claim 16, wherein the at least one calcineurin inhibitor is selected from the group consisting of: pimecrolimus, tacrolimus, sirolimus, and cyclosporine.

18. The method of claim 13, further comprising selecting a subject determined to have an elevated number or density of dendritic inflammatory cells present in the peripheral cornea in the eye of the subject as compared to the corresponding reference value.

* * * * *